(12) United States Patent
Curtis et al.

(10) Patent No.: US 11,702,665 B2
(45) Date of Patent: Jul. 18, 2023

(54) PAENIBACILLUS-BASED ENDOSPORE DISPLAY PLATFORM, PRODUCTS AND METHODS

(71) Applicant: Ginkgo Bioworks, Inc., Boston, MA (US)

(72) Inventors: Damian Curtis, Davis, CA (US); Benjamin L. Golomb, Sacramento, CA (US); Dilara Ally, Natick, MA (US); Florencia A. Ficarra, Davis, CA (US); Rauf Salamzade, Madison, WI (US); Bjorn A. Traag, Walnut Creek, CA (US)

(73) Assignee: Ginkgo Bioworks, Inc., Boston, MA (US)

( * ) Notice: Subject to any disclaimer, the term of this patent is extended or adjusted under 35 U.S.C. 154(b) by 0 days.

(21) Appl. No.: 17/217,952

(22) Filed: Mar. 30, 2021

(65) Prior Publication Data
US 2021/0238610 A1    Aug. 5, 2021

Related U.S. Application Data

(62) Division of application No. 16/191,964, filed on Nov. 15, 2018, now Pat. No. 10,988,769.

(60) Provisional application No. 62/587,371, filed on Nov. 16, 2017.

(51) Int. Cl.
| | |
|---|---|
| *C12N 15/74* | (2006.01) |
| *C12N 9/04* | (2006.01) |
| *C07K 14/325* | (2006.01) |
| *C12N 9/24* | (2006.01) |
| *C12N 9/42* | (2006.01) |
| *C07K 14/195* | (2006.01) |
| *C12N 11/16* | (2006.01) |
| *C12N 15/62* | (2006.01) |
| *C12N 1/20* | (2006.01) |
| *C12N 15/10* | (2006.01) |
| *A01N 63/50* | (2020.01) |
| *A01N 63/10* | (2020.01) |
| *A01N 63/00* | (2020.01) |

(52) U.S. Cl.
CPC ............ *C12N 15/74* (2013.01); *A01N 63/00* (2013.01); *A01N 63/10* (2020.01); *A01N 63/50* (2020.01); *C07K 14/195* (2013.01); *C07K 14/325* (2013.01); *C12N 1/20* (2013.01); *C12N 9/0006* (2013.01); *C12N 9/24* (2013.01); *C12N 9/2442* (2013.01); *C12N 11/16* (2013.01); *C12N 15/1037* (2013.01); *C12N 15/625* (2013.01); *C12Y 101/01004* (2013.01); *C12Y 302/01014* (2013.01); *C07K 2319/035* (2013.01)

(58) Field of Classification Search
None
See application file for complete search history.

(56) References Cited

U.S. PATENT DOCUMENTS

| | | |
|---|---|---|
| 5,766,914 A | 6/1998 | Deits |
| 5,800,821 A | 9/1998 | Acheson et al. |
| 7,582,426 B2 | 9/2009 | Kim et al. |
| 8,030,064 B2 | 10/2011 | Lee et al. |
| 9,132,175 B2 * | 9/2015 | Stewart ............... A61K 39/12 |
| 9,133,251 B2 | 9/2015 | Stewart et al. |
| 9,883,676 B2 | 2/2018 | Beau et al. |
| 10,159,257 B2 | 12/2018 | Beau et al. |
| 10,988,769 B2 | 4/2021 | Curtis et al. |
| 2003/0165538 A1 | 9/2003 | Goldman et al. |
| 2004/0180348 A1 | 9/2004 | Pan et al. |
| 2016/0278388 A1 | 9/2016 | Beau et al. |
| 2019/0069557 A1 | 3/2019 | Beau et al. |

FOREIGN PATENT DOCUMENTS

| | | |
|---|---|---|
| WO | WO-02/046388 A1 | 6/2002 |
| WO | WO-03/102203 A1 | 12/2003 |
| WO | WO-2006012366 A2 | 2/2006 |
| WO | WO-2014145964 A1 | 9/2014 |
| WO | WO-2016044655 A2 | 3/2016 |
| WO | WO-2016044661 A1 | 3/2016 |
| WO | WO-2016140702 A1 | 9/2016 |
| WO | WO-2016154297 A1 | 9/2016 |

OTHER PUBLICATIONS

Sylvestre et al (Mol. Microbiol., 45:169-178, 2002.*
Bowie, James U., et al. "Deciphering the message in protein sequences: tolerance to amino acid substitutions." *Science* 247.4948 (1990): 1306-1310.
Boydston, Jeremy A., et al. "Orientation within the exosporium and structural stability of the collagen-like glycoprotein BclA of Bacillus anthracis." *Journal of bacteriology* 187.15 (2005): 5310-5317.
Burgess, Wilson H., et al. "Possible dissociation of the heparin-binding and mitogenic activities of heparin-binding (acidic fibroblast) growth factor-1 from its receptor-binding activities by site-directed mutagenesis of a single lysine residue." *The Journal of Cell Biology* 111.5 (1990): 2129-2138.
Grady, Elliot Nicholas, et al. "Current knowledge and perspectives of Paenibacillus: a review." *Microbial cell factories* 15.1 (2016): 1-18.
Henriques et al., "Structure, assembly, and function of the spore surface layers." *Annu. Rev. Microbiol.* 61 (2007): 555-588.
International Search Report and Written Opinion for International Application No. PCT/US2018/061233 dated Apr. 17, 2019.

(Continued)

*Primary Examiner* — Brian Gangle
(74) *Attorney, Agent, or Firm* — Foley Hoag LLP; Thi K. Dio; Lee Chedister

(57) ABSTRACT

Signal sequences useful for targeting proteins and peptides to the surface of endospores produced by *Paenibacillus* family members and methods of using the same are provided. The display of heterologous molecules, such as peptides, polypeptides and other recombinant constructs, on the spore surface of *Paenibacillus* family members, using particular N-terminal targeting sequences and derivatives of the same, are also provided.

7 Claims, 4 Drawing Sheets
(1 of 4 Drawing Sheet(s) Filed in Color)
Specification includes a Sequence Listing.

(56) References Cited

OTHER PUBLICATIONS

Kailas, Lekshmi, et al. "Surface architecture of endospores of the Bacillus cereus/anthracis/thuringiensis family at the subnanometer scale." *Proceedings of the National Academy of Sciences* 108.38 (2011): 16014-16019.
Lazar, Eliane, et al. "Transforming growth factor alpha: mutation of aspartic acid 47 and leucine 48 results in different biological activities." *Molecular and Cellular Biology* 8.3 (1988): 1247-1252.
Maes, Emmanuel, et al. "Glycosylation of BclA glycoprotein from Bacillus cereus and Bacillus anthracis exosporium is domain-specific." *Journal of Biological Chemistry* 291.18 (2016): 9666-9677.
NCBI, "collagen-like repeat preface domain-containing protein [Paenibacillus terrae]", WP_044645353.
Rasmussen et al., "SclA, a novel collagen-like surface protein of *Streptococcus pyogenes." Infection and immunity* 68.11 (2000): 6370-6377.
Rodenburg, Cynthia M., et al. "Cryo-EM analysis of the organization of BclA and BxpB in the Bacillus anthracis exosporium." *Journal of structural biology* 186.1 (2014): 181-187.
Stewart, George C. "The exosporium layer of bacterial spores: a connection to the environment and the infected host." *Microbiology and Molecular Biology Reviews* 79.4 (2015): 437-457.
Sylvestre et al. "A collagen-like surface glycoprotein is a structural component of the Bacillus anthracis exosporium." Molecular microbiology 45.1 (2002): 169-178.
Sylvestre et al., "Polymorphism in the collagen-like region of the Bacillus anthracis BclA protein leads to variation in exosporium filament length." *Journal of bacteriology* 185.5 (2003): 1555-1563.
Tan et al., "Sequence motifs and proteolytic cleavage of the collagen-like glycoprotein BclA required for its attachment to the exosporium of Bacillus anthracis." *Journal of bacteriology* 192.5 (2010): 1259-1268.
Thompson, Brian M., and George C. Stewart. "Targeting of the BclA and BclB proteins to the Bacillus anthracis spore surface." *Molecular microbiology* 70.2 (2008): 421-434.
Thompson, Brian M., et al. "Localization and assembly of the novel exosporium protein BetA of Bacillus anthracis." *Journal of bacteriology* 193.19 (2011): 5098-5104.
Thompson, Brian M., et al. "The BclB glycoprotein of Bacillus anthracis is involved in exosporium integrity." *Journal of bacteriology* 189.18 (2007): 6704-6713.
Thompson, Brian M., et al. "The co-dependence of BxpB/ExsFA and BclA for proper incorporation into the exosporium of Bacillus anthracis." Molecular microbiology 79.3 (2011): 799-813.
Wu, I-Lin, et al. "A versatile nano display platform from bacterial spore coat proteins." *Nature communications* 6.1 (2015): 1-8.
Xu, Kai, et al. "Genome comparison provides molecular insights into the phylogeny of the reassigned new genus *Lysinibacillus."* *BMC genomics* 16.1 (2015): 1-12.
Zhao, Ni, et al. "Collagen-like glycoprotein BclS is involved in the formation of filamentous structures of the Lysinibacillus sphaericus exosporium." *Applied and Environmental Microbiology* 80.21 (2014): 6656-6663.

\* cited by examiner

```
SEQ_ID_NO_2_1-119  MVVLSTGPIA  NDPVLGVRPT  QLVTVKIDNR  DSVNSSIVLI  EGFILNGSRT  LYVQQLVVVG  PNAVITRNFF  ANVDAFEFVF  80
SEQ_ID_NO_8_1-120  MAVISTGPIE  NNYVSGIRPT  HRYTVKIDNR  DTVNSSTVLI  QGFYLNGTRT  LYVLDFITVN  SNEVITKDYY  ADFNSFEFVF  80
       Consensus   MXVXSTGPIX  NXXVXGXRPT  XXVTVKIDNR  DXVNSSXVLI  XGFXLNGXRT  LYVXXXXXVX  XNXVITKXXX  AXXXXFEFVF SEQ_ID_NO_2_1-119  TTSGPAENET  QISVWGKDAL  GQLVPAHRLV  SQELL-GTQR  119
SEQ_ID_NO_8_1-120  TTESVTENEI  QVSVWGKNSM  GQLVTAHRVV  SSELLVAKGA  120
       Consensus   TTXXXXENEX  QXSVWGKXXX  GQLVXAHRXV  SXELLVXXXX

FIG. 3
```

PAENIBACILLUS-BASED ENDOSPORE DISPLAY PLATFORM, PRODUCTS AND METHODS

CROSS REFERENCE TO RELATED APPLICATIONS

This application is a divisional of U.S. patent application Ser. No. 16/191,964, filed Nov. 15, 2018, and issued as U.S. Pat. No. 10,988,769, which claims priority to U.S. Provisional Patent Application No. 62/587,371, filed Nov. 16, 2017, the content of which is incorporated herein by reference in its entirety.

REFERENCE TO SEQUENCE LISTING SUBMITTED ELECTRONICALLY

The official copy of the sequence listing is submitted electronically via EFS-Web as an ASCII-formatted sequence listing with a file named "BCS179003WO_ST25.txt" created on Nov. 13, 2018, and having a size of 80 kilobytes, and is filed concurrently with the specification. The sequence listing contained in this ASCII-formatted document is part of the specification and is herein incorporated by reference in its entirety.

TECHNICAL FIELD

The disclosure is generally directed to endospore display platforms, related display methods, spore surface targeting sequences and fusion protein constructs comprising the same, recombinant endospore compositions, and methods for identifying spore surface-targeting sequences in *Paenibacillus* and other bacterial genera that are useful for various applications such as the delivery of a heterologous molecule of interest to a plant, seed or field.

BACKGROUND OF THE DISCLOSURE

Modern agricultural techniques rely heavily on compositions that promote or enhance plant health and growth in order to improve the yield and quality of crops. Such compositions generally include organic or inorganic fertilizers, nutrients and other chemical compounds that promote proper plant growth and development. However, it is well established that long-term or overuse of many of these compositions may result in negative side effects, such as soil acidification or destabilization of the nutrient balance in the soil. Moreover, overuse may result in the enrichment of harmful end-products in crops grown for human consumption.

Modern farms also typically rely on the use of a wide variety of chemicals (e.g., insecticides, herbicides, bactericides, nematicides, and fungicides) to control pests and ensure a high yield of commercially-grown crops. Many of these chemical compounds exhibit broad activity and may be potentially harmful to humans and animals in high concentrations. In addition, some chemical compounds exhibit off-target effects. Moreover, at least some of these synthetic compounds are non-biodegradable. In recent years, there has been increasing pressure from consumers for agricultural products that have been raised and harvested with reduced or no exposure to synthetic insecticides or fungicides. A further problem arising with the use of synthetic insecticides or fungicides is that the repeated and/or exclusive use often leads to selection of resistant pests. Normally, resistant pests are also cross-resistant against other active ingredients having the same mode of action. As a result, pest control compositions and compounds are difficult and expensive to develop (e.g., due to safety concerns and the rapid development of resistance).

Genetic engineering methods are used to promote plant growth and/or health without reliance on synthetic chemicals. For example, crops can be modified to introduce or modify genes related to plant growth and/or health, and/or to introduce genes that encode natural or synthetic pest control agents. Transgenes may be introduced into a target plant using a viral vector. In recent years, there has been some success reported using bacteria for delivery of recombinant proteins to plants. However, to date, such success is largely limited to members of the Bacillaceae family and more specifically, *Bacillus subtilis*, which is the most well-characterized, Gram-positive bacteria and the primary bacterial model for sporulation research. The focus on *B. subtilis* as a delivery and expression platform is further due to the fact that the *B. subtilis* genome and biological pathways related to protein synthesis and secretion are well understood. However, due to the high degree of genetic diversity among bacteria, research findings based on *B. subtilis* studies are often not directly translatable to members inside and outside the Bacillaceae family Accordingly, while certain methods of delivering heterologous genetic materials are known, there is a need in the art for developing new delivery and expression platforms for such genetic materials.

BRIEF SUMMARY OF EMBODIMENTS OF THE DISCLOSURE

The disclosure describes methods, compositions and genetic constructs that address the needs identified above by, for example, providing, among other things, a new platform for delivering recombinant enzymes and other molecules of interest (e.g., peptide, protein) to an environment (e.g., plant, field) using spore-forming members of the *Paenibacillus* genus. The disclosure also provides methods of identifying spore surface-targeting sequences in *Paenibacillus* and other bacterial genera.

In one aspect, the disclosure provides recombinant endospore-producing *Paenibacillus* cells that express a fusion protein comprising: (i) at least one heterologous protein or peptide that confers or modifies a plant trait or attribute (e.g., an enzyme involved in the production or activation of a plant growth stimulating compound; an enzyme that degrades or modifies a bacterial, fungal, or plant nutrient source; a microbicidal or microbiostatic compound; or an enzyme, protein, or peptide that protects a plant from a pathogen or a pest); and (ii) an N-terminal targeting sequence that localizes the fusion protein to the spore surface of the *Paenibacillus* cells. This general composition may further include additional components (e.g., that promote plant growth and/or health). Moreover, particular embodiments of the methods discloses herein provide for an efficient high-throughput screening of heterologous proteins and peptide that confer or otherwise modify plant traits or attributes.

In an alternative aspect, the disclosure provides a nucleic acid molecule encoding a fusion protein, comprising (a) a first polynucleotide sequence encoding an N-terminal signal peptide, operably linked to (b) a second polynucleotide sequence encoding a polypeptide heterologous to the N-terminal signal peptide, wherein the first polynucleotide sequence comprises: (i) a polynucleotide sequence encoding an N-terminal signal peptide; (ii) a polynucleotide sequence having at least 50%, 60%, 70%, 80% or 90% sequence identity with SEQ ID NO: 1, 3, 5, 7 or 9; or (iii) a polynucleotide sequence comprising a fragment of at least 5, 10, 15, 20, 25, 30, 35, 40, 45, 50, 55 or 60 consecutive nucleotides of SEQ ID NO: 1, 3, 5, 7 or 9; wherein the N-terminal signal peptide is capable of targeting the fusion protein to the spore surface of a *Paenibacillus* endospore.

In another alternative aspect, the disclosure provides a nucleic acid molecule encoding a fusion protein, comprising (a) a first polynucleotide sequence encoding an N-terminal signal peptide, operably linked to (b) a second polynucleotide sequence encoding a polypeptide heterologous to the N-terminal signal peptide, wherein the first polynucleotide sequence comprises: (i) a polynucleotide sequence having at least 50%, 60%, 70%, 80% or 90% sequence identity with SEQ ID NO: 1, 3, 5, 7 or 9 or (ii) a polynucleotide sequence comprising a fragment of at least 5, 10, 15, 20, 25, 30, 35, 40, 45, 50, 55 or 60 consecutive nucleotides of SEQ ID NO: 1, 3, 5, 7 or 9; wherein the N-terminal signal peptide is capable of targeting the fusion protein to the spore surface of a *Paenibacillus* endospore.

In some aspects, the polypeptide heterologous to the N-terminal signal peptide comprises: (a) at least one of a plant growth or immune stimulating protein; (b) an enzyme; (c) a protein; (d) a polypeptide heterologous to *Paenibacillus*; or (e) a therapeutic protein. In selected aspects, the nucleic acid molecule further comprising a third polynucleotide sequence, encoding: (a) a polypeptide comprising one or more protease cleavage sites, wherein the polypeptide is positioned between the N-terminal signal peptide and the polypeptide heterologous to the N-terminal signal peptide; (b) a polypeptide comprising a selectable marker; (c) a polypeptide comprising a visualization marker; (d) a polypeptide comprising a protein recognition/purification domain; or (e) a polypeptide comprising a flexible linker element, which connects the N-terminal signal peptide and the polypeptide heterologous to the N-terminal signal peptide.

In some aspects, the *Paenibacillus* endospore is an endospore formed by a *Paenibacillus* species, comprising: *Paenibacillus* sp. NRRL B-50972, *Paenibacillus terrae*, *Paenibacillus polymyxa*, or *Paenibacillus peoriae*.

In other aspects, the *Paenibacillus* endospore is an endospore formed by a *Paenibacillus* species, comprising: *Paenibacillus abyssi, Paenibacillus aceti, Paenibacillus aestuarii, Paenibacillus agarexedens, Paenibacillus agaridevorans, Paenibacillus alginolyticus, Paenibacillus algorifonticola, Paenibacillus alkaliterrae, Paenibacillus alvei, Paenibacillus amylolyticus, Paenibacillus anaericanus, Paenibacillus antarcticus, Paenibacillus apiarius, Paenibacillus arachidis, Paenibacillus assamensis, Paenibacillus azoreducens, Paenibacillus azotofixans, Paenibacillus baekrokdamisoli, Paenibacillus barcinonensis, Paenibacillus barengoltzii, Paenibacillus borealis, Paenibacillus bovis, Paenibacillus brasilensis, Paenibacillus camelliae, Paenibacillus campinasensis, Paenibacillus castaneae, Paenibacillus catalpae, Paenibacillus cathormii, Paenibacillus cavernae, Paenibacillus cellulosilyticus, Paenibacillus cellulositrophicus, Paenibacillus chartarius, Paenibacillus chibensis, Paenibacillus chinjuensis, Paenibacillus chitinolyticus, Paenibacillus chondroitinus, Paenibacillus chungangensis, Paenibacillus cineris, Paenibacillus cisolokensis, Paenibacillus contaminans, Paenibacillus cookii, Paenibacillus cucumis, Paenibacillus curdlanolyticus, Paenibacillus daejeonensis, Paenibacillus darwinianus, Paenibacillus dauci, Paenibacillus dendritiformis, Paenibacillus dongdonensis, Paenibacillus doosanensis, Paenibacillus durus, Paenibacillus edaphicus, Paenibacillus ehimensis, Paenibacillus elgii, Paenibacillus endophyticus, Paenibacillus etheri, Paenibacillus faecis, Paenibacillus favisporus, Paenibacillus ferrarius, Paenibacillus filicis, Paenibacillus fonticola, Paenibacillus forsythiae, Paenibacillus frigoriresistens, Paenibacillus gansuensis, Paenibacillus gelatinilyticus, Paenibacillus ginsengarvi, Paenibacillus ginsengihumi, Paenibacillus ginsengisoli, Paenibacillus glacialis, Paenibacillus glucanolyticus, Paenicillus glycanilyticus, Paenibacillus gordonae, Paenibacillus graminis, Paenibacillus granivorans, Paenibacillus guangzhouensis*, or *Paenibacillus harenae.*

In some aspects, the *Paenibacillus* endospore is an endospore formed by a *Paenibacillus* species, comprising: *Paenibacillus hemerocallicola, Paenibacillus hispanicus, Paenibacillus hodogayensis, Paenibacillus hordei, Paenibacillus humicus, Paenibacillus hunanensis, Paenibacillus illinoisensis, Paenibacillus jamilae, Paenibacillus jilunlii, Paenibacillus kobensis, Paenibacillus koleovorans, Paenibacillus konsidensis, Paenibacillus koreensis, Paenibacillus kribbensis, Paenibacillus kyungheensis, Paenibacillus lactis, Paenibacillus larvae, Paenibacillus larvae, Paenibacillus larvae, Paenibacillus lautus, Paenibacillus lemnae, Paenibacillus lentimorbus, Paenibacillus lentus, Paenibacillus liaoningensis, Paenibacillus lupini, Paenibacillus macerans, Paenibacillus macquariensis, Paenibacillus macquariensis, Paenibacillus macquariensis, Paenibacillus marchantiophytorum, Paenibacillus marinisediminis, Paenibacillus massiliensis, Paenibacillus medicaginis, Paenibacillus mendelii, Paenibacillus methanolicus, Paenibacillus montaniterrae, Paenibacillus motobuensis, Paenibacillus mucilaginosus, Paenibacillus nanensis, Paenibacillus nap hthalenovorans, Paenibacillus nasutitermitis, Paenibacillus nematophilus, Paenibacillus nicotianae, Paenibacillus oceanisediminis, Paenibacillus odorifer, Paenibacillus oenotherae, Paenibacillus oryzae, Paenibacillus pabuli, Paenibacillus panacisoli, Paenibacillus panaciterrae, Paenibacillus pasadenensis, Paenibacillus pectinilyticus, Paenibacillus periandrae*, or *Paenibacillus phoenicis.*

In some aspects, the *Paenibacillus* endospore is an endospore formed by a *Paenibacillus* species, comprising: *Paenibacillus phyllosphaerae, Paenibacillus physcomitrellae, Paenibacillus pini, Paenibacillus pinihumi, Paenibacillus pinesoli, Paenibacillus pocheonensis, Paenibacillus popilliae, Paenibacillus populi, Paenibacillus prosopidis, Paenibacillus provencensis, Paenibacillus pueri, Paenibacillus puldeungensis, Paenibacillus pulvifaciens, Paenibacillus purispatii, Paenibacillus qingshengii, Paenibacillus quercus, Paenibacillus radicis, Paenibacillus relictisesami, Paenibacillus residui, Paenibacillus rhizoryzae, Paenibacillus rhizosphaerae, Paenibacillus rigui, Paenibacillus riograndensis, Paenibacillus ripae, Paenibacillus sabinae, Paenibacillus sacheonensis, Paenibacillus salinicaeni, Paenibacillus sanguinis, Paenibacillus sediminis, Paenibacillus segetis, Paenibacillus selenii, Paenibacillus selenitireducens, Paenibacillus senegalensis, Paenibacillus septentrionalis, Paenibacillus sepulcri, Paenibacillus shenyangensis, Paenibacillus shirakamiensis, Paenibacillus siamensis, Paenibacillus silagei, Paenibacillus sinopodophylli, Paenibacillus solani, Paenibacillus soli, Paenibacillus sonchi, Paenibacillus sophorae, Paenibacillus sputi, Paenibacillus stellifer, Paenibacillus susongensis, Paenibacillus swuensis, Paenibacillus taichungensis, Paenibacillus taiwanensis, Paenibacillus tarimensis, Paenibacillus telluris, Paenibacillus terreus, Paenibacillus terrigena, Paenibacillus thailandensis, Paenibacillus thermophilus, Paenibacillus thiaminolyticus, Paenibacillus tianmuensis, Paenibacillus*

*tibetensis, Paenibacillus timonensis, Paenibacillus tundrae, Paenibacillus turicensis, Paenibacillus typhae, Paenibacillus uliginis, Paenibacillus urinalis, Paenibacillus validus, Paenibacillus vini, Paenibacillus vulneris, Paenibacillus wenxiniae, Paenibacillus wooponensis, Paenibacillus woosongensis, Paenibacillus wulumuqiensis, Paenibacillus wynnii, Paenibacillus xanthinilyticus, Paenibacillus xinjiangensis, Paenibacillus xylanexedens, Paenibacillus xylanilyticus, Paenibacillus xylanisolvens, Paenibacillus yonginensis, Paenibacillus yunnanensis, Paenibacillus zanthoxyli,* or *Paenibacillus zeae.*

In some aspects, the nucleic acid molecule is operatively linked to a promoter element that is heterologous to at least one of the second polynucleotide sequence and *Paenibacillus.*

In some aspects, the first polynucleotide sequence comprises: (a) a codon-optimized polynucleotide sequence having at least 50%, 60%, 70%, 80% or 90% sequence identity with SEQ ID NO: 1, 3, 5, 7 or 9, which is expressed at a higher rate or level in the *Paenibacillus* endospore compared to the respective original SEQ ID NO: 1, 3, 5, 7 or 9, under identical conditions.

In an alternative aspect, the disclosure provides a fusion protein comprising an N-terminal signal peptide operably linked to a polypeptide heterologous to the N-terminal signal peptide, wherein the N-terminal signal peptide comprises: (a) a polypeptide comprising an amino acid sequence having at least 50%, 60%, 70%, or 80% sequence identity with the amino acid sequence of SEQ ID NO: 2, 4, 6, 8 or 10; or (b) a polypeptide comprising a fragment of at least 5, 10, 15, 20, 25 or 30 consecutive amino acids of SEQ ID NO: 2, 4, 6, 8 or 10; wherein the N-terminal signal peptide is capable of targeting the fusion protein to the spore surface of a *Paenibacillus* endospore.

In some aspects, the polypeptide heterologous to the N-terminal signal peptide comprises: (a) at least one of a plant growth or immune stimulating protein; (b) an enzyme; (c) a polypeptide heterologous to *Paenibacillus*; (d) a therapeutic protein (e.g., an antibiotic or anti-inflammatory protein); or (e) a protein that provides an agriculturally-significant property, included, but not limited to: insecticidal/insectistatic activity, bactericidal/bacteriostatic activity, fungicidal/fungistatic activity, plant growth, health or immune-stimulating activity, and/or improved abiotic environmental resistance. Other agriculturally-significant properties include improved crop characteristics including: emergence, crop yields, protein content, oil content, starch content, more developed root system, improved root growth, improved root size maintenance, improved root effectiveness, improved stress tolerance (e.g., against drought, heat, salt, UV, water, cold), reduced ethylene (reduced production and/or inhibition of reception), tillering increase, increase in plant height, bigger leaf blade, less dead basal leaves, stronger tillers, greener leaf color, pigment content, photosynthetic activity, less input needed (such as fertilizers or water), less seeds needed, more productive tillers, earlier flowering, early grain maturity, less plant verse (lodging), increased shoot growth, enhanced plant vigor, increased plant stand and early and better germination.

In some aspects, the fusion protein further comprises: (a) a polypeptide containing one or more protease cleavage sites, positioned between the N-terminal signal peptide and the polypeptide heterologous to the N-terminal signal peptide; (b) a polypeptide comprising a selectable marker (e.g., a protein that confers resistance to an antibiotic); (c) a polypeptide comprising a visualization element (e.g., a fluorescent tag such as GFP); (d) a polypeptide comprising at least one protein recognition/purification domain (e.g., a His-tag); or (e) a polypeptide comprising a flexible linker element, connecting the signal peptide and the polypeptide heterologous to the N-terminal signal peptide.

In an alternative aspect, the disclosure provides a recombinant *Paenibacillus* cell comprising a bacterial chromosome comprising the nucleic acid molecule of any one of the previous aspects.

In an alternative aspect, the disclosure provides a vector comprising the nucleic acid molecule of any one of the previous aspects, wherein the vector comprises a plasmid, an artificial chromosome, or a viral vector.

In some aspects, the vector further comprising at least one of the following: (a) an origin of replication that provides stable maintenance in a *Paenibacillus* cell; (b) an origin of replication that provides selectively non-stable maintenance in a *Paenibacillus* cell; (c) a temperature-sensitive origin of replication that provides selectively non-stable maintenance in a *Paenibacillus* cell; (d) a polynucleotide encoding a selection marker, operably linked to an expression control sequence; or (e) a polynucleotide encoding a plant growth stimulating protein, operably linked to an expression control sequence.

In alternative aspects, the disclosure provides a recombinant *Paenibacillus* cell transformed with a vector comprising the nucleic acid molecule of any one of the aspects disclosed herein.

In some aspects, the *Paenibacillus* cell is a *Paenibacillus* species, comprising: *Paenibacillus* sp. NRRL B-50972, *Paenibacillus terrae, Paenibacillus polymyxa*, or *Paenibacillus peoriae*. In other exemplary aspects, the *Paenibacillus* cell may be selected from any of the exemplary *Paenibacillus* species described herein.

In alternative aspects, the disclosure provides a method of displaying a heterologous fusion protein on the spore surface of a *Paenibacillus* endospore, the method comprising: a) transforming a *Paenibacillus* cell capable of sporulation with a recombinant vector comprising the nucleic acid molecule of any one of the aspects disclosed herein; and b) expressing the fusion protein encoded by the nucleic acid molecule of any one of the aspects disclosed herein under sporulation conditions such that the fusion protein is targeted to the spore surface of the *Paenibacillus* endospore resulting from the sporulation, wherein the N-terminal signal peptide comprises: (i) a polypeptide comprising an amino acid sequence having at least 50%, 60%, 70%, 80% or 90% sequence identity with the amino acid sequence of SEQ ID NO: 2; or (ii) a fragment of at least 5, 10, 15 or 20 consecutive amino acids from SEQ ID NO: 2.

In alternative aspects, the disclosure provides a composition comprising: a) one or more recombinant endospore-producing *Paenibacillus* cells that express the fusion protein of any one of the aspects disclosed herein, wherein the polypeptide heterologous to the N-terminal signal peptide comprises a plant growth or immune stimulating protein; and b) at least one biological control agent; optionally, in a synergistically effective amount.

In alternative aspects, the disclosure provides a seed treated with at least one of the nucleic acids, fusion proteins, bacterial cells or compositions of any one of the aspects disclosed herein.

In alternative aspects, the disclosure provides a method of treating a plant, a seed, a plant part, or the soil surrounding the plant to enhance plant growth and/or promote plant health comprising the step of simultaneously or sequentially applying: a) recombinant endospore-producing *Paenibacillus* endospores that express the fusion protein of any of the aspects disclosed herein, wherein the polypeptide heterologous to the N-terminal signal peptide comprises a plant growth or immune stimulating protein; and b) at least one biological control agent; optionally, in a synergistically effective amount.

In alternative aspects, the disclosure provides a method of screening a host plant treated with a recombinant *Paenibacillus* endospore, comprising the following steps: a) applying a composition comprising a *Paenibacillus* endospore modified to express a fusion protein according to any of the aspects disclosed herein, to a seed, a seedling, or a vegetative plant capable of being permanently or transiently colonized by a *Paenibacillus*, to produce a treated seed, seedling, or vegetative plant; b) screening the treated seed, seedling, or vegetative plant by detecting and optionally measuring a trait, component, or attribute of the treated seed, seedling, or vegetative plant.

In some aspects, the screening step comprises one or more of the following: a) at least one in vitro assay comprising detecting and optionally quantifying the presence, level, change in level, activity, or localization of one or more compounds contained in an extract prepared from a cell or tissue sample obtained from the treated seed, seedling, or vegetative plant; and/or b) at least one in vivo assay comprising detecting and optionally quantifying a trait, component, or attribute of the treated seed, seedling, or vegetative plant.

In alternative aspects, the disclosure provides a method of screening heterologous proteins or peptides expressed in a *Paenibacillus* cell for agriculturally-significant properties, comprising: a) modifying a *Paenibacillus* cell to express a fusion protein according to the aspects disclosed herein to produce a recombinant *Paenibacillus* cell; and b) screening the *Paenibacillus* cell by detecting and optionally quantifying a level or activity of a compound produced by the recombinant *Paenibacillus* cell.

In alternative aspects, the disclosure provides a method for identifying spore surface-targeting sequences in *Paenibacillus* and other bacterial genera suitable for endospore display, comprising: screening a genome of a *Paenibacillus* or another endospore-forming bacteria of interest for open reading frames that encode proteins having multiple collagen-like triplet repeats of "Gly-X-X" ("GXX repeats" where "X" represents any amino acid); and determining that the protein localizes to the spore surface by microscopy or experimentally. In some aspects, the protein localization is determined using transmission electron microscopy or mass spectrometry. In other aspects, the putative N-terminal targeting sequence from a protein that localizes to the spore surface is fused to a reporter gene and the resulting fusion protein is expressed in an endospore-forming bacterium. In yet other aspects, the resulting fusion protein is analyzed for expression on the surface of such endospore-forming bacterium. In another aspect, if such expression is detected, the reporter gene is replaced with a nucleotide sequence of interest and such second fusion protein is expressed in an endospore-forming bacterium.

In some aspects, the disclosure provides spore surface-targeting targeting sequences from *Paenibacillus* and other bacterial genera comprising an N-terminal targeting sequence of a protein identified via the aforementioned method. This N-terminal targeting sequence may comprise the first 5, 10, 15, 20, 25, 30, 35, 40, 50, 60, 70, 80, 90, 100, 110, or 120 amino acids of the protein, or a fragment or variant thereof. In some aspects, the N-terminal targeting sequence is a variant that is at least 60%, 70%, 80%, 90% or 95% identical to the endogenous N-terminal targeting sequence. Spore surface targeting sequences in *Paenibacillus* and other bacterial genera identified using these methods may be used to generate heterologous fusion proteins according to any of the various embodiments described herein.

In selected aspects, the composition has been heat-inactivated or sterilized such that no viable *Paenibacillus* cells remain.

In alternative aspects, the disclosure provides a composition comprising an isolated and/or purified fusion protein according to any one of the aspects disclosed herein.

In alternative aspects, the disclosure provides a method of delivering a protein of interest to a plant, seed or field, comprising: applying a composition comprising a recombinant *Paenibacillus* endospore to a plant, seed, or field; wherein the recombinant *Paenibacillus* endospore has been modified to express a fusion protein according to any of the aspects disclosed herein.

In some aspects, the composition is applied to a field: a) pre- or post-planting; b) pre- or post-emergence; c) as a powder, suspension or solution; or d) wherein the composition further comprises one or more additional compounds that stimulate plant growth.

In some embodiments, the present invention provides a nucleic acid molecule encoding a fusion protein, comprising (a) a first polynucleotide sequence encoding an N-terminal signal peptide, operably linked to (b) a second polynucleotide sequence encoding a polypeptide heterologous to the N-terminal signal peptide, wherein the first polynucleotide sequence comprises: (i) a polynucleotide sequence comprising at least 15, 30, 45, 60, 75 or 90 nucleotides; (ii) a polynucleotide sequence having at least 50%, 60%, 70%, 80% or 90% sequence identity with SEQ ID NO: 1, 3, 5, 7, 9, 19, 23, 25, 27, or 29; or (iii) a polynucleotide sequence comprising a fragment of at least 45, 90, 135, 180, 225, 270, 315, or 345 consecutive nucleotides of SEQ ID NO: 1, 3, 5, 7, 9, 19, 23, 25, 27, or 29; wherein the N-terminal signal peptide is capable of targeting the fusion protein to a spore surface of a *Paenibacillus* endospore.

In one aspect, the fragment starts at the first nucleotide of SEQ ID NO: 1, 3, 5, 7, 9, 19, 23, 25, 27, or 29. In another aspect, the first polynucleotide sequence comprises a polynucleotide sequence having at least 50%, 60%, 70%, 80% or 90% sequence identity with SEQ ID NO: 1, 7, 19, or 27. In another aspect, the fragment encodes amino acids 1-15, or 1-30, 1-45, 1-60, 1-75, 1-90, 1-105, or 1-115 of SEQ ID NO: 2 or SEQ ID NO: 8.

In one embodiment, the polypeptide heterologous to the N-terminal signal peptide comprises: (a) a plant growth-stimulating protein; (b) an enzyme; (c) a protein; (d) a polypeptide heterologous to *Paenibacillus*; (e) a therapeutic protein; or (f) a plant immune-stimulating protein.

In another embodiment, the nucleic acid further comprising a third polynucleotide sequence, encoding: (a) a polypeptide comprising one or more protease cleavage sites, wherein the polypeptide is positioned between the N-terminal signal peptide and the polypeptide heterologous to the N-terminal signal peptide; (b) a polypeptide comprising a selectable marker; (c) a polypeptide comprising a visualization marker; (d) a polypeptide comprising a protein recognition/purification domain; or (e) a polypeptide comprising a flexible linker element, which connects the N-terminal signal peptide and the polypeptide heterologous to the N-terminal signal peptide.

In yet another embodiment, the *Paenibacillus* endospore is an endospore formed by a *Paenibacillus* species, comprising: *Paenibacillus* sp. NRRL B-50972, *Paenibacillus* terrae, *Paenibacillus polymyxa*, or *Paenibacillus peoriae*; or an endospore formed by a bacterium that possesses a 16S rRNA gene that shares at least 97, 98 or 99% identity with a 16S rRNA gene of a *Paenibacillus* species.

In one aspect, the nucleic acid molecule is operatively linked to a promoter element that is heterologous to at least one of the second polynucleotide sequences and *Paenibacillus*.

In another aspect, the first polynucleotide sequence comprises: a codon-optimized polynucleotide sequence having at least 50%, 60%, 70%, 80% or 90% sequence identity with SEQ ID NO: 1, 3, 5, 7, 9, 19, 23, 25, 27, or 29; or a fragment thereof, which is expressed at a higher rate or level in the *Paenibacillus* endospore compared to the corresponding unoptimized sequence under identical conditions.

In yet another aspect, the present invention relates to a fusion protein comprising an N-terminal signal peptide operably linked to a polypeptide heterologous to the N-terminal signal peptide, wherein the N-terminal signal peptide comprises: (i) a polypeptide comprising at least 15, 30, 45, 60, 75, 90, 105, or 115 residues; (ii) a polypeptide comprising an amino acid sequence having at least 50%, 60%, 70%, 80%, or 90% sequence identity with the amino acid sequence of SEQ ID NO: 2, 4, 6, 8, 10, 18, 20, 21, 22, 24, 26, 28, 30, 31, or 32; or (iii) a polypeptide comprising a fragment of at least 15, 30, 45, 60, 75, 90, 105, or 115 consecutive amino acids of SEQ ID NO: 2, 4, 6, 8, 10, 18, 20, 21, 22, 24, 26, 28, 30, 31, or 32; wherein the N-terminal signal peptide is capable of targeting the fusion protein to the spore surface of a *Paenibacillus* endospore.

In one embodiment, the fragment starts at the first amino acid of SEQ ID NO: 2, 4, 6, 8, 10, 18, 20, 21, 22, 24, 26, 28, 30, 31, or 32. In another embodiment, the polypeptide sequence comprises a sequence having at least 50%, 60%, 70%, 80% or 90% sequence identity with SEQ ID NO: 2, 8, 20, 21, 22, 28, 31, or 32. In yet another embodiment, the fragment comprises amino acids 1-15, or 1-30, 1-45, 1-60, 1-75, 1-90, 1-105, or 1-115 of SEQ ID NO: 2, 8, 31, or 32.

In some aspects, the polypeptide heterologous to the N-terminal signal peptide comprises: (a) a plant growth-stimulating protein; (b) an enzyme; (c) a protein; (d) a polypeptide heterologous to *Paenibacillus*; (e) a therapeutic protein; or (f) a plant immune-stimulating protein.

In other aspects, the fusion protein further comprises: (a) a polypeptide containing one or more protease cleavage sites, positioned between the N-terminal signal peptide and the polypeptide heterologous to the N-terminal signal peptide; (b) a polypeptide comprising a selectable marker; (c) a polypeptide comprising a visualization marker; (d) a polypeptide comprising at least one protein recognition/purification domain; or (e) a polypeptide comprising a flexible linker element, connecting the signal peptide and the polypeptide heterologous to the N-terminal signal peptide.

In some embodiments, the present invention provides a recombinant *Paenibacillus* cell comprising a bacterial chromosome comprising a nucleic acid molecule disclosed herein.

In other embodiments, the present invention relates to a vector comprising a nucleic acid molecule disclosed herein, wherein the vector comprises a plasmid, an artificial chromosome, or a viral vector. In one aspect, the vector further comprises at least one of the following: (a) an origin of replication that provides stable maintenance in a *Paenibacillus* cell; (b) an origin of replication that provides selectively non-stable maintenance in a *Paenibacillus* cell; (c) a temperature-sensitive origin of replication that provides selectively non-stable maintenance in a *Paenibacillus* cell; (d) a polynucleotide encoding a selection marker, operably linked to an expression control sequence; or (e) a polynucleotide encoding a plant growth stimulating protein, operably linked to an expression control sequence.

In yet other embodiments, the present invention provides a recombinant *Paenibacillus* cell transformed with a vector comprising a nucleic acid molecule disclosed herein. In one aspect, the the recombinant *Paenibacillus* cell is a *Paenibacillus* species, comprising: *Paenibacillus* sp. NRRL B-50972, *Paenibacillus terrae, Paenibacillus polymyxa*, or *Paenibacillus peoriae*; or a bacterium that possesses a 16S rRNA gene that shares at least 97, 98 or 99% identity with a 16S rRNA gene of a *Paenibacillus* species.

In some aspects, the present invention provides a method of displaying a heterologous fusion protein on a spore surface of a *Paenibacillus* endospore, the method comprising: a) transforming a *Paenibacillus* cell capable of sporulation with a recombinant vector comprising a nucleic acid molecule disclosed herein; and b) expressing the fusion protein encoded by a nucleic acid molecule disclosed herein under sporulation conditions such that the fusion protein is targeted to the spore surface of the *Paenibacillus* endospore resulting from the sporulation, wherein the N-terminal signal peptide comprises: (i) a polypeptide comprising at least 5, 10, 15, 20, 25 or 30 residues; (ii) a polypeptide comprising an amino acid sequence having at least 50%, 60%, 70%, 80% or 90% sequence identity with the amino acid sequence of SEQ ID NO: 2, 4, 6, 8 or 10; or (iii) a fragment of at least 5, 10, 15, 20, 25 or 30 consecutive amino acids of SEQ ID NO: 2, 4, 6, 8 or 10.

In one embodiment, the present invention relates to a composition comprising: a) one or more recombinant endospore-producing *Paenibacillus* cells that express a fusion protein disclosed herein, wherein the polypeptide heterologous to the N-terminal signal peptide comprises a plant growth or immune stimulating protein; and b) at least one biological control agent; optionally, in a synergistically effective amount.

In yet another embodiment, the present invention provides a seed treated with a nucleic acid disclosed herein, a fusion protein disclosed herein, a recombinant bacterial cell disclosed herein, or a composition disclosed herein.

In one aspect, the present invention provides a method of treating a plant, a seed, a plant part, or the soil surrounding the plant to enhance plant growth and/or promote plant health comprising the step of simultaneously or sequentially applying: a) recombinant endospore-producing *Paenibacillus* endospores that express a fusion protein disclosed herein, wherein the polypeptide heterologous to the N-terminal signal peptide comprises a plant growth or immune stimulating protein; and b) at least one biological control agent; optionally, in a synergistically effective amount.

In another aspect, the present invention relates to a method of screening a host plant treated with a recombinant *Paenibacillus* endospore, comprising the following steps: a) applying a composition comprising a *Paenibacillus* endospore modified to express a fusion protein disclosed herein, to a seed, a seedling, or a vegetative plant capable of being permanently or transiently colonized by a *Paenibacillus*, to produce a treated seed, seedling, or vegetative plant; b) screening the treated seed, seedling, or vegetative plant by detecting and optionally measuring a trait, component, or attribute of the treated seed, seedling, or vegetative plant.

In some embodiments, the screening step comprises one or more of the following: a) at least one in vitro assay comprising detecting and optionally quantifying the presence, level, change in level, activity, or localization of one or more compounds contained in an extract prepared from a cell or tissue sample obtained from the treated seed, seedling, or vegetative plant; and/or b) at least one in vivo assay comprising detecting and optionally quantifying a trait, component, or attribute of the treated seed, seedling, or vegetative plant.

In one aspect, the present invention relates to a method of screening heterologous proteins or peptides expressed in a *Paenibacillus* cell for agriculturally-significant properties, comprising: a) modifying a *Paenibacillus* cell to express a fusion protein disclosed herein to produce a recombinant *Paenibacillus* cell; and b) screening the *Paenibacillus* cell by detecting and optionally quantifying a level or activity of a compound produced by the recombinant *Paenibacillus* cell.

Also provides is a method of treating a plant, a seed, a human, or an animal, comprising: administering to the plant, seed, human, or animal a composition comprising an endospore produced by a recombinant *Paenibacillus* cell; wherein the recombinant *Paenibacillus* cell expresses a fusion protein disclosed herein.

In some aspects, the composition has been heat-inactivated or sterilized such that no viable *Paenibacillus* cells remain.

In other aspects, the present invention relates to a composition comprising an isolated and/or purified fusion protein as disclosed herein.

In one embodiment, the present invention provides a method of delivering a protein of interest to a plant, seed or field, comprising: applying a composition comprising a recombinant *Paenibacillus* endospore to a plant, seed, or field; wherein the recombinant *Paenibacillus* endospore has been modified to express a fusion protein disclosed herein.

In certain aspects, the composition is applied to a field: a) pre- or post-planting; b) pre- or post-emergence; c) as a powder, suspension or solution; and/or d) wherein the composition further comprises one or more additional compounds that stimulate plant growth or protect plants from pests.

In a particular embodiment, the present invention relates to a method for identifying an N-terminal signal sequence that is capable of targeting a protein to a spore surface of an endospore-forming bacterium, comprising: screening a genome of the endospore-forming bacterium for at least one open reading frame which encodes a protein having multiple collagen-like triplet repeats having the sequence "GLY-X-X," wherein "X" represents "any amino acid"; and determining that at least one of the proteins identified in the screening step localizes to the spore surface of the endospore-forming bacterium by microscopy or experimentally.

In one aspect, the endospore-forming bacterium includes a hair-like structure that is proteolytically resistant. In another aspect, the method further comprises identifying a putative N-terminal signal sequence from at least one protein identified in the determining step as localizing to the spore surface and expressing in the endospore-forming bacterium a fusion protein comprising the putative N-terminal signal sequence and a reporter gene.

In another aspect, the method further comprises selecting the fusion protein based on expression of the fusion protein on the spore surface. In yet another aspect, the method further comprises replacing the reporter gene in the fusion protein that is selected with a nucleotide sequence of interest to create a second fusion protein and expressing the second fusion protein in the endospore-forming bacterium.

In some embodiments, the bacterium is a member of the genus *Paenibacillus, Viridibacillus, Brevibacillus* or *Lysinibacillus*. In one embodiment, the bacterium is a member of the genus *Paenibacillus*.

In some aspects, localization is determined using transmission electron microscopy or mass spectrometry.

In other aspects, the present invention relates to a nucleic acid molecule encoding an N-terminal signal peptide, wherein the signal peptide comprises: a) a contiguous segment of at least 5, 10, 15, 20, 25, 30, 35, 40, 45, 50, 60, 70, 80, 90, 100, 110, or 120 N-terminal residues of a protein determined to localize to a spore surface of an endospore-forming bacterium by a method disclosed herein; b) a sequence having at least 60%, 65%, 70%, 75%, 80%, 85%, 90%, or 95% sequence identity to a contiguous segment of at least 5, 10, 15, 20, 25, 30, 35, 40, 45, 50, 60, 70, 80, 90, 100, 110, or 120 N-terminal residues of a protein determined to localize to a spore surface of an endospore-forming bacterium by a method disclosed herein; wherein the segment or sequence is capable of targeting a fusion protein comprising the segment or sequence to the spore surface of an endospore-forming bacterium when expressed in the bacterium.

In yet other aspects, the present invention provides a nucleic acid molecule encoding a fusion protein, comprising (a) a first polynucleotide sequence encoding an N-terminal signal peptide, operably linked to (b) a second polynucleotide sequence encoding a polypeptide heterologous to the N-terminal signal peptide, wherein the first polynucleotide sequence comprises the sequence or segment disclosed herein and the N-terminal signal peptide is capable of targeting the fusion protein to the spore surface of a bacterial endospore.

In one aspect, the nucleic acid molecule further comprises an upstream regulatory sequence that causes transcription of the fusion protein during sporulation of a bacterial cell. In one embodiment, the bacterial cell is a *Paenibacillus* family member.

In some embodiments, the upstream regulatory sequence comprises: (a) any of SEQ ID NOs: 11-15; (b) a sequence comprising a fragment of at least 25, 50, 100, 150 contiguous nucleotides of any of SEQ ID NOs: 11-15; (c) a sequence having at least 60%, 70%, 80%, or 90% sequence identity compared to any of SEQ ID NOs: 11-15, or to a 25, 50, 100 or 150 nucleotide fragment thereof; wherein the upstream regulatory sequence comprises a promoter that is transcriptionally active during sporulation of the bacterial cell.

In yet other embodiments, the present invention provides a nucleic acid molecule encoding an upstream regulatory sequence and a protein of interest, comprising: (a) a first polynucleotide sequence encoding the upstream regulatory sequence, operably linked to (b) a second polynucleotide sequence encoding the protein of interest; wherein the protein of interest is heterologous to the upstream regulatory sequence and the upstream regulatory sequence causes transcription of the protein of interest during sporulation of a bacterial cell. In one aspect, the bacterial cell is a *Paenibacillus* family member.

In another aspect, the upstream regulatory sequence comprises: (a) any of SEQ ID NOs: 11-15; (b) a sequence comprising a fragment of at least 25, 50, 100, 150 contiguous nucleotides of any of SEQ ID NOs: 11-15; (c) a sequence having at least 60%, 70%, 80%, or 90% sequence identity compared to any of SEQ ID NOs: 11-15, or to a 25, 50, 100 or 150 nucleotide fragment thereof; wherein the upstream regulatory sequence comprises a promoter that is transcriptionally active during sporulation of the bacterial cell.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 depicts a local sequence alignment of the N-terminal portion of SEQ ID NO: 2 and SEQ ID NO: 8, which are exemplary spore surface-targeting sequences according to the disclosure. A consensus sequence (SEQ ID NO: 32) is shown below the alignment.

DETAILED DESCRIPTION

Figure 1:
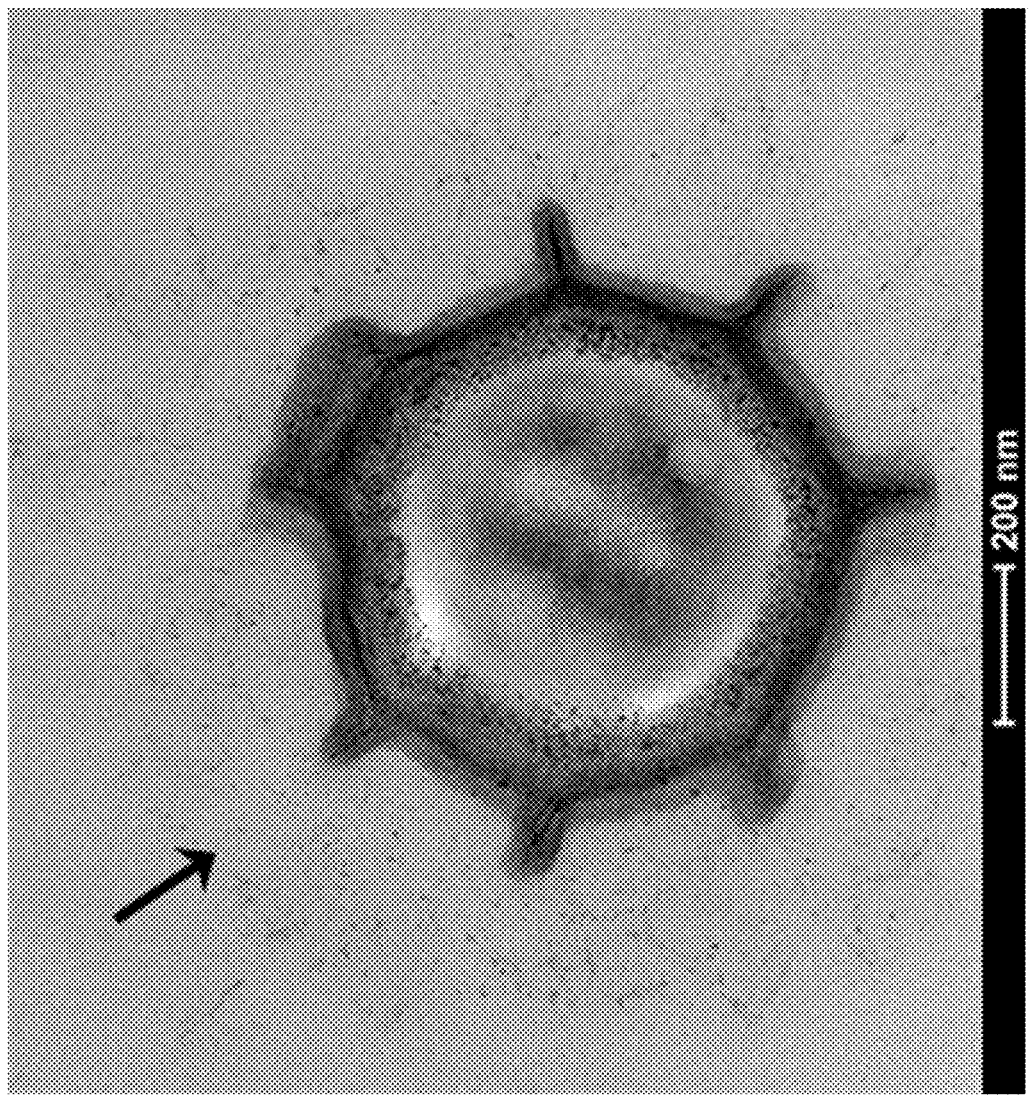
FIG. 1 depicts a transmission electron micrograph of a *Paenibacillus* sp. NRRL B-50972 endospore. Hair-like structures comprised of collagen-like protein are shown extending from the endospore surface and one such structure is denoted by an arrow.
Figure 2A:
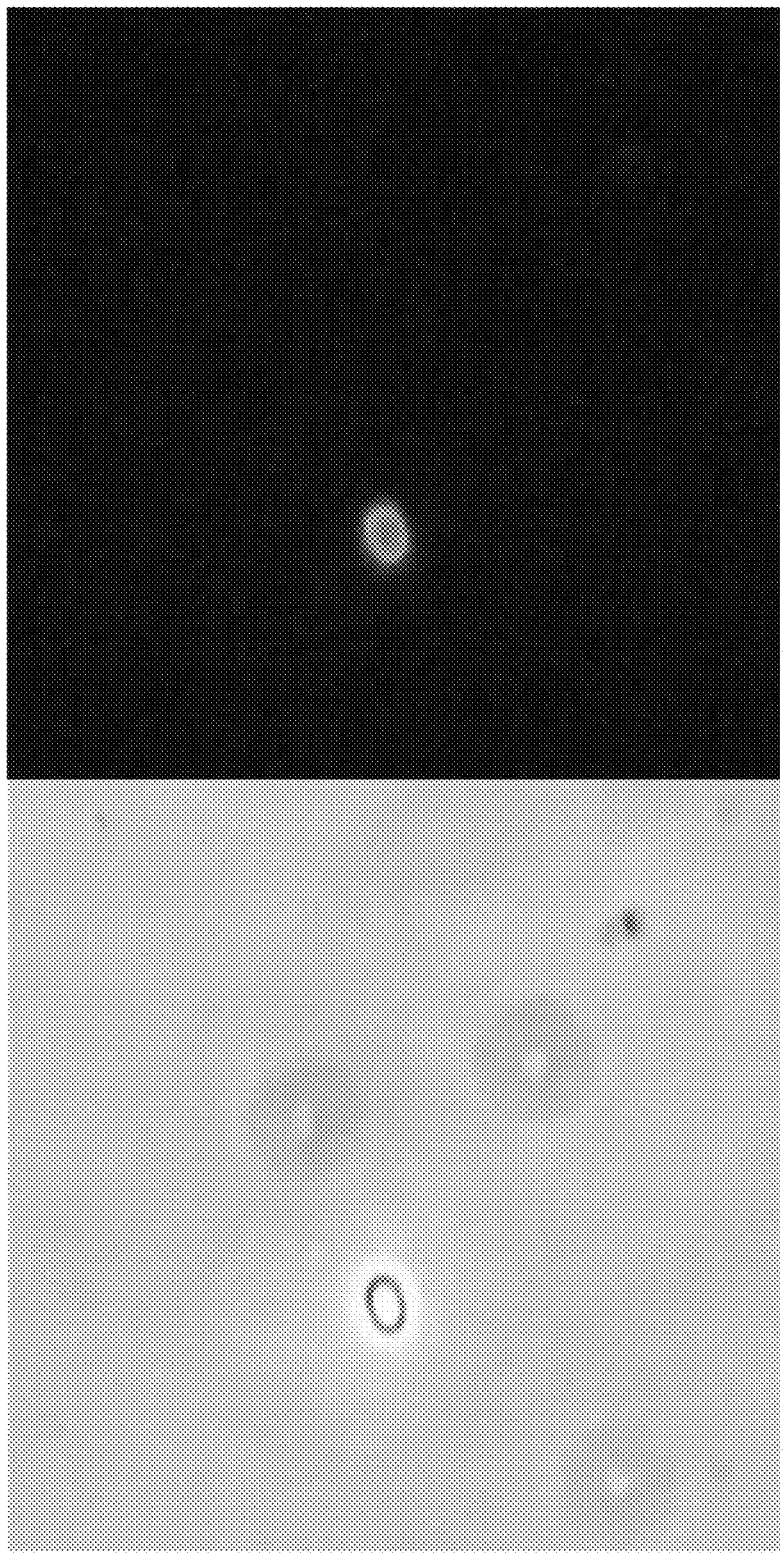
FIG. 2A depicts phase contrast (left) and epifluorescent (right) micrographs (1000× magnification) of a *Paenibacillus* sp. NRRL B-50972 endospore expressing an exemplary N-terminal targeting sequence according to the disclosure, specifically a (SEQ ID NO: 2)-GFP fusion protein construct which is localized to the endospore surface as shown by this figure. The fluorescence produced by the GFP protein in the right panel corresponds with the image of the cell observed with phase contrast microscopoy in the left panel indicating correct localization of the GFP to the endospore surface.
Figure 2B:
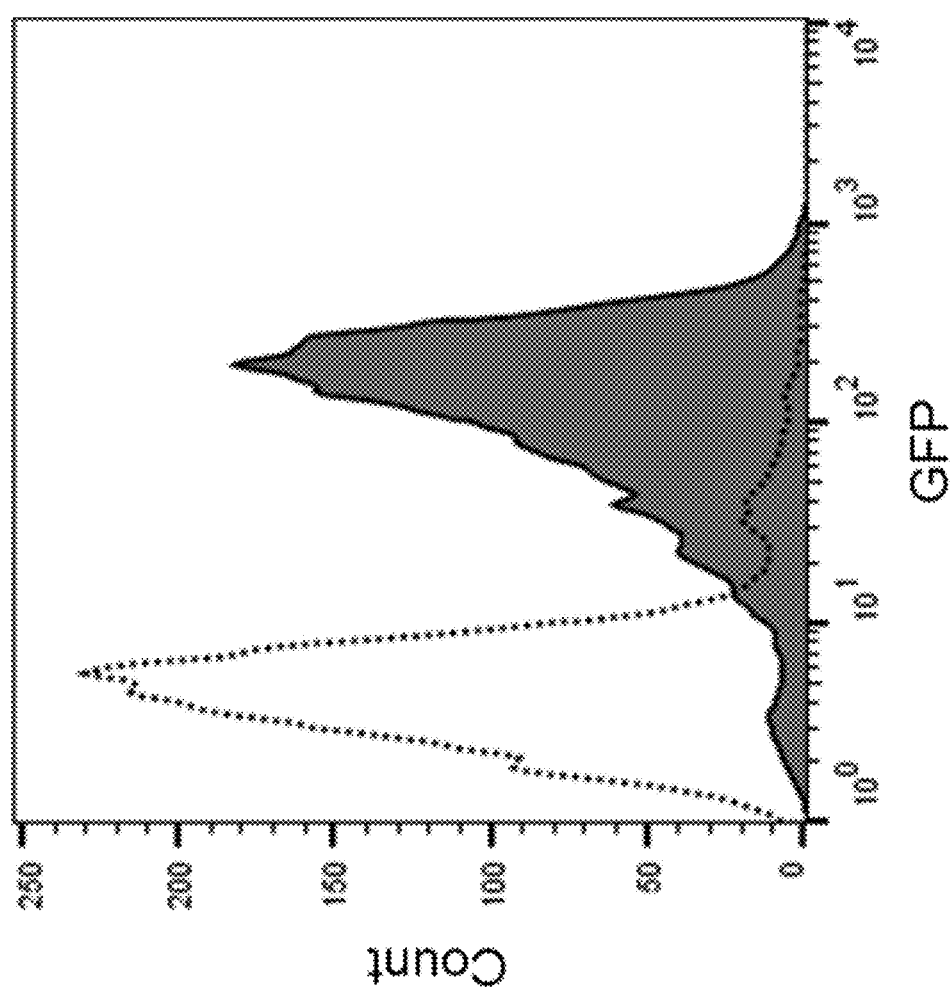
FIG. 2B depicts a flow cytometry histogram of *Paenibacillus* sp. NRRL B-50972 endospores expressing an exemplary N-terminal targeting sequence according to the disclosure, specifically a (SEQ ID NO: 2)-GFP fusion protein construct, which is localized to the endospore surface (shaded area). Wild-type *Paenibacillus* sp. NRRL B-50972 endospores with no observable GFP fluorescence are shown for comparison (open, dotted line area). 10,000 events are shown for each spore population on this figure.

The disclosure provides genetic constructs capable of targeting a fusion protein to a *Paenibacillus* spore surface, as well as compositions and methods that use these constructs to deliver heterologous molecules of interest (e.g., peptides, proteins) to various environments, such as plants. For example, following treatment with the recombinant *Paenibacillus* endospores, treated plants may be screened to detect changes attributable to the heterologous protein delivered via the *Paenibacillus* endospores. Such changes may include alterations in the host plant's growth rate or yield; enhanced plant health (e.g., resistance to environmental stress, disease or pests); and the display of enhanced, modified or otherwise new attributes, compared to host plants grown under the same conditions absent treatment with the recombinant *Paenibacillus* endospores. The use of a targeting sequence that efficiently targets the heterologous protein to the spore surface also provides a platform for high-throughput screening for useful heterologous proteins that, for example, are capable of enhancing, modifying, and/or conferring new plant traits or attributes.

The canonical spore formation process (elucidated based on studies using *B. subtilis*) involves asymmetric cell division of a vegetative cell to form a mother cell and a forespore, which develop as two distinct compartments separated by an intervening septum. Eventually, the peptidoglycan in the septum is degraded and the forespore is engulfed by the mother cell, forming a cell within a cell. Intercellular communication between the mother cell and forespore coordinates cell-specific gene expression in each cell, resulting in the production of endospore-specific compounds, formation of a cortex layer around the forespore and deposition of the coat.

In some Bacillus species, e.g., *B. subtilis, B. licheniformis*, and *B. pumilus*, this coat will go on to become the outermost layer of the endospore. The forespore undergoes a final dehydration and maturation into a complete endospore. The mother cell is subsequently degraded via programmed cell death, resulting in a release of the endospore into the environment. The endospore will then typically remain in a dormant state until more favorable conditions or particular stimuli trigger germination and a return to the vegetative state.

As the outermost surface between the spore and the environment, the coat layer serves many critical functions. In particular, this layer acts as a semipermeable barrier to environmental insults and mediates interactions with the surrounding environment, and thus plays an important role in maintaining the viability of the spore and in the sensing of conditions that trigger germination of the endospore. The coat layer is also a target of clinical research as it contains cell surface molecules in pathogenic strains of bacteria that contribute to host immune cell recognition. Methods of displaying heterologous proteins on the spore coat of *B. subtilis* have been developed using fusion protein constructs containing a *B. subtilis* spore coat protein such as CotC fused to a protein of interest. However, the spore surface proteins of *Paenibacillus* are unknown and thus studies using *B. subtilis* fail to provide guidance as to how fusion proteins may be targeted to the spore surface of other bacterial genera, such as *Paenibacillus*.

In contrast, the disclosure provides N-terminal constructs and fusion proteins comprising the same that are capable of targeting fusion protein constructs to the spore surface of *Paenibacillus* cells. The N-terminal signal sequence used to target the fusion protein to the spore surface may comprise a polypeptide having a sequence as represented by SEQ ID NO: 2, 4, 6, 8 or 10. Alternatively, in select embodiments, this N-terminal signal sequence may comprise a fragment or variant of SEQ ID NO: 2, 4, 6, 8 or 10 sufficient to retain the spore surface targeting functionality. For example, a fragment may comprise the first 10, 15, 20, 25 or 30 amino acids of SEQ ID NO: 2, 4, 6, 8 or 10. Further alternative aspects include N-terminal signal sequences encoded by a nucleic acid comprising the nucleotide sequence of SEQ ID NO: 1, 3, 5, 7 or 9, or a fragment or variant thereof. These and other embodiments are described herein.

Throughout the disclosure, the term "comprise" or any derivative thereof (e.g., comprising, comprises) may be replaced with "consist essentially of," "consist of," or the applicable corresponding derivative thereof.

As used herein, "*Paenibacillus*" refers to endospore-producing bacteria classified in the *Paenibacillus* genus. This term encompasses, without limitation, various *Paenibacillus* family members including *Paenibacillus* sp. NRRL B-50972, *Paenibacillus abyssi, Paenibacillus aceti, Paenibacillus aestuarii, Paenibacillus agarexedens, Paenibacillus agaridevorans, Paenibacillus alginolyticus, Paenibacillus algorifonticola, Paenibacillus alkaliterrae, Paenibacillus alvei, Paenibacillus amylolyticus, Paenibacillus anaericanus, Paenibacillus antarcticus, Paenibacillus apiarius, Paenibacillus arachidis, Paenibacillus assamensis, Paenibacillus azoreducens, Paenibacillus azotofixans,*

*Paenibacillus baekrokdamisoli, Paenibacillus barcinonensis, Paenibacillus barengoltzii, Paenibacillus borealis, Paenibacillus bovis, Paenibacillus brasilensis, Paenibacillus camelliae, Paenibacillus campinasensis, Paenibacillus castaneae, Paenibacillus catalpae, Paenibacillus cathormii, Paenibacillus cavernae, Paenibacillus cellulosilyticus, Paenibacillus cellulositrophicus, Paenibacillus chartarius, Paenibacillus chibensis, Paenibacillus chinjuensis, Paenibacillus chitinolyticus, Paenibacillus chondroitinus, Paenibacillus chungangensis, Paenibacillus cineris, Paenibacillus cisolokensis, Paenibacillus contaminans, Paenibacillus cookii, Paenibacillus cucumis, Paenibacillus curdlanolyticus, Paenibacillus daejeonensis, Paenibacillus darwinianus, Paenibacillus dauci, Paenibacillus dendritiformis, Paenibacillus dongdonensis, Paenibacillus doosanensis, Paenibacillus durus, Paenibacillus edaphicus, Paenibacillus ehimensis, Paenibacillus elgii, Paenibacillus endophyticus, Paenibacillus etheri, Paenibacillus faecis, Paenibacillus favisporus, Paenibacillus ferrarius, Paenibacillus filicis, Paenibacillus fonticola, Paenibacillus forsythias, Paenibacillus frigoriresistens, Paenibacillus gansuensis, Paenibacillus gelatinilyticus, Paenibacillus ginsengarvi, Paenibacillus ginsengihumi, Paenibacillus ginsengisoli, Paenibacillus glacialis, Paenibacillus glucanolyticus, Paenibacillus glycanilyticus, Paenibacillus gordonae, Paenibacillus graminis, Paenibacillus granivorans, Paenibacillus guangzhouensis, Paenibacillus harenae, Paenibacillus hemerocallicola, Paenibacillus hispanicus, Paenibacillus hodogayensis, Paenibacillus hordei, Paenibacillus humicus, Paenibacillus hunanensis, Paenibacillus illinoisensis, Paenibacillus jamilae, Paenibacillus jilunlii, Paenibacillus kobensis, Paenibacillus koleovorans, Paenibacillus konsidensis, Paenibacillus koreensis, Paenibacillus kribbensis, Paenibacillus kyungheensis, Paenibacillus lactis, Paenibacillus larvae, Paenibacillus larvae, Paenibacillus larvae, Paenibacillus lautus, Paenibacillus lemnae, Paenibacillus lentimorbus, Paenibacillus lentus, Paenibacillus liaoningensis, Paenibacillus lupini, Paenibacillus macerans, Paenibacillus macquariensis, Paenibacillus macquariensis, Paenibacillus macquariensis, Paenibacillus marchantiophytorum, Paenibacillus marinisediminis, Paenibacillus massiliensis, Paenibacillus medicaginis, Paenibacillus mendelii, Paenibacillus methanolicus, Paenibacillus montaniterrae, Paenibacillus motobuensis, Paenibacillus mucilaginosus, Paenibacillus nanensis, Paenibacillus naphthalenovorans, Paenibacillus nasutitermitis, Paenibacillus nematophilus, Paenibacillus nicotianae, Paenibacillus oceanisediminis, Paenibacillus odorifer, Paenibacillus oenotherae, Paenibacillus oryzae, Paenibacillus pabuli, Paenibacillus panacisoli, Paenibacillus panaciterrae, Paenibacillus pasadenensis, Paenibacillus pectinilyticus, Paenibacillus peoriae, Paenibacillus periandrae, Paenibacillus phoenicis, Paenibacillus phyllosphaerae, Paenibacillus physcomitrellae, Paenibacillus pini, Paenibacillus pinihumi, Paenibacillus pinesoli, Paenibacillus pocheonensis, Paenibacillus polymyxa, Paenibacillus popilliae, Paenibacillus populi, Paenibacillus prosopidis, Paenibacillus provencensis, Paenibacillus pueri, Paenibacillus puldeungensis, Paenibacillus pulvifaciens, Paenibacillus purispatii, Paenibacillus qingshengii, Paenibacillus quercus, Paenibacillus radicis, Paenibacillus relictisesami, Paenibacillus residui, Paenibacillus rhizoryzae, Paenibacillus rhizosphaerae, Paenibacillus rigui, Paenibacillus riograndensis, Paenibacillus ripae, Paenibacillus sabinae, Paenibacillus sacheonensis, Paenibacillus salinicaeni, Paenibacillus sanguinis, Paenibacillus sediminis, Paenibacillus segetis, Paenibacillus selenii, Paenibacillus selenitireducens, Paenibacillus senegalensis, Paenibacillus septentrionalis, Paenibacillus sepulcri, Paenibacillus shenyangensis, Paenibacillus shirakamiensis, Paenibacillus siamensis, Paenibacillus silagei, Paenibacillus sinopodophylli, Paenibacillus solani, Paenibacillus soli, Paenibacillus sonchi, Paenibacillus sophorae, Paenibacillus sputi, Paenibacillus stellifer, Paenibacillus susongensis, Paenibacillus swuensis, Paenibacillus taichungensis, Paenibacillus taiwanensis, Paenibacillus tarimensis, Paenibacillus telluris, Paenibacillus terrae, Paenibacillus terreus, Paenibacillus terrigena, Paenibacillus thailandensis, Paenibacillus thermophilus, Paenibacillus thiaminolyticus, Paenibacillus tianmuensis, Paenibacillus tibetensis, Paenibacillus timonensis, Paenibacillus tundrae, Paenibacillus turicensis, Paenibacillus typhae, Paenibacillus uliginis, Paenibacillus urinalis, Paenibacillus validus, Paenibacillus vini, Paenibacillus vulneris, Paenibacillus wenxiniae, Paenibacillus wooponensis, Paenibacillus woosongensis, Paenibacillus wulumuqiensis, Paenibacillus wynnii, Paenibacillus xanthinilyticus, Paenibacillus xinjiangensis, Paenibacillus xylanexedens, Paenibacillus xylanilyticus, Paenibacillus xylanisolvens, Paenibacillus yonginensis, Paenibacillus yunnanensis, Paenibacillus zanthoxyli,* and *Paenibacillus zeae.*

In certain aspects, the *Paenibacillus* member used to express the fusion protein is *Paenibacillus* sp. NRRL B-50972, a Gram-positive, aerobic, and spore-forming bacterium isolated from soil. A sample of *Paenibacillus* sp. NRRL B-50972 has been deposited with the Agricultural Research Service Culture Collection located at the National Center for Agricultural Utilization Research, Agricultural Research Service, U.S. Department of Agriculture (NRRL), 1815 North University Street, Peoria, Ill. 61604, U.S.A., under the Budapest Treaty on Aug. 28, 2014. Given the general lack of knowledge about the basic composition or structure of the *Paenibacillus* spore, little is known about the process by which proteins are targeted to the spore surface during formation of this layer.

In certain aspects, the *Paenibacillus* member used to express the fusion protein is a bacterium that possesses a 16S rRNA gene that shares at least 97, 98 or 99 percent identity with a 16S rRNA gene of *Paenibacillus* sp. NRRL B-50972 or any of the other exemplary *Paenibacillus* family members disclosed herein. Alternatively, the *Paenibacillus* member used to express the fusion protein is a bacterium that possesses a DNA-DNA hybridization value of at least 70 percent to that of *Paenibacillus* sp. NRRL B-50972 or any of the other exemplary *Paenibacillus* family members disclosed herein. In another instance, the *Paenibacillus* member used to express the fusion protein is a bacterium that possesses an average nucleotide identity of 95, 96, 97, 98, or 99 percent to that of *Paenibacillus* sp. NRRL B-50972 or any of the other exemplary *Paenibacillus* family members disclosed herein.

The term "N-terminal signal sequence" generally refers to a polypeptide sequence located at or proximal to the amino terminus of a polypeptide, which directs localization of the polypeptide to a subcellular compartment, or for secretion. It is recognized and understood that this term may be used interchangeably with the terms "N-terminal targeting sequence," "targeting sequence," "signal sequence," and "signal peptide," depending on context. The N-terminal signal sequence may be retained as part of the polypeptide sequence of a mature protein or alternatively cleaved during or after the localization process. This term may be used to specifically refer to a polypeptide sequence located at or proximal to the amino terminus of a polypeptide, which directs localization of the polypeptide to the spore surface of a *Paenibacillus* endospore. In this context, the only required functionality of the N-terminal signal sequence is the capability to target the polypeptide of which it is a part to the spore surface of a *Paenibacillus* endospore.

A "plant" or "host plant," includes any plant that possesses a rhizosphere or phyllosphere which *Paenibacillus* can colonize, as well as plants that can serve as a transient hosts for *Paenibacillus* bacteria. Colonization is not a requirement for the methods described herein and compositions to function, though it may be preferred in certain aspects of the disclosure.

As used herein, "biological control" is defined as control of a pathogen and/or insect and/or an acarid and/or a nematode by the use of a second organism or a biological molecule. Known mechanisms of biological control include bacteria that control root rot by out-competing fungi for space or nutrients on the surface of the root. Bacterial toxins, such as antibiotics, have been used to control pathogens. The toxin can be isolated and applied directly to the plant or the bacterial species may be administered so it produces the toxin in situ. Other means of exerting biological control include the application of certain fungi producing ingredients active against a target phytopathogen, insect, mite or nematode, or attacking the target pest/pathogen. "Biological control" may also encompass microorganisms having a beneficial effect on plant health, growth, vigor, stress response or yield. Application routes include spray application, soil application and seed treatment.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner The complex may comprise two strands forming a duplex structure, three or more strands forming a multi-stranded complex, a single self-hybridizing strand, or any combination of these. Hybridization reactions can be performed under conditions of different "stringency". In general, a low stringency hybridization reaction is carried out at about 40° C. in 10× SSC or a solution of equivalent ionic strength/temperature. A moderate stringency hybridization is typically performed at about 50° C. in 6× SSC, and a high stringency hybridization reaction is generally performed at about 60° C. in 1× SSC.

As used herein, the term "sequence identity" refers to the degree to which two polynucleotide or amino acid sequences are identical (i.e., on a nucleotide-by-nucleotide or residue-by-residue basis, respectively) over the window of comparison. The percentage of sequence identity is calculated by comparing two optimally aligned sequences over the window of comparison, determining the number of positions at which the identical nucleic acid base (e.g., A, T, C, G for a polynucleotide sequence) occurs in both sequences to yield the number of matched positions, dividing the number of matched positions by the total number of positions in the window of comparison (i.e., the window size), and multiplying the result by 100 to yield the percentage of sequence identity. An equivalent calculation can be performed by comparing two aligned amino acid sequences.

With respect to the comparison of amino acid sequences, in addition to the measurement of sequence identity, a comparison may also take into account whether residue changes constitute "conservative" substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine

N-Terminal Targeting Sequences

The disclosure provides N-terminal targeting sequences from *Paenibacillus* bacteria. Under stressful environmental conditions, *Paenibacillus* family bacteria undergo sporulation and form endospores that can stay dormant for extended periods of time. As described in detail herein, the outermost layer of *Paenibacillus* endospores is known as the spore surface and comprises a protein layer. Despite the growing body of literature available regarding *Bacillus* spore surface targeting sequences, there are no reported studies identifying homologous N-terminal targeting sequences in Paenibacillus. A bioinformatics analysis of the known spore surface-targeted proteins CotC, Bc1A, Bc1B or BetA fails to reveal any homologous N-terminal targeting sequences in *Paenibacillus*, suggesting that the spore surface targeting sequences of these proteins is not conserved in the *Paenibacillus* genus. Given the limited characterization of proteins that form and localize to the spore surface of *Paenibacillus*, one cannot easily deduce the N-terminal signal sequences necessary to target proteins to the spore surface in *Paenibacillus* generally or in particular species within this genus (e.g., *Paenibacillus* sp. NRRL B-50972).

Despite this lack of guidance in the available literature, the inventors have identified N-terminal targeting sequences capable of directing endogenous and fusion proteins to the spore surface of *Paenibacillus* cells.

For ease of reference, the SEQ ID NOs. for the nucleotide and polypeptide sequences referred to herein are listed in Table 1 below.

TABLE 1

Exemplary *Paenibacillus* N-Terminal Targeting Sequences (i.e., SEQ ID NOs: 1-10 and 18) and upstream regulatory sequences (i.e., SEQ ID NOs: 11-15).

| Sequence Identifier | Sequence |
|---|---|
| SEQ ID NO: 1 | ATGGTAGTATTATCTACTGGACCTATTGCAAACGATCCTGTTCTAGGAGTCAGACCCACCCAACTGGTCACAGTAA AAATAGATAACCGAGATTCTGTAAATTCTTCTATCGTTTTGATCGAGGGTTTTATTTTAAACGGTAGCAGAACATT ATATGTACAACAATTAGTGGTAGTGGGACCAAATGCGGTTATAACGAGGAATTTCTTTGCAAATGTAGACGCATTT GAATTCGTTTTTACCACTAGCGGACCAGCAGAGAATGAAACTCAAATTTCTGTTTGGGGTAAAGATGCATTGGGGC AATTAGTACCTGCCCATCGGTTAGTATCTGACGAACTTTTAGGAACCGATCGA |

TABLE 1-continued Exemplary *Paenibacillus* N-Terminal Targeting Sequences (i.e., SEQ ID NOs: 1-10 and 18) and upstream regulatory sequences (i.e., SEQ ID NOs: 11-15).

| Sequence Identifier | Sequence |
|---|---|
| SEQ ID NO: 2 | MVVLSTGPIANDPVLGVRPTQLVTVKIDNRDSVNSSIVLIEGFILNGSRTLYVQQLVVVGPNAVITRNFFANVDAF EFVFTTSGPAENETQISVWGKDALGQLVPAHRLVSDELLGTDR |
| SEQ ID NO: 3 | ATGCCTGCCTTGGATGAATGGAGTAGTATACAACAAATCGATATGGAGGTGTTTGTATTGGGTCGTCCCGAATTGA AACGAAAGAAAGGCCGTAAAAAAGACGTTTTTATCCGCTCTTGGTTTAGTAAAAAACGTCCGAAGAGAAAATGCCA TTCGAAACGAAAGTGCTTTTGCAAGGAAATCGTCGTCAGAAAGCAAATCGTCCGTGTAAATATACCTCAAAATGTT TTA |
| SEQ ID NO: 4 | MPALDEWSSIQQIDMEVFVLGRPELKRKKGRKKDVFIRSWFSKKRPKRKCHSKRKCFCKEIVVRKQIVRVNIPQNV L |
| SEQ ID NO: 5 | ATGAAACACAGAAAACCGTTCAGGTTCAGTGGTGCTTCAAAAAAAGACGAGGACTGCAAACCACCTAAAATTAGCA GAGAAACGGAAGAACTTCTCAAACTGATTAAGGAATTAGTCGCCATCATCCCGCTCGTTTTCGCAAACCCGTCTGT GGCTAATGTAACTTCATTGCAACAGATTTTACAGCGATTATTAGCTCTCGCAAATAAATTGAGACTTAGAGGCTCG GCTAAGACAGATTTATTAGCGGCGTTGGAACTGGCTATCGTGGCGTCGGAAGCCACTCTTTTCTCCCCGATCGGTG TTGGAACGACACTGCAACAACTGCTGGAAGTCTTATTGTCTATTATTTTGCAGGAACCCCTTGATCCTGCTCTTAA AGACAGTTTGATCAGTGCAATCAGAAATGCCGAAACGGCTATCAGTATTGCGTTGGGT |
| SEQ ID NO: 6 | MKHRKPFRFSGASKKDEDCKPPKISRETEELLKLIKELVAIIPLVFANPSVANVTSLQQILQRLLALANKLRLRGS AKTDLLAALELAIVASEATLFSPIGVGTTLQQLLEVLLSIILQEPLDPALKDSLISAIRNAETAISIALG |
| SEQ ID NO: 7 | ATGGCGGTTATATCAACTGGACCCATAGAAAATAATTATGTCAGTGGTATTCGGCCTACTCATCGAGTTACCGTGA AAATTGATAATCGTGATACTGTGAATTCTTCTACGGTATTGATTCAGGGTTTTTATCTAAATGGTACAAGAACGTT ATATGTGCTTGATTTTATAACTGTAAATTCAAATGAAGTGATTACAAAAGATTATTATGCTGATTTTAATTCATTT GAGTTTGTTTTTACCACTGAAAGTGTTACAGAAAATGAGATTCAAGTTTCAGTCTGGGGTAAAAATTCAATGGGGC AGTTAGTGACAGCTCACCGTGTTGTATCTTCCGAATTGCTTGTAGCAAAAGGCGCG |
| SEQ ID NO: 8 | MAVISTGPIENNYVSGIRPTHRVTVKIDNRDTVNSSTVLIQGFYLNGTRTLYVLDFITVNSNEVITKDYYADFNSF EFVFTTESVTENEIQVSVWGKNSMGQLVTAHRVVSSELLVAKGA |
| SEQ ID NO: 9 | TTGGGAAATTTATTGTTGCGTAAAAGATATCGCTTGACCCAGGTGGCAAGGAAAAAAAAGAAGGAAAGAGATCAAA AGATGGGAGCGTTCCGTTTTATGCCCATTTATCGTACAGGAACGAGCTGCATTCGTAACAAAAAGGGAAATAAACG TATTTATAGACAGGGTAGAAGAAGAGAGAGAATATGCGCTTATAGACATCATTTGCACGCTGAGCGGGTGCCCTCA GGTTTATCAAATAAAAAAATCTGTTTTATGAAATTCAAAGGTCAACGAAGACTGCGAGGCGGCGAACAGGAGCCTC AAGGCAATTCAGGAGGAGCAGTTCAA |
| SEQ ID NO: 10 | LGNLLLRKRYRLTQVARKKKKERDQKMGAPRFMPIYRTGTSCIRNKKGNKRIYRQGRRRERICAYRHHLHAERVPS GLSNKKICFMKFKGQRRLRGGEQEPQGNSGGAVQ |
| SEQ ID NO: 18 | MGNLLLRKRYRLTQVARKKKKERDQKMGAFRFMPIYRTGTSCIRNKKGNKRIYRQGRRRERICAYRHHLHAERVPS GLSNKKICFMKFKGQRRLRGGEQEPQGNSGGAVQ |
| SEQ ID NO: 11 | GAAACGGGAGTGGTGAAATCATTGATGCTCAGCGCATTGTTGCGGATGAGCAACTAGATTCTTGAAACACAACATA TGTACAGAGATAGAACCACAATCGTAACAAATGGTTGAGACATAAAATAGAGGGAACAGGATCTTGAGAAAGATCT CATTGTTCACAAAAAAGCTTGATTTTACTAGAAAGGAGGGAGTATCCA |
| SEQ ID NO: 12 | CTATATACATGCGCAAAAAACGGCTTCAAACTGCTTCATAATTACGGCACGTTTCTTCTGGCGCCTTCGGCTGTTC CTTGGTGTGAACCAAGGTAACAGCCGGGGGCGCTATTTTTATATAACTAGATGAATGTACCTGTACAAAGACCCAT TTTTATCCAAAATTAGATCATTGCCTATCAACCACAGGACAGATGTCC |
| SEQ ID NO: 13 | AGCGTTACAAGTTGGAAGCCCGGTTTGGAAATACAGAAAATCGATATTAAAGCTTATGTACAAGCATCCAATAATA ATTCTTGTGTGGTGATTCACCCTTTTCGCTTCAGTAAATATATTGTTAATATCTGCGAAACGGGGCGATGATCCAC CTGTCACCTCTACAGTAGGGAGAAATGTGAAGGAGGAGATATTTGAAC |
| SEQ ID NO: 14 | AGCGGTATTTTTTGTGCCCCACAAAAAAGGCTCCCTTATCAAAAGGGGTTTTTATCACATAGGAAATGTCCACACG TATATATAGATGTTACATATTATATAAATCGTGAACATTCGAATCTCAATACTAGTTATAGAAGAGGTGGCATTAG TGATAGGATTATAGCTTCGTTACTTTAGACAAAAGGAGAATCCAATAT |
| SEQ ID NO: 15 | ATTTATTTTTTTGAAAAATTACAGGGGATTCAGTCCCACTTTCAGTAAATTCAGAAAGAAAAATAATGTAACGGCG AAATGGAAGTGAGCATTAAAAATTTATTTTTTTGGAAAAAAATTTAAGGAGGTCATCTGTCCAATCAGGTTCGTTT AGATTCCATAAGATAATGAAACTGTACTTAATTATGGAGGTGTCAGTA |

TABLE 2

Additional Exemplary *Paenibacillus* N-Terminal Targeting Sequences

| Sequence Identifier | Sequence |
|---|---|
| SEQ ID NO: 19 | ATGGTAGTATTATCTACTGGACCTATTGCAAACGATCCTGTTCTAGGAGTCAGACCCACCCAACTGGTCACAGTA
AAAATAGATAACCGAGATTCTGTAAATTCTTCTATCGTTTTGATCGAGGGTTTTATTTTAAACGGTAGCAGAACA
TTATATGTACAACAATTAGTGGTAGTGGGACCAAATGCGGTTATAACGAGGAATTTCTTTGCAAATGTAGACGCA
TTTGAATTCGTTTTTACCACTAGCGGACCAGCAGAGAATGAAACTCAAATTTCTGTTTGGGGTAAAGATGCATTG
GGGCAATTAGTACCTGCCCATCGGTTAGTATCTGACGAACTTTTAGGAACCGATCGAGGAATCCAAGGACCTCAA
GGAGTTCAGGGAGCCCAAGGCGACCAAGGTGACCAAGGACCTCAGGGTGTTCAAGGACCTCAAGGAGTTCAGGGA
GCCCAAGGAGACCAAGGAGTTCAAGGCGTACAAGGAGACCAAGGACCTCAAGGAGTCCAAGGCGACCAAGGTGAC
CAAGGACCTCAAGGAGTTCAAGGAGCGCAAGGTGACCAAGGCCCTCAAGGAGTTCAGGGAGCCCAAGGTGACCAA
GGACCTCAAGGCGTTCAGGGAGCGCAAGGTGACCAAGGACCTCAAGGTGATCAAGGACCTCAGGGAGTTCAAGGA
GACCAAGGCGATCAAGGACCACAGGGAGTTCAAGGCGTACAAGGTGATCAAGGACCTCAGGGTGTTCAAGGAGAC
CAAGGCGACCAAGGACCTCAGGGTGTTCAAGGCGTACAAGGTGACCAAGGACCTCAGGGTGTTCAAGGCGTACAA
GGTGACCAAGGACCTCAGGGAGTTCAAGGAGACCAAGGCGATCAAGGACCACAGGGAGTTCAAGGCGTACAAGGT
GATCAAGGACCTCAGGGTGTTCAAGGAGACCAAGGCGACCAAGGACCTCAGGGTGTTCAAGGCGTACAAGGTGAC
CAAGGACCTCAGGGTGTTCAAGGCGTACAAGGTGACCAAGGACCTCAGGGTGTTCAAGGCGTACAAGGTGACCAA
GGACCTCAAGGAGTTCAGGGAGCCCAAGGTGACCAAGGACCACAGGGAGTTCAAGGCGACCAAGGACCTCAAGGA
CCTCAAGGAGTTCAAGGTGACCAAGGACCTCAGGGCGTTCAAGGATCCCAAGGTGATCAAGGACCTCAAGGAGTT
CAAGGCGTACAAGGACCTCAAGGAGTTCAAGGCGTACAAGGCGACCAAGGACCTCAAGGTGTTCAGGGAGCCCAA
GGCGACCAAGGCCCTCAAGGAGTTCAAGGAGTCCAAGGTGACCAAGGACCACAGGGAGTTCAAGGACCGCAAGGT
GACCAAGGACCACAGGGAGTTCAGGGAGTCCAAGGCGACCAAGGACCTCAAGGAGTCCAAGGCGACCAAGGTGAC
CAAGGACCTCAAGGAGTTCAAGGAGCGCAAGGTGACCAAGGCCCTCAAGGAGTTCAGGGAGCCCAAGGTGACCAA
GGACCTCAAGGCGTTCAGGGAGCGCAAGGTGACCAAGGACCTCAAGGTGATCAAGGACCTCAGGGAGTTCAAGGA
GACCAAGGCGATCAAGGACCACAGGGAGTTCAAGGCGTACAAGGTGATCAAGGACCTCAGGGTGTTCAAGGAGAC
CAAGGCGACCAAGGACCTCAGGGTGTTCAAGGCGTACAAGGTGACCAAGGACCTCAGGGTGTTCAAGGCGTACAA
GGTGACCAAGGACCTCAAGGTGTTCAAGGCGTACAAGGTGACCAAGGACCTCAAGGTGTTCAAGGAGCCCAAGGT
GACCAAGGACCACAGGGAGTTCAAGGCGACCAAGGACCTCAAGGACCTCAAGGAGTTCAAGGTGACCAAGGACCT
CAGGGCGTTCAAGGATCCCAAGGTGATCAAGGACCTCAAGGAGTTCAAGGCGTACAAGGACCTCAAGGAGTTCAA
GGCGTACAAGGCGACCAAGGACCTCAAGGTGTTCAGGGAGCCCAAGGCGACCAAGGCCCTCAAGGAGTTCAAGGA
GTCCAAGGCGACCAAGGACCACAGGGAGTTCAAGGACCGCAAGGTGACCAAGGACCACAGGGAGT TABLE 2-continued Additional Exemplary *Paenibacillus* N-Terminal Targeting Sequences

| Sequence Identifier | Sequence |
|---|---|
| SEQ ID NO: 22 | MVVLSTGPIANDPVLGVRPTQLVTVKIDNRDSVNSSIVLIEGFILNGSRTLYVQQLVVVGPNAVITRNFFANVDA<br>FEFVFTTSGPAENETQISVWGKDALGQLVPAHRLVSDELLGTDRGIQGPQGVQGAQGDQGDQGPQGVQGPQGVQG<br>AQGDQGVQGVQGDQGPQGVQGDQGDQGPQGVQGAQGDQGDQGPQGVQGAQGDQGPQGDQGPQGVQG<br>DQGDQGPQGVQGVQGDQGPQGVQGDQGDQGPQGVQGVQGDQGDQGPQGVQGVQGDQGPQGVQGAQG<br>DQGPQGVQGDQGPQGPQGVQGDQGPQGVQGAQGDQGPQGVQGVQGPQGVQGVQGDQGPQGVQGAQGDQGPQGVQG<br>VQGDQGPQGVQGAQGDQGPQGVQGVQGDQGPQGVQGDQGDQGPQGVQGAQGDQGPQGVQGAQGDQGPQGVQGAQG |
| SEQ ID NO: 23 | ATGCCTGCCTTGGATGAATGGAGTAGTATACAACAAATCGATATGGAGGTGTTTGTATTGGGTCGTCCCGAATTG<br>AAACGAAAGAAAGGCCGTAAAAAAGACGTTTTTATCCGCTCTTGGTTTAGTAAAAAACGTCCGAAGAGAAAATGC<br>CATTCGAAACGAAAGTGCTTTTGCAAGGAAATCGTCGTCAGAAAGCAAATCGTCCGTGTAAATATACCTCAAAAT<br>GTTTTAGGTATAACAGGCGCAACTGGAGCTATAGGTGTAGCAGGTAACGTAGGTGCAGCGGGCACTGTGGGTGCT<br>GCTGGAGCCGTCGGAACTGCGGGAAATGTCGGGGCTGCCGGTAATGTGGGTACTGCGGGCACCGTTGGGACTGCC<br>GGAAATGTAGGCGCAGCGGGGGCTGTGGGCACTGCGGGCGCTGTTGGAGCTGCGGGTGCGGTAGGACCAGTAGGT<br>CCCGTAGGTCCTGCGGGCATTCCAGGGGCAGTCGGTCCAGCAGGTCCTGCGGGCGTTGCAGGGGCGGTCGGTCCT<br>GTAGGTCCTGCGGGTGCGGTAGGTGCCACTGGGGCTACGGGTACCGCAGGAGCGACGGGGTCCACCGGGGCTACG<br>GGAGCTACAGGAACCGCAGGTGGAATAGCTCAGTTTGGTTATATCTACAACTTAGGATCCCGAGTCGTTCCAATA<br>GAAGCGGATGTCATTTTCGATACGAACGGTATACTTACACCTGGAATTACCCACGCTCCCGGCACTACGCAGATT<br>GCAGTTACCGATGCGGGGAACTATGAAGTTAACTTTTCAGTATCGGGTGTAGAGCCAGGCCAATTTGCCATATTT<br>ATCAATGGCACTCTGGCAGCAGGAACCATATACGGCTCAGGAGCTGGTACGCAGCAAAACACAGGGCAGGCCATC<br>CTCGCTCTAGCATCCGGTGATGTTCTTACCCTGCGAAATCATAGCTCTGCCGCTGCGGTTACCCTGCAAACCTTG<br>GCTGGAGGTACCCAAGCCAACGTAAACGCTTCTGTCGTTATCAAAAAATTAAGTTAG |
| SEQ ID NO: 24 | MPALDEWSSIQQIDMEVFVLGRPELKRKKGRKKDVFIRSWFSKKRPKRKCHSKRKCFCKEIVVRKQIVRVNIPQN<br>VLGITGATGAIGVAGNVGAAGTVGAAGAVGTAGNVGAAGNVTAGTVGTAGNVGAAGAVGTAGAVGAAGAVGPVG<br>PVGPAGIPGAVGPAGPAGVAGAVGPVGPAGAVGATGATGTAGATGSTGATGATGTAGGIAQFGYIYNLGSRVVPI<br>EADVIFDTNGILTPGITHAPGTTQIAVTDAGNYEVNFSVSGVEPGQFAIFINGTLAAGTIYGSGAGTQQNTGQAI<br>LALASGDVLTLRNHSSAAAVTLQTLAGGTQANVNASVVIKKLS |
| SEQ ID NO: 25 | ATGAAACACAGAAAACCGTTCAGGTTCAGTGGTGCTTCAAAAAAAGACGAGGACTGCAAACCACCTAAAATTAGC<br>AGAGAAACGGAAGAACTTCTCAAACTGATTAAGGAATTAGTCGCCATCATCCCGCTCGTTTTCGCAAACCCGTCT<br>GTGGCTAATGTAACTTCATTGCAACAGATTTTACAGCGATTATTAGCTCTCGCAAATAAATTGAGACTTAGAGGC<br>TCGGCTAAGACAGATTTATTAGCGGCGTTGGAACTGGCTATCGTGGCGTCGGAAGCCACTCTTTTCTCCCCCGATC<br>GGTGTTGGAACGACACTGCAACAACTGCTGGAAGTCTTATTGTCTATTATTTTGCAGGAACCCCTTTGATCCTGCT<br>CTTAAAGACAGTTTGATCAGTGCAATCAGAAATGCCGAAACGGCTATCAGTATTGCGTTGGGTGGCACGGCAGGA<br>ACCCCCGGTCCACAAGGGCCCGCTGGGCCTGCTGGTCCGGGCGGTGCTCCAGGGACCTGTCGGTGGACCAGGGCCG<br>GTGGGTGCGGCAGGACCCAGCAGGTCCAGTTGGACCTGCTGGTCCTGTCGGACCTGTCGGGGCTGCCGGACCTGTT<br>GGAGCCGCCGGACCTGTTGGAGCCGCCGGACCTATCGGCGCCGCTGGGCCGCTAGGCGCCGCCGGGCTGCTGGA<br>GCCACCGGGGCTACAGGAGCTACAGGCGCGCAGGACCTGCCGGGGGGGCTACCGGGGCCACGGGCGCCGTTGGA<br>GCCACAGGCGCTACGGGCGCAGCGGGGTCGCTGGGGCTACAGGAACTACGGGCACGGCGGGCGCTGTCGGAGCT<br>ACCGGGGCCACGGGCACGGCGGGGCCATTGGAGCTACCGGGGCCACAGGCACGGCGGGGCCGTCGGAGCTACC<br>GGGGCCACAGGCACGGCGGGCGCTGTCGGAGCTACCGGGGCCACAGGCTACAGCAGGGGTTACTGGAGCCACCGGT<br>TCGGGGGCAATCATTCCATTTGCTTCGGGTGGACCAGCAATTTTGACAACCATTGTCGGCGGGCTGGTTGGAACC<br>ACAAGTTTGATCGGCTTTGGAAGCTCAGCAACAGGCATTAGCCTTGTGGGTGGAACCATTGACCTGACAGGCACA<br>CTTGCAGGGCCACTGATTAACTTTGCTTTTTCTGTACCACGGGATGGCGTAATTACATCCATCGCTGGATATTT<br>AGTACAACAGCTGCGCTAACTCTCGTTGGATCAACCGCGACGATTACTGCCCAGTTGTTTAGTTCGACTACACCT<br>GATAACACCTTTACAGCGGTCCCTGGGGCTACCGTTACATTAGCTTCCACCACTGACTGGCATCATTGCCTTGGGT<br>ACCATTTCAATGGCATCACTACCGGATTGGCTATACCAGTAACCGCGCAGACTCGTCTGCTCCTTGTCTTCTCT<br>GCAACAGCTACGGGACTCTCCCTCGTAAACACCATCGTGGGTTATGCGAGCGCAGGCATTACCATCACCTGA |
| SEQ ID NO: 26 | MKHRKPPRFSGASKKDEDCKPPKISRETEELLKLIKELVAIIPLVFANPSVANVTSLQQILQRLLALANKLRLRG<br>SAKTDLLAALELAIVASEATLFSPIGVGTTLQQLLEVLLSIILQEPLDPALKDSLISAIRNAETAISIALGGTAG<br>TPGPQGPAGPAGPGGAPGPVGGPGPVGAAGPAGPVGPAGPVGPVGAAGPVGAAGPVGAAGPIGAAGPVGAAGAAG<br>ATGATGATGAAGPAGGATGGATGATGAVGATGATGAAGVAGATGTTGTAGAVGATGATGTAGAIGATGATGAVGAT<br>GATGTAGAVGATGATGTAGVTGATGSGAIIPFASGGPAILTTIVGGLVGTTSLIGFGSSATGISLVGGTIDLTGT<br>LAGPLINFAFSVPRDGVITSIAGYFSTTAALTLVGSTATITAQLFSSTTPDNTFTAVPGATVTLAPPLTGIIALG<br>TISNGITTGLAIPVTAQTRLLLVFSATATGLSLVNTIVGYASAGITIT |
| SEQ ID NO: 27 | ATGGCGGTTATATCAACTGGACCCATAGAAAATAATTATGTCAGTGGTATTCGGCCTACTCATCGAGTTACCGTG<br>AAAATTGATAATCGTGATACTGTGAATTCTTCTACGGTATTGATTCAGGGTTTTATCTAAATGGTACAAGAACG<br>TTATATGTGCTTGATTTTATAACTGTAAATTCAAATGAAGTGATTACAAAAGATTATTATGCTGATTTTAATTCA<br>TTTGAGTTTGTTTTTACCACTGAAAGTGTTACAGAAAATGAGATTCAAGTTTCAGTCTGGGGTAAAAATTCAATG<br>GGGCAGTTAGTGCACAGCTCACCGTGTTGTATCTTCCGAATTGCTTGTAGCAAAAGGCGCGGGACCGACAGGGCTA<br>ACGGGAGCCACTGGCGCTACCGGAGCTACTGGCGTCACGGGTGTTACCGGAGTCACTGGCGCTACCGGAACTACG<br>GGCGTTATGGGTGATACCGGAGTCACTGGAGTTACCGGAGTTACTGGCGTTACCGGGGCTATCGGAGTCACTGGC<br>GCTATCGGAGTCACGGGGCTACCGGAGCCACAGGAGTTACGGGGCCACTGGAGTTACCGGGGCTATTGGAGTT<br>ACTGGCGCTATCGGAGTCACTGGCGCTACCGGAGCTACTGGCGTTACTGGGGCTACTGGCGCTACTGGAGTCACA<br>GGAGTTACCGGGGCTACTGGCGTTACCGGAGTTACCGGAGTTACTGGCACTACCGGGGCTATCGGAGCTACTGGC<br>GTTACCGGAGCTACTGGCGTCACGGGTATTACCGGAGTCACTGGCGTTACCGGGGCTACTGGCGTTACTGGAGTT<br>ACTGGCATCACAGGCGTTACCGGAGTTACTGGTGTTACTGGTGTTACTGGAGCTACTGGCGTTACCGGGGCTACT<br>GGCGCTACCGGAGCCACTGGCGTTACTGGAGTTACTGCTGGCGCTACTGGAGCTACTGGTGTTACCGGG<br>GCTACCGGGGCTACCGGTGTCACGGGTGATACCGGTGTCACTGGCGCTACCGGGGCTACCGGAGTTTCTGGCGCT<br>ACTGGGGCTACTGGTGTCACGGGTGATACCGGAGTTACCGGAGCGCTACTGGCGCTACAGGTGCTACCGGAGTTACT<br>GGCGGAACAGGTGCAACCGGAGTTACTGGAGTTACTGGCGTTACCGGGGCTATCGGAGTCACTGGCGCTACTGGA<br>GCTACTGGAGCTGCTGGAATCACGGGTGTTACCGGAGTTACTGGCATCACCGGTGCTACCGGGGCTACGGGCGCT<br>ACCGGAGTTACTGGCATCACAGGAGTCACTGGCGCTACCGGAGTTACTGGCGTAACAGGTGCAACCGGAGTTACT |

TABLE 2-continued

Additional Exemplary *Paenibacillus* N-Terminal Targeting Sequences

| Sequence Identifier | Sequence |
|---|---|
| | GGAGTTACCGGGGCTATCGGAGTTACTGGTGTCACCGGAGCTACTGGCGTCACGGGTGTTACCGGAGTCACTGGC<br>GCTACCGGAGCTACTGGCGTTACGGGTGTTACCGGAGTTACCGGAGTTACTGGCGTTACCGGAGCTACTGGCGTT<br>ACCGGAGTTACTGGAGTTACTGGAGTTATTGGAGTTACTGGAGTTACTGGAGTTACTGGAGTTACTGGAGTTACC<br>GGAGTTACCGGAGTTACTGGAGTTACCGGGGCTATCGGAGTCACTGGCGCTATCGGAGTCACGGGGGCTACCGGG<br>GTCACTGGCGCTACCGGAGCTACTGGCGTAACAGGGGCTACTGGAGTTACCGGGGCTATCGGAGTCACTGGCGCT<br>ACTGGAGCTGCTGGAATCACGGGTGTTACCGGAGTCACTGGTGTTACTGGAGTTACCGGAGCTACTGGCATCACG<br>GGTGATACCGGAGTCACTGGCGCTACCGGAGCTACTGGCGTTACGGGTGTTACCGGAGTCACTGGGGCTACCGGA<br>GCTACTGGCGTCACGGGTGATACCGGAGTTACTGGAGTCACTGGCGCTACCGGAGTTACTGGCGTAACAGGTGCA<br>GCCGGAGTTACTGGCATCACGGGGGCTACCGGAGTTACTGGAGTTACCGGGGCTATTGGAGTCACTGGCGCTATC<br>GGAGTCACGGGGGCTACCGGAGCCACAGGAGTTACGGGTATTACCGGAGCTACTGGCGCTACTGGAGCCACAGGT<br>GCTACCGGAGTTACTGGAGTTACTGGCGCTACCGGAGCTACTGGCGCTACTGGCGTCACGGGTTCTACTGGGGTC<br>ACTGGCGCTACTGGCGTTACCGGAGCTACTGGCGTCACGGGTTCTACTGGGGTCACTGGCGCTACTGGCGTTACC<br>GGAGCTACTGGCGTCACGGGTATTACCGGAGTCACTGGCGTTACCGGAGTTACTGGTGCTACTGGAGCTACTGGC<br>GTTACCGGGGCTACCGGAGTCACTGGGGCTACCGGAGCTACTGGCGTCACGGGTATTACCGGAGTCACTGGGGCT<br>ACCGGAGCTACTGGCGTCACGGGTGTTACCGGAGTCACCGGAGTCACTGGAGTTACTGGAGTTACTGGCGCTACC<br>GGAGCTACTGGCGTTACCGGAGCTACTGGCGCTACTGGCGTCACGGGTGATACCGGAGTCACTGGGGCTACCGGA<br>GTTACCGGAGTCACTGGCGCTACTGGGGCTACTGGTGTCACGGGTGTTACCGGAGTCACTGGCGCTACCGGGGCT<br>ACTGGTGTCACGGGTGTTACCGGGGCTACCGGAGCTACTGGCGACACGGGTGTTACCGGAGTCACTGGAGTCACT<br>GGAGTTACCGGAGTTTCTGGCGCTACCGGAGTTACCGGAGTTTCTGGCGCTACCGGAGTTACCGGAGCTACTGGC<br>GTTACCGGGGCTGGGGCTACCGGAGCTACTGGCGCTACTGGAGTCACAGGTGTTACCGGAGTCACTGGCGCTACC<br>GGAGCTACTGGCGCTACTGGAGTCACGGGTGTTACCGGAGTCACTGGCGCTACCGGGGCTACTGGTGTCACGGGT<br>GTTACCGGGGCTACCGGAGCTACTGGCGACACGGGTGTTACCGGAGTCACTGGAGTCACTGGAGTTACCGGAGTT<br>TCTGGCGCTACCGGAGTTACCGGAGCTACTGGCGTTACCGGGGCTGGGGCTACCGGAGCTACTGGCGCTACTGGA<br>GTCACAGGTGTTACCGGAGTCACTGGCGCTACCGGAGCTACTGGCGCTACTGGAGTCACGGGTGTTACCGGAGTC<br>ACTGGCGCTACCGGGGCTACTGGCGCTACTGGAGTCACGGGTGTTACTGGCGTTACGGGTGTTACCGGAGTTTCT<br>GGCATCACCGGTGCTACCGGGGCTATTGGACCTACTGGTGCCACAGGTGTTGGTATAACAGGTTCAACAGGTTCA<br>ACCGGCCCCACTGGCCCACCTCCTACGTTTATAGACGCATACTTTAACGGTAATATTCAACCTCAGACAATTGCT<br>TCGGGATCAAACATTTTAAATATTACTCCAAACCAATCTACTGCACTTACTTATAACGCAGTAACAAGTGTTTTC<br>ACAATACAAAATGCGGGGTTGTATAACATTAGTGTTGTAATAAATCTTGCAACTGCCACACTACCAGAAGCAACA<br>ATTGGGTTATCACTAAATAATTCTACAGCATATCTCGCTCCTGCTGTAACCACGGCAACAAGTGGTCAATTGGTT<br>TTAGTTCAAATTGAGGCTCTTGCTGTCGGAGATACAATTCAATTTAGAAATATATCTGGGTTTCCTATTACCATT<br>GCTAATTCACCAGTAATAGCTAACAGCTCAGGTCATGTAGCTATTTCGAGATTCTCAGCTTTTTCATAA |
| SEQ ID NO: 28 | MAVISTGPIENNYVSGIRPTHRVTVKIDNRDTVNSSTVLIQGFYLNGTRTLYVLDFITVNSNEVITKDYYADFNS<br>FEFVFTTESVTENEIQVSVWGKNSMGQLVTAHRVVSSELLVAKGAGPTGLTGATGATGATGVTGVTGVTGATGTT<br>GVMGDTGVTGVTGVTGVTGAIGVTGAIGVTGATGATGVTGATGVTGAIGVTGAIGVTGATGATGVTGATGATGVT<br>GVTGATGVTGVTGVTGITGAIGATGVTGATGVTGITGVTGVTGATGVTGVTGITGVTGVTGVTGVTGATGVTGAT<br>GATGATGVTGVTGVTGATGATGVTGATGATGVTGDTGVTGATGATGVSGATGATGVTGDTGVTGATGATGATGVT<br>GGTGATGVTGVTGVTGAIGVTGATGATGAAGITGVTGVTGITGATGATGATGVTGITGVTGATGVTGVTGATGVT<br>GVTGAIGVTGVTGATGVTGVTGVTGATGATGVTGVTGVTGVTGVTGATGVTGVTGVTGVIGVTGVTGVTGVTGVT<br>GVTGVTGVTGAIGVTGAIGVTGATGVTGATGATGVTGATGVTGAIGVTGATGAAGITGVTGVTGVTGVTGATGIT<br>GDTGVTGATGATGVTGVTGVTGATGATGVTGDTGVTGVTGATGVTGVTGAAGVTGITGATGVTGVTGAIGVTGAI<br>GVTGATGATGVTGITGATGATGATGATGVTGVTGATGATGATGVTGSTGVTGATGVTGATGVTGSTGVTGATGVT<br>GATGVTGITGVTGVTGVTGATGATGVTGATGVTGATGATGVTGITGVTGATGATGVTGVTGVTGVTGVTGVTGAT<br>GATGVTGATGATGVTGDTGVTGATGVTGVTGATGATGVTGVTGVTGATGATGVTGVTGATGATGDTGVTGVTGVT<br>GVTGVSGATGVTGVSGATGVTGATGVTGAGATGATGATGVTGVTGVTGATGATGATGVTGVTGVTGATGATGVTG<br>VTGATGATGDTGVTGVTGVTGVTGVSGATGVTGATGVTGAGATGATGATGVTGVTGVTGATGATGATGVTGVTGV<br>TGATGATGATGVTGVTGVTGVTGVSGITGATGAIGPTGATGVGITGSTGSTGPTGPPPTFIDAYFNGNIQPQTIA<br>SGSNILNITPNQSTALTYNAVTSVFTIQNAGLYNISVVINLATATLPEATIGLSLNNSTAYLAPAVTTATSGQLV<br>LVQIEALAVGDTIQFRNISGFPITIANSPVIANSSGHVAISRFSAFS |
| SEQ ID NO: 29 | TTGGGAAATTTATTGTTGCGTAAAAGATATCGCTTGACCCAGGTGGCAAGGAAAAAAAAGAAGGAAAGAGATCAA<br>AAGATGGGAGCGTTCCGTTTTATGCCCATTTATCGTACAGGAACGAGCTGCATTCGTAACAAAAAGGGAAATAAA<br>CGTATTTATAGACAGGGTAGAAGAAGAGAGAGAATATGCGCTTATAGACATCATTTGCACGCTGAGCGGGTGCCC<br>TCAGGTTTATCAAATAAAAAAATCTGTTTTATGAAATTCAAAGGTCAACGAAGACTGCGAGGCGGCGAACAGGAG<br>CCTCAAGGCAATTCAGGAGGAGCAGTTCAAGGGGTGCATGGATTAAGGGGGACCGATGGTAATGCTGGGCATCAA<br>GGCATACAAGGTCCGGCTGGGCCACAGGGCATTCCGGGTAGTGCCGGACCCCAGGGCCAGGCGGGCGCCATAGGC<br>CCCCAAGGTGAACAGGGTCTTCAGGGGGTTCCAGGGATTCAAGGCTTGCAAGGAGAGGCTGGGCCACAGGGAGAG<br>CAGGGACCACCGCTTAATTTGGATGGGATCACGGTTGTGCCTGAGGTACAGCGATATTTCTATTTTGCCGATTCA<br>GATCTGACGGGTACGGTTGAAATCCCTATTTCCCAGTTTACGAATGATGATGGACAGTTGGCAAGTCAGCTTCCA<br>GAATTGGGTGCGAACAGCTACACGGATTTGTATATTAATGGGGTACTGCAGGAAAGCAGGTTGTACCAGATAAGT<br>AGTACCACATTGACTGTTGAATTGGAAGAAGCTCTTGTAATTGCGGGTACGCCGTTTATTTTCGAGGTTTTTCAA<br>TTTACATTAAGAATGGCGAACTGA |
| SEQ ID NO: 30 | MGNLLLRKRYRLTQVARKKKKERDQKMGAFRFMPIYRTGTSCIRNKKGNKRIYRQGRRRERICAYRHHLHAERVP<br>SGLSNKKICFMKFKGQRRLRGGEQEPQGNSGGAVQGVHGLRGTDGNAGHQGIQGPAGPQGIPGSAGPQGQAGAIG<br>PQGEQGLQGVPGIQGLQGEAGPQGEQGPPLNLDGITVVPEVQRYFYFADSDLTGTVEIPISQFTNDDGQLASQLP<br>ELGANSYTDLYINGVLQESRLYQISSTTLTVELEEALVIAGTPFIFEVFQFTLRMAN |

In addition to the exemplary N-terminal targeting sequences listed on Table 1 (i.e., SEQ ID NOs: 1-10 and 18) and in Table 2 (i.e., SEQ ID NOs: 19-30), in further embodiments, variant sequences sharing at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with any of the aforementioned sequences may be used, so long as the sequence retains the capability to target the fusion protein to the spore surface of a *Paenibacillus* endospore. In some embodiments, a fragment of at least 5, 6, 7, 8, 9, 10, 11, 12, 13, 14, 15, 16, 17, 18, 19, 20, 21, 22, 23, 24, or 25 contiguous amino acids selected from any of the polypeptide sequences listed in Table 1 may be used. In some aspects, the only required functionality is that the sequence maintains the capability to target a fusion protein to the spore surface of a *Paenibacillus* endospore.

In some embodiments this N-terminal signal sequence, or a variant or fragment thereof, may be used to target a fusion protein to the spore surface of a *Paenibacillus* endospore which comprises a peptide or polypeptide sequence of interest that is heterologous to the linked N-terminal signal sequence. In some embodiments, the N-terminal signal sequence comprises an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with the amino acid sequence of any of the individual sequences listed on Table 1. In some embodiments, the N-terminal signal sequence comprises at least one contiguous sequence of at least 5, 6, 7, 8, 9, 10, 11, 12, 13, 14, 15, 16, 17, 18, 19, 20, 21, 22, 23, 24, or 25 amino acids that is identical to a contiguous sequence of the same number amino acids of any of the individual polypeptide sequences listed on Table 1.

As discussed herein, fusion protein constructs according to several aspects of the disclosure comprise an N-terminal signal sequence or a variant or fragment thereof that targets the fusion protein to the spore surface of a *Paenibacillus* endospore and a polypeptide sequence that is heterologous to the N-terminal signal sequence. However, in further aspects, any of the disclosed sequences, as well as the sequential variants and fragments thereof according to any of the disclosed aspects, may be used for other purposes. The disclosure's focus on aspects wherein these sequences function as N-terminal spore surface targeting sequences is not to be construed as a disclaimer of other functionalities.

In some embodiments, the N-terminal signal sequence comprises a polypeptide with an amino acid sequence as represented by SEQ ID NO: 2, 4, 6, 8 or 10. In alternative embodiments, the N-terminal signal sequence comprises a fragment of SEQ ID NO: 2, 4, 6, 8 or 10 (e.g., a polypeptide with an amino acid sequence comprising at least one contiguous subsequence found in either SEQ ID NO: 2, 4, 6, 8 or 10). In alternative embodiments, the N-terminal signal sequence comprises a variant of SEQ ID NO: 2, 4, 6, 8 or 10 (e.g., a polypeptide with an amino acid sequence that shares a minimum or exact degree of percentage identity with the sequence represented by SEQ ID NO: 2, 4, 6, 8 or 10). In select embodiments, the N-terminal signal sequence may qualify as both a fragment and as a variant, as defined above (e.g., an N-terminal signal sequence comprising a contiguous subsequence found in SEQ ID NO: 2, 4, 6, 8 or 10 followed by a divergent sequence that falls within a disclosed sequence identity range).

In select embodiments, the N-terminal signal sequence comprises an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with the amino acid sequence represented by SEQ ID NO: 2, 4, 6, 8 or 10.

In select embodiments, the N-terminal signal sequence comprises a contiguous sequence of at least 5, 10, 15, 20 or 25 amino acids that is identical to a contiguous sequence of at least 5, 6, 7, 8, 9, 10, 11, 12, 13, 14, 15, 16, 17, 18, 19, 20, 21, 22, 23, 24, or 25 amino acids of the amino acid sequence represented by SEQ ID NO: 2, 4, 6, 8 or 10.

In some embodiments, the N-terminal signal sequence comprises a polypeptide with an amino acid sequence encoded by the nucleotide sequence represented by SEQ ID NO: 1, 3, 5, 7, or 9. In alternative embodiments, the N-terminal signal sequence comprises a fragment of a polypeptide with an amino acid sequence encoded by the nucleotide sequence represented by SEQ ID NO: 1, 3, 5, 7, or 9 (e.g., a polypeptide with an amino acid sequence comprising at least one contiguous subsequence found in a polypeptide with an amino acid sequence encoded by the nucleotide sequence represented by SEQ ID NO: 1, 3, 5, 7, or 9). In alternative embodiments, the N-terminal signal sequence comprises a variant of a polypeptide with an amino acid sequence encoded by the nucleotide sequence represented by SEQ ID NO: 1, 3, 5, 7, or 9 (e.g., a polypeptide with an amino acid sequence that shares a minimum or exact degree of percentage identity with a polypeptide with an amino acid sequence encoded by the nucleotide sequence represented by any of the sequences represented by SEQ ID NO: 1, 3, 5, 7, or 9). In select embodiments, the N-terminal signal sequence may qualify as both a fragment and as a variant, as defined above (e.g., an N-terminal signal sequence comprising a contiguous subsequence found in a polypeptide with an amino acid sequence encoded by the nucleotide sequence represented by SEQ ID NO: 1, 3, 5, 7, or 9 followed by a divergent sequence that falls within a minimum sequence identity range).

In select embodiments, the N-terminal signal sequence comprises a nucleotide sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with the nucleotide sequence represented by SEQ ID NO: 1, 3, 5, 7, or 9.

In select embodiments, the N-terminal signal sequence comprises a nucleotide sequence that hybridizes to a nucleic acid probe complementary to SEQ ID NO: 1, 3, 5, 7, or 9 under moderate or high stringency.

In select embodiments, the N-terminal signal sequence comprises a contiguous sequence of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides that is identical to a contiguous sequence of the same number of nucleotides in the nucleotide sequence represented by SEQ ID NO: 1, 3, 5, 7, or 9.

With respect to any of the alternative N-terminal targeting sequences contemplated by this disclosure, such as the aforementioned embodiments, the minimum required functionality of such sequences in selected aspects is the capability to target a fusion protein to the spore surface of a *Paenibacillus* endospore.

Sporulation-Associated Regulatory Sequences

The disclosure provides multiple upstream regulatory sequences which may be used to express fusion proteins and other constructs according to the disclosure during sporulation (e.g., SEQ ID NOs: 11-15). As described in detail herein, these upstream regulatory sequences may be used to express fusion proteins having an N-terminal targeting sequence which directs a protein of interest to the spore surface of a *Paenibacillus* endospore. In some aspects, these upstream regulatory sequences (or fragments or variants thereof) may also be used to express any heterologous protein of interest during sporulation regardless of whether the protein of interest includes an N-terminal targeting sequence.

In some aspects, transcription of the protein of interest is controlled by a promoter present in any of the upstream regulatory sequences described herein (e.g., any of SEQ ID NOs: 11-15, or a fragment or variant thereof which remains transcriptionally active during sporulation). In some aspects, a DNA construct may comprise a sequence encoding a protein of interest downstream of any of the regulatory sequences described herein (e.g., any of SEQ ID NOs: 11-15), or a fragment or variant thereof which remains transcriptionally active during sporulation. Such fragments may comprise any contiguous 25, 50, 100, 150 or 200 nucleotides of SEQ ID NOs: 11-15, which remains transcriptionally active during sporulation. Similarly, variants may comprise a sequence having at least 50%, 60%, 70%, 80%, or 90% sequence identity compared to any of SEQ ID NOs: 11-15 (or a fragment thereof), which remain transcriptionally active during sporulation. DNA encoding the protein of interest and any upstream regulatory sequence(s) may be integrated into the chromosomal DNA of a *Paenibacillus* or other cell.

Fusion Proteins

The disclosure provides fusion proteins comprising an N-terminal targeting sequence linked, directly or indirectly, to at least one molecule of interest (e.g., polypeptide sequence of a protein or peptide of interest, such as at least one plant growth stimulating protein or peptide). In selected embodiments, the indirect linkage may be an intervening spacer, linker or a regulatory sequence. The protein or peptide may comprise, but is not limited to, a peptide hormone, a non-hormone peptide, an enzyme involved in the production or activation of a plant growth stimulating compound or an enzyme that degrades or modifies a bacterial, fungal, or plant nutrient source. In general, any protein of interest capable of expression in a *Paenibacillus* endospore and heterologous to the selected N-terminal targeting sequence may be used. In some embodiments, the protein of interest is a protein that is expressed in bacteria of the *Paenibacillus* genus. In other embodiments, the protein of interest is isolated from a bacteria of the sames species as the *Paenibacillus* endospore in which the fusion protein will be expressed. In still other embodiments, the protein of interest is isolated from the *Paenibacillus* strain in which the fusion protein will be expressed on the endospore. The targeting sequence can be any of the targeting sequences described above.

In some embodiments, the fusion proteins may comprise a targeting sequence and at least one protein or peptide that protects a plant from a pathogen. The targeting sequence can be any of the targeting sequences described above.

The fusion protein can be made using standard cloning and molecular biology methods known in the art. For example, a gene encoding a protein or peptide (e.g., a gene encoding a plant growth stimulating protein or peptide) can be amplified by polymerase chain reaction (PCR) and ligated to DNA coding for any of the above-described targeting sequences to form a DNA molecule that encodes the fusion protein. The DNA molecule encoding the fusion protein can be cloned into any suitable vector, for example a plasmid vector. The vector suitably comprises a multiple cloning site into which the DNA molecule encoding the fusion protein can be easily inserted. The vector also suitably contains a selectable marker, such as an antibiotic resistance gene, such that bacteria transformed, transfected, or mated with the vector can be readily identified and isolated. Where the vector is a plasmid, the plasmid suitably also comprises an origin of replication. The DNA encoding the fusion protein is suitably under the control of a sporulation promoter that will cause expression of the fusion protein on the spore surface of a *Paenibacillus* endospore (e.g., a native promoter from a *Paenibacillus* family member). In some aspects, transcription of the fusion protein is controlled by a promoter present in any of the upstream regulatory sequences described herein (e.g., any of SEQ ID NOs: 11-15, or a fragment or variant thereof which remains transcriptionally active during sporulation). In some aspects, a DNA construct may comprise a sequence encoding a fusion protein according to the disclosure downstream of any of the regulatory sequences described herein (e.g., any of SEQ ID NOs: 11-15), or a fragment or variant thereof which remains transcriptionally active during sporulation. Such fragments may comprise any contiguous 50, 100, 150 or 200 nucleotides of SEQ ID NOs: 11-15, which remain transcriptionally active during sporulation. Similarly, variants may comprise a sequence having at least 50%, 60%, 70%, 80%, or 90% sequence identity compared to any of SEQ ID NOs: 11-15 (or a fragment thereof), which remains transcriptionally active during sporulation. DNA encoding the fusion protein (e.g., a sequence of any of SEQ ID NOs: 1, 3, 5, 7, 9 or a variant or fragment thereof), with one or more upstream regulatory sequence(s) may be integrated into the chromosomal DNA of a *Paenibacillus* or other cell.

The fusion protein can also comprise additional polypeptide sequences that are not part of the targeting sequence, or the linked protein of interest (e.g., the plant growth stimulating protein or peptide, the protein or peptide that protects a plant from a pathogen, the protein or peptide that enhances stress resistance in a plant, or the plant binding protein or peptide). For example, the fusion protein can include tags or markers to facilitate purification (e.g., a polyhistidine tag) or visualization (e.g., a fluorescent protein such as GFP or YFP) of the fusion protein itself or of the recombinant endospore-producing *Paenibacillus* cells' spores expressing the fusion protein.

Expression of fusion proteins on the spore surface using the targeting sequences described herein is enhanced due to a lack of secondary structure in the amino-termini of these sequences, which allows for native folding of the fused proteins and retention of activity. Proper folding can be further enhanced by the inclusion of a short amino acid linker between the targeting sequence and the fusion partner protein.

Thus, any of the fusion proteins described herein can comprise an amino acid linker between the targeting sequence and the linked protein of interest (e.g., the plant growth stimulating protein or peptide, the protein or peptide that protects a plant from a pathogen, the protein or peptide that enhances stress resistance in a plant, or the plant binding protein or peptide).

The linker can comprise a polyalanine linker or a polyglycine linker. A linker comprising a mixture of both alanine and glycine residues can also be used. For example, where the targeting sequence comprises SEQ ID NO: 2, a fusion protein can have one of the following structures:

No linker: SEQ ID NO: 2—Fusion Partner Protein
Alanine Linker: SEQ ID NO: 2—$A_n$-Fusion Partner Protein
Glycine Linker: SEQ ID NO: 2—$G_n$-Fusion Partner Protein
Mixed Alanine and Glycine Linker: SEQ ID NO: 2—$(A/G)_n$-Fusion Partner Protein where $A_n$, $G_n$, and $(A/G)_n$ are any number of alanines, any number of glycines, or any number of a mixture of alanines and glycines, respectively.

For example, n can be any integer between 1 to 25, such as an integer between 6 to 10. Where the linker comprises a mixture of alanine and glycine residues, any combination of glycine and alanine residues can be used. The N-terminal targeting sequence represented by SEQ ID NO: 2, as shown above. However, any of the other N-terminal targeting sequences disclosed herein may be substituted in place of SEQ ID NO: 2 (e.g., SEQ ID Nos: 4, 6, 8 or 10 or fragments or variants thereof) in the exemplary configurations above. In the structures shown above, "Fusion Partner Protein" represents the linked protein of interest (e.g., a plant growth stimulating protein or peptide, the protein or peptide that protects a plant from a pathogen, the protein or peptide that enhances stress resistance in a plant, or the plant binding protein or peptide).

Alternatively, or in addition, the linker can comprise a protease recognition site. Inclusion of a protease recognition site allows for targeted removal, upon exposure to a protease that recognizes the protease recognition site, of the protein of interest (e.g., a plant growth stimulating protein or peptide, the protein or peptide that protects a plant from a pathogen, the protein or peptide that enhances stress resistance in a plant, or the plant binding protein or peptide).

In certain aspects, the fusion protein comprises an enzyme involved in the production or activation of a plant growth stimulating compound, such as an acetoin reductase, an indole-3-acetamide hydrolase, a tryptophan monooxygenase, an acetolactate synthetase, an α-acetolactate decarboxylase, a pyruvate decarboxylase, a diacetyl reductase, a butanediol dehydrogenase, an aminotransferase, a tryptophan decarboxylase, an amine oxidase, an indole-3-pyruvate decarboxylase, an indole-3-acetaldehyde dehydrogenase, a tryptophan side chain oxidase, a nitrile hydrolase, a nitrilase, a peptidase, a protease, an adenosine phosphate isopentenyltransferase, a phosphatase, an adenosine kinase, an adenine phosphoribosyltransferase, CYP735A, a 5'-ribonucleotide phosphohydrolase, an adenosine nucleosidase, a zeatin cis-trans isomerase, a zeatin O-glucosyltransferase, a β-glucosidase, a cis-hydroxylase, a CK cis-hydroxylase, a CK N-glucosyltransferase, a 2,5-ribonucleotide phosphohydrolase, an adenosine nucleosidase, a purine nucleoside phosphorylase, a zeatin reductase, a hydroxylamine reductase, a 2-oxoglutarate dioxygenase, a gibberellic 2B/3B hydrolase, a gibberellin 3-oxidase, a gibberellin 20-oxidase, a chitosanase, a chitinase, a β-1,3-glucanase, a β-1,4-glucanase, a β-1,6-glucanase, an aminocyclopropane-1-carboxylic acid deaminase, an enzyme involved in producing a nod factor, or any combination of the above.

In other aspects, the fusion protein comprises an enzyme that degrades or modifies a bacterial, fungal, or plant nutrient source, such as a cellulase, a lipase, a lignin oxidase, a protease, a glycoside hydrolase, a phosphatase, a nitrogenase, a nuclease, an amidase, a nitrate reductase, a nitrite reductase, an amylase, an ammonia oxidase, a ligninase, a glucosidase, a phospholipase, a phytase, a pectinase, a glucanase, a sulfatase, a urease, a xylanase, a siderophore, or any combination of the above.

In some embodiments, the fusion protein is expressed under the control of a sporulation promoter native to the targeting sequence, spore surface protein, or spore surface protein fragment of the fusion protein. The fusion protein may be expressed under the control of a high-expression sporulation promoter. In certain aspects, the high-expression sporulation promoter comprises a sigma-K sporulation-specific polymerase promoter sequence. In selected aspects, the fusion protein may be expressed under the control of a promoter that is native to the targeting sequence of the fusion protein. In some cases, the promoter that is native to the targeting sequence will be a high-expression sporulation promoter. In other cases, the promoter that is native to the targeting sequence will not be a high-expression sporulation promoter. In the latter cases, it may be advantageous to replace the native promoter with a high-expression sporulation promoter. Expression of the fusion protein under the control of a high-expression sporulation promoter provides for increased expression of the fusion protein on the spore surface of the *Paenibacillus* endospore. The high-expression sporulation promoter can comprise one or more sigma-K sporulation-specific promoter sequences.

As described above, the fusion proteins may comprise a targeting sequence and at least one heterologous protein that may comprise a growth stimulating protein or peptide. The plant growth stimulating protein or peptide can comprise, among other things, a peptide hormone, a non-hormone peptide, an enzyme involved in the production or activation of a plant growth-stimulating compound, or an enzyme that degrades or modifies a bacterial, fungal, or plant nutrient source. The plant growth stimulating protein or peptide can comprise an enzyme involved in the production or activation of a plant growth-stimulating compound. The enzyme involved in the production or activation of a plant growth stimulating compound can be any enzyme that catalyzes any step in a biological synthesis pathway for a compound that stimulates plant growth or alters plant structure, or any enzyme that catalyzes the conversion of an inactive or less active derivative of a compound that stimulates plant growth or alters plant structure into an active or more active form of the compound. Alternatively, the plant growth-stimulating compound can comprise a plant growth hormone, e.g., a cytokinin or a cytokinin derivative, ethylene, an auxin or an auxin derivative, a gibberellic acid or a gibberellic acid derivative, abscisic acid or an abscisic acid derivative, or a jasmonic acid or a jasmonic acid derivative.

Where the enzyme comprises a protease or peptidase, the protease or peptidase can be a protease or peptidase that cleaves proteins, peptides, proproteins, or preproproteins to create a bioactive peptide. The bioactive peptide can be any peptide that exerts a biological activity. The protease or peptidase that cleaves proteins, peptides, proproteins, or preproproteins to create a bioactive peptide can comprise subtilisin, an acid protease, an alkaline protease, a proteinase, an endopeptidase, an exopeptidase, thermolysin, papain, pepsin, trypsin, pronase, a carboxylase, a serine protease, a glutamic protease, an aspartate protease, a cysteine protease, a threonine protease, or a metalloprotease.

The plant growth stimulating protein can also comprise an enzyme that degrades or modifies a bacterial, fungal, or plant nutrient source. Such enzymes include cellulases, lipases, lignin oxidases, proteases, glycoside hydrolases, phosphatases, nitrogenases, nucleases, amidases, nitrate reductases, nitrite reductases, amylases, ammonia oxidases, ligninases, glucosidases, phospholipases, phytases, pectinases, glucanases, sulfatases, ureases, xylanases, and siderophores. When introduced into a plant growth medium or applied to a plant, seed, or an area surrounding a plant or a plant seed, fusion proteins comprising enzymes that degrade or modify a bacterial, fungal, or plant nutrient source can aid in the processing of nutrients in the vicinity of the plant and result in enhanced uptake of nutrients by the plant or by beneficial bacteria or fungi in the vicinity of the plant. The fusion proteins can comprise a targeting sequence and at least one protein or peptide that protects a plant from a pathogen. The protein or peptide can comprise a protein or peptide that stimulates a plant immune response. For example, the protein or peptide that stimulates a plant immune response can comprise a plant immune system enhancer protein or peptide. The plant immune system enhancer protein or peptide can be any protein or peptide that has a beneficial effect on the immune system of a plant. Alternatively, the protein or peptide that protects a plant from a pathogen can be a protein or peptide that has antibacterial activity, antifungal activity, or both antibacterial and antifungal activity. The protein or peptide that protects a plant from a pathogen can also be a protein or peptide that has insecticidal activity, helminthicidal activity, suppresses insect or worm predation, or a combination thereof. The protein that protects a plant from a pathogen can comprise an enzyme. Suitable enzymes include proteases and lactonases. The proteases and lactonases can be specific for a bacterial signaling molecule (e.g., a bacterial lactone homoserine signaling molecule). The enzyme can also be an enzyme that is specific for a cellular component of a bacterium or fungus.

The fusion proteins can comprise a targeting sequence and at least one protein or peptide that enhances stress resistance in a plant. For example, the protein or peptide that enhances stress resistance in a plant comprises an enzyme that degrades a stress-related compound. Stress-related compounds include, but are not limited to, aminocyclopropane-1-carboxylic acid (ACC), reactive oxygen species, nitric oxide, oxylipins, and phenolics. Specific reactive oxygen species include hydroxyl, hydrogen peroxide, oxygen, and superoxide. The enzyme that degrades a stress-related compound can comprise a superoxide dismutase, an oxidase, a catalase, an aminocyclopropane-1-carboxylic acid deaminase, a peroxidase, an antioxidant enzyme, or an antioxidant peptide.

The protein or peptide that enhances stress resistance in a plant can also comprise a protein or peptide that protects a plant from an environmental stress. The environmental stress can comprise, for example, drought, flood, heat, freezing, salt, heavy metals, low pH, high pH, or a combination thereof. For instance, the protein or peptide that protects a plant from an environmental stress can comprise an ice nucleation protein, a prolinase, a phenylalanine ammonia lyase, an isochirismate synthase, an isochorismate pyruvate lyase, or a choline dehydrogenase.

The fusion proteins can comprise a targeting sequence and at least plant binding protein or peptide. The plant binding protein or peptide can be any protein or peptide that is capable of specifically or non-specifically binding to any part of a plant (e.g., a plant root or an aerial portion of a plant such as a leaf, stem, flower, or fruit) or to plant matter. Thus, for example, the plant binding protein or peptide can be a root binding protein or peptide, or a leaf binding protein or peptide.

Recombinant *Paenibacillus* Endospores and Cells Expressing the Fusion Proteins

The fusion proteins described herein can be expressed by recombinant endospore-producing *Paenibacillus* cells (e.g., *P. terrae*). The fusion protein can be any of the fusion proteins discussed above. The recombinant endospore-producing *Paenibacillus* cells can co-express two or more of any of the fusion proteins discussed above. For example, the recombinant endospore-producing *Paenibacillus* cells can co-express at least one fusion protein that comprises a plant binding protein or peptide, together with at least one fusion protein comprising a plant growth stimulating protein or peptide, at least one fusion protein comprising a protein or peptide that protects a plant from a pathogen, or at least one protein or peptide that enhances stress resistance in a plant.

The recombinant endospore-producing *Paenibacillus* cells may comprise *Paenibacillus* cells, such as *Paenibacillus* sp. NRRL B-50972, *Paenibacillus terrae, Paenibacillus polymyxa*, or *Paenibacillus peoriae* cells. In other aspects, the endospore-producing *Paenibacillus* cell may be selected from any of the exemplary *Paenibacillus* species described herein.

To generate recombinant endospore-producing *Paenibacillus* cells expressing a fusion protein, any *Paenibacillus* bacterium may be transformed using standard methods known in the art (e.g., by electroporation with a vector encoding the fusion protein). The bacteria can then be screened to identify transformants by any method known in the art. For example, where the vector includes an antibiotic resistance gene, the bacteria can be screened for antibiotic resistance. Alternatively, DNA encoding the fusion protein can be integrated into the chromosomal DNA of a *Paenibacillus* cell. The recombinant endospore-producing *Paenibacillus* cells can then exposed to conditions that will induce sporulation. Suitable conditions for inducing sporulation are known in the art. For example, the recombinant endospore-producing *Paenibacillus* cells can be plated onto agar plates, and incubated at a temperature of about 30° C. for several days (e.g., 3 days), or alternatively cultured in Schaeffer Sporulation Medium.

Inactivated strains, non-toxic strains, or genetically manipulated strains of any of the above species can also suitably be used. Alternatively or in addition, once the recombinant *Paenibacillus* family spores expressing the fusion protein have been generated, they can be inactivated to prevent further germination once in use. Any method for inactivating bacterial spores that is known in the art can be used. Suitable methods include, without limitation, heat treatment, gamma irradiation, x-ray irradiation, UV-A irradiation, UV-B irradiation, chemical treatment (e.g., treatment with gluteraldehyde, formaldehyde, hydrogen peroxide, acetic acid, bleach, or any combination thereof), or a combination thereof. Alternatively, spores derived from nontoxigenic strains, or genetically or physically inactivated strains, can be used.

Fusion protein constructs according to the present disclosure comprise an N-terminal signal sequence or a variant or fragment thereof that targets the fusion protein to the spore surface of a *Paenibacillus* endospore and a polypeptide sequence that is heterologous to the N-terminal signal sequence. In select embodiments, the N-terminal signal sequence and the polypeptide sequence that is heterologous to the N-terminal signal sequence are directly linked. In other aspects, an intervening linker or spacer sequence may be present. In further aspects, a cleavage sequence or other regulatory sequence may be positioned between the two regions. The polypeptide sequence that is heterologous to the N-terminal signal sequence may comprise one or more functional proteins. In aspects where multiple functional proteins are contained in the polypeptide sequence that is heterologous to the N-terminal signal sequence, at least one spacer, cleavage sequence or other regulatory element may be located between the two or more functional proteins.

The polypeptide sequence that is heterologous to the N-terminal signal sequence may be, for example: (a) a plant growth stimulating protein or peptide; (b) a protein or peptide that protects a plant from a pathogen; (c) a protein or peptide that enhances stress resistance of a plant; (d) a plant binding protein or peptide; (e) a plant immune system enhancer protein or peptide; or (f) a protein or peptide that enhances nutrient uptake. When expressed in *Paenibacillus*, these fusion proteins are targeted to the spore surface of the *Paenibacillus* endospore and are physically oriented such that the protein or peptide is displayed on the outside of the spore.

This *Paenibacillus* spore surface display system can be used to deliver peptides, enzymes, and other proteins to plants (e.g., to plant foliage, fruits, flowers, stems, or roots) or to a plant growth medium such as soil. Peptides, enzymes, and proteins delivered to the soil or another plant growth medium in this manner persist and exhibit activity in the soil for extended periods of time. Introduction of recombinant endospore-producing *Paenibacillus* cells expressing the fusion proteins described herein into soil or the rhizosphere of a plant may lead to a beneficial enhancement of plant growth in many different soil conditions. The use of the *Paenibacillus* spore surface display system to create these enzymes allows them to continue to exert their beneficial effects on the plant and the rhizosphere over the first months of a plants life, and in some aspects over longer period of time up to and including the life of the plant.

In some aspects, compositions comprising recombinant endospore-producing *Paenibacillus* cells or endospores produced by such cells according to any aspect described herein may be applied directly to a plant (e.g., as a powder, suspension or solution, to a seed, or to a field). In some aspects, such compositions are applied to a field prior to or after seeding, or alternatively prior to or after sprouting (e.g., pre- or post-planting, or pre- or post-emergence).

In alternative aspects, the fusion proteins and/or compositions disclosed herein may be delivered to a plant, seed, and/or field indirectly by applying recombinant *Paenibacillus* cells or spores to the plant, seed, or field. In these aspects, a fusion protein may be expressed or generated by the recombinant *Paenibacillus* cells (e.g., in the field), resulting in delivery of the fusion protein to the plant, seed, or field.

Recombinant Endospore-Producing *Paenibacillus* Cells Having Plant-Growth Promoting Effects and/or Other Beneficial Attributes Some *Paenibacillus* bacteria are known to have inherent beneficial attributes. For example, some strains have plant-growth promoting or insecticidal (e.g., mosquitocidal) effects. Any of the fusion proteins described herein can be expressed in such strains.

For example, the recombinant endospore-producing *Paenibacillus* cells may comprise a plant-growth promoting strain of *Paenibacillus*. The plant-growth promoting strain of bacteria can comprise a strain of bacteria that produces an insecticidal toxin (e.g., a Bin toxin), produces a fungicidal compound (e.g., a β-1,3-glucanase, a chitosinase, a lyticase, or a combination thereof), produces a nematocidal compound (e.g., a Cry toxin), produces a bacteriocidal compound, is resistant to one or more antibiotics, comprises one or more freely replicating plasmids, binds to plant roots, colonizes plant roots, forms biofilms, solubilizes nutrients, secretes organic acids, or any combination thereof.

Biological Control Agents

Compositions provided by the disclosure may further include biological control agents. Biological control agents can include, in particular, bacteria, fungi or yeasts, protozoa, viruses, entomopathogenic nematodes, inoculants and botanicals and/or mutants of them having all identifying characteristics of the respective strain, and/or at least one metabolite produced by the respective strain that exhibits activity against insects, mites, nematodes and/or phytopathogens. The disclosure provides combinations of the above-described recombinant *Paenibacillus* endospores with the particular biological control agents described herein and/or to mutants of specific strains of microorganisms described herein, where the mutants have all the identifying characteristics of the respective strain, and/or at least one metabolite produced by the respective strain that exhibits activity against insects, mites, nematodes and/or phytopathogens or promotes plant growth and/or enhances plant health. According to the disclosure, the biological control agents described herein may be employed or used in any physiologic state such as active or dormant.

Exemplary Compositions

In selected aspects, the disclosure provides compositions comprising a) a recombinant endospore-producing *Paenibacillus* cell that expresses a fusion protein comprising: a targeting sequence that localizes the fusion protein, which comprises a heterologous protein of interest, to the spore surface of a *Paenibacillus* family member; and b) at least one further and different particular biological control agent disclosed herein and/or a mutant of a specific strain of a microorganism disclosed herein having all identifying characteristics of the respective strain, and/or at least one metabolite produced by the respective strain that exhibits activity against insects, mites, nematodes and/or phytopathogens in a synergistically effective amount. In alternative aspects, the composition comprises at least one additional fungicide and/or at least one insecticide, with the proviso that the recombinant endospore-producing *Paenibacillus* cells, the insecticide and the fungicide are not identical. In another aspect, composition is used for reducing overall damage of plants and plant parts, as well as, losses in harvested fruits or vegetables caused by insects, mites, nematodes and/or phytopathogens. In another aspect, the composition increases the overall plant health.

The term "plant health" generally comprises various sorts of improvements of plants that are not connected to the control of pests. For example, advantageous properties that may be mentioned are improved crop characteristics including: emergence, crop yields, protein content, oil content, starch content, more developed root system, improved root growth, improved root size maintenance, improved root effectiveness, improved stress tolerance (e.g., against drought, heat, salt, UV, water, cold), reduced ethylene (reduced production and/or inhibition of reception), tillering increase, increase in plant height, bigger leaf blade, less dead basal leaves, stronger tillers, greener leaf color, pigment content, photosynthetic activity, less input needed (such as fertilizers or water), less seeds needed, more productive tillers, earlier flowering, early grain maturity, less plant verse (lodging), increased shoot growth, enhanced plant vigor, increased plant stand and early and better germination.

Compositions provided by the disclosure may be screened to identify potential benefits to plant growth, health, or other positive attributes by comparing plants which are grown under the same environmental conditions, whereby a part of said plants is treated with a composition according to the present disclosure and another part of said plants is not treated with a composition according to the present disclosure. Instead, said other part is not treated at all or is treated with a suitable control (i.e., an application without a composition according to the disclosure such as an application without all active ingredients), an application without the recombinant endospore-producing *Paenibacillus* cells as described herein, or an application without a further particular biological control agent disclosed herein.

The composition according to the present disclosure may be applied in any desired manner, such as in the form of a seed coating, soil drench, and/or directly in-furrow and/or as a foliar spray and applied either pre-emergence, post-emergence or both. In other words, the composition can be applied to the seed, the plant or to harvested fruits and vegetables or to the soil wherein the plant is growing or wherein it is desired to grow (plant's locus of growth).

Reducing the overall damage of plants and plant parts often results in healthier plants and/or in an increase in plant vigor and yield. Preferably, the composition according to the present disclosure is used for treating conventional or transgenic plants or seed thereof.

In another aspect, compositions provided by the disclosure improve animal health or the general overall physical condition of such animals Indicia of enhanced health include one or more of the following: amelioration or reversal of a disease state in an animal; increase in weight gain, which may include an increase in weight of a specific part of the animal or an increase in overall weight; maintenance of gut microflora; increase in feed utilization efficiency; reduction in risk of mortality; increase in disease resistance; reduction in morbidity; increase in immune response; decrease in occurrence of diarrhea, increase in productivity; and/or reduction of pathogen shedding. The present disclosure also relates to methods for improving animal health by administering to an animal a therapeutic or effective amount of any of the compositions described above comprising recombinant endospore-producing *Paenibacillus* cells that express a fusion protein. In some aspects such fusion protein includes an enzyme that aids in the digestion of feed, such as amylase, glucanase, glucoamylase, cellulase, xylanase, glucanase, and pectinase or an immune modulator, such as an antibody. An effective amount of a composition is an amount effective to enhance the health of an animal in comparison to an animal that has not been administered the composition but otherwise has been administered the same diet (including feed and other compounds) as has the animal receiving the compositions of the present invention. The term "therapeutic amount" refers to an amount sufficient to ameliorate or reverse a disease state in an animal.

In another aspect, compositions provided by the disclosure remove pollution or contaminants from media such as soil, groundwater, sediment or surface water. The present disclosure also relates to methods for removing pollution or contaminants from media such as soil, groundwater, sediment or surface water by applying to such media an effective amount of any of the compositions described above comprising recombinant endospore-producing *Paenibacillus* cells that express a fusion protein on the spore surface.

Methods of Using Recombinant *Paenibacillus* Constructs and Compositions

The present disclosure also relates to methods for stimulating plant growth using any of the compositions described above comprising recombinant endospore-producing *Paenibacillus* cells that express a fusion protein and at least one of the further particular biological control agents described herein. The method for stimulating plant growth comprises applying to a plant, a seed, a plant part, to the locus surrounding the plant or in which the plant will be planted (e.g., soil or other growth medium) a composition comprising recombinant endospore-producing *Paenibacillus* cells that express a fusion protein comprising: (i) a heterologous protein (e.g., at least one plant growth stimulating protein); and (ii) a targeting sequence; and at least one further particular biological control agent disclosed herein and/or a mutant of a specific strain of a microorganism disclosed herein having all identifying characteristics of the respective strain, and/or at least one metabolite produced by the respective strain that exhibits activity against insects, mites, nematodes and/or phytopathogens in a synergistically effective amount.

In another aspect of the present disclosure a method for reducing overall damage of plants and plant parts as well as losses in harvested fruits or vegetables caused by insects, mites, nematodes and/or phytopathogens is provided comprising the step of simultaneously or sequentially applying the recombinant endospore-producing *Paenibacillus* cells and at least one further particular biological control agent described herein in a synergistically effective amount.

In one embodiment of the present method the composition further comprises at least one fungicide. In one aspect, the at least one fungicide is a synthetic fungicide. In another embodiment, the composition comprises at least one insecticide in addition to the fungicide or in place of the fungicide, provided that the insecticide, the fungicide, the recombinant endospore-producing *Paenibacillus* cells and the particular biological control agent disclosed herein are not identical.

The method of the present disclosure includes the following application methods, namely both of the recombinant endospore-producing *Paenibacillus* cells and the at least one further particular biological control agent disclosed herein may be formulated into a single, stable composition with an agriculturally acceptable shelf life (so called "solo-formulation"), or being combined before or at the time of use (so called "combined-formulations").

If not mentioned otherwise, the expression "combination" stands for the various combinations of the recombinant endospore-producing *Paenibacillus* cells and at least one further particular biological control agent disclosed herein, and optionally at least one fungicide and/or at least one insecticide, in a solo-formulation, in a single "ready-mix" form, in a combined spray mixture composed from solo-formulations, such as a "tank-mix", and especially in a combined use of the single active ingredients when applied in a sequential manner, i.e., one after the other within a reasonably short period, such as a few hours or days, e.g., 2 hours to 7 days. The order of applying the composition according to the present disclosure is not essential for working the present disclosure. Accordingly, the term "combination" also encompasses the presence of the recombinant endospore-producing *Paenibacillus* cells and the at least one further particular biological control agent disclosed herein, and optionally at least one fungicide and/or insecticide on or in a plant to be treated or its surrounding, habitat or storage space, e.g., after simultaneously or consecutively applying the recombinant endospore-producing *Paenibacillus* cells and the at least one further particular biological control agent disclosed herein, and optionally at least one fungicide and/or at least one insecticide to a plant or its surrounding, habitat or storage space.

If the recombinant endospore-producing *Paenibacillus* cells and the at least one further particular biological control agent described herein, and optionally at least one fungicide and/or at least one insecticide are employed or used in a sequential manner, it is preferred to treat the plants or plant parts (which includes seeds and plants emerging from the seed), harvested fruits and vegetables according to the following method: First, apply at least one fungicide and/or at least one insecticide on the plant or plant parts, and second apply the further particular biological control agent described herein and the recombinant endospore-producing *Paenibacillus* cells to the same plant or plant parts. By this application manner the amount of residues of insecticides/fungicides on the plant upon harvesting is as low as possible. The time periods between the first and the second application within a (crop) growing cycle may vary and depend on the effect to be achieved. For example, the first application is done to prevent an infestation of the plant or plant parts with insects, mites, nematodes and/or phytopathogens (this is particularly the case when treating seeds) or to combat the infestation with insects, mites, nematodes and/or phytopathogens (this is particularly the case when treating plants and plant parts) and the second application is done to prevent or control the infestation with insects, mites, nematodes and/or phytopathogens and/or to promote plant growth. Control in this context means that the composition comprising the recombinant endospore-producing *Paenibacillus* cells and the particular biological control agent disclosed herein are not able to fully exterminate the pests or phytopathogenic fungi but are able to keep the infestation on an acceptable level.

The present disclosure also provides methods of enhancing the killing, inhibiting, preventative and/or repelling activity of the compositions of the present disclosure by multiple applications. In some other embodiments, the compositions of the present disclosure are applied to a plant and/or plant part for two times, during any desired development stages or under any predetermined pest pressure, at an interval of about 1 hour, about 5 hours, about 10 hours, about 24 hours, about two days, about 3 days, about 4 days, about 5 days, about 1 week, about 10 days, about two weeks, about three weeks, about 1 month or more. Still in some embodiments, the compositions of the present disclosure are applied to a plant and/or plant part for more than two times, for example, 3 times, 4 times, 5 times, 6 times, 7 times, 8 times, 9 times, 10 times, or more, during any desired development stages or under any predetermined pest pressure, at an interval of about 1 hour, about 5 hours, about 10 hours, about 24 hours, about two days, about 3 days, about 4 days, about 5 days, about 1 week, about 10 days, about two weeks, about three weeks, about 1 month or more. The intervals between each application can vary if it is desired. One skilled in the art will be able to determine the application times and length of interval depending on plant species, plant pest species, and other factors.

By following the before mentioned steps, a very low level of residues of the at least one fungicide and/or at least one insecticide on the treated plant, plant parts, and the harvested fruits and vegetables can be achieved.

If not mentioned otherwise the treatment of plants or plant parts (which includes seeds and plants emerging from the seed), harvested fruits and vegetables with the composition according to the disclosure is carried out directly or by action on their surroundings, habitat or storage space using customary treatment methods, for example dipping, spraying, atomizing, irrigating, evaporating, dusting, fogging, broadcasting, foaming, painting, spreading-on, watering (drenching), drip irrigating. It is furthermore possible to apply the recombinant endospore-producing *Paenibacillus* cells, the at least one further particular biological control agent described herein, and optionally the at least one fungicide and/or the at least one insecticide as solo-formulation or combined-formulations by the ultra-low volume method, or to inject the composition according to the present disclosure as a composition or as sole-formulations into the soil (in-furrow).

The term "plant to be treated" encompasses every part of a plant including its root system and the material—e.g., soil or nutrition medium—which is in a radius of at least 10 cm, 20 cm, 30 cm around the caulis or bole of a plant to be treated or which is at least 10 cm, 20 cm, 30 cm around the root system of said plant to be treated, respectively.

The amount of the recombinant endospore-producing *Paenibacillus* cells, which is used or employed in combination with at least one further particular biological control agent described herein, optionally in the presence of at least one fungicide and/or the at least one insecticide, depends on the final formulation as well as size or type of the plant, plant parts, seeds, harvested fruits and vegetables to be treated. Usually, the recombinant endospore-producing *Paenibacillus* cells to be employed or used according to the disclosure is present in about 1% to about 80% (w/w), preferably in about 1% to about 60% (w/w), more preferably about 10% to about 50% (w/w) of its solo-formulation or combined-formulation with the at least one further particular biological control agent described herein, and optionally the fungicide and/or the at least one insecticide.

Also the amount of the at least one further particular biological control agent disclosed herein which is used or employed in combination with the recombinant endospore-producing *Paenibacillus* cells, optionally in the presence of at least one fungicide and/or the at least one insecticide, depends on the final formulation as well as size or type of the plant, plant parts, seeds, harvested fruit or vegetable to be treated. Usually, the further particular biological control agent described herein to be employed or used according to the disclosure is present in about 0.1% to about 80% (w/w), preferably 1% to about 60% (w/w), more preferably about 10% to about 50% (w/w) of its solo-formulation or combined-formulation with the recombinant endospore-producing *Paenibacillus* cells, and optionally the at least one fungicide and/or the at least one insecticide.

Application of the recombinant endospore-producing *Paenibacillus* cells may be effected as a foliar spray, as a soil treatment, and/or as a seed treatment/dressing. When used as a foliar treatment, in one embodiment, about 1/16 to about 5 gallons of whole broth are applied per acre. When used as a soil treatment, in one embodiment, about 1 to about 5 gallons of whole broth are applied per acre. When used for seed treatment about 1/32 to about 1/4 gallons of whole broth are applied per acre. For seed treatment, the end-use formulation contains at least $1\times10^4$, at least $1\times10^5$, at least $1\times10^6$, $1\times10^7$, at least $1\times10^8$, at least $1\times10^9$, at least $1\times10^{10}$ colony forming units per gram.

The ratio can be calculated based on the amount of the at least one further particular biological control agent disclosed herein, at the time point of applying said component of a combination according to the disclosure to a plant or plant part and the amount of the recombinant endospore-producing *Paenibacillus* cells shortly prior (e.g., 48 h, 24 h, 12 h, 6 h, 2 h, 1 h) or at the time point of applying said component of a combination according to the disclosure to a plant or plant part.

The application of the recombinant endospore-producing *Paenibacillus* cells and the at least one further particular biological control agent disclosed herein to a plant or a plant part can take place simultaneously or at different times as long as both components are present on or in the plant after the application(s). In cases where the recombinant endospore-producing *Paenibacillus* cells and further particular biological control agent disclosed herein are applied at different times and the further particular biological control agent disclosed herein is applied prior to the recombinant endospore-producing *Paenibacillus* cells, the skilled person can determine the concentration of further particular biological control agent disclosed herein on/in a plant by chemical analysis known in the art, at the time point or shortly before the time point of applying the recombinant endospore-producing *Paenibacillus* cells. Vice versa, when the recombinant endospore-producing *Paenibacillus* cells are applied to a plant first, the concentration of the recombinant endospore-producing *Paenibacillus* cells can be determined using tests which are also known in the art, at the time point or shortly before the time point of applying the further particular biological control agent disclosed herein.

In another aspect of the present disclosure a seed treated with the composition as described above is provided. The control of insects, mites, nematodes and/or phytopathogens by treating the seed of plants has been known for a long time and is a subject of continual improvements. Nevertheless, the treatment of seed entails a series of problems which cannot always be solved in a satisfactory manner. Thus, it is desirable to develop methods for protecting the seed and the germinating plant that remove the need for, or at least significantly reduce, the additional delivery of crop protection compositions in the course of storage, after sowing or after the emergence of the plants. It is desirable, furthermore, to optimize the amount of active ingredient employed in such a way as to provide the best-possible protection to the seed and the germinating plant from attack by insects, mites, nematodes and/or phytopathogens, but without causing damage to the plant itself by the active ingredient employed. In particular, methods for treating seed ought also to take into consideration the intrinsic insecticidal and/or nematicidal properties of pest-resistant or pest-tolerant transgenic plants, in order to achieve optimum protection of the seed and of the germinating plant with a minimal use of crop protection compositions.

The present disclosure therefore also relates in particular to a method for protecting seed and germinating plants from attack by pests, by treating the seed with the recombinant endospore-producing *Paenibacillus* cells as defined above and at least one further biological control agent selected from particular microorganisms disclosed herein and/or a mutant of a specific strain of microorganism disclosed herein having all identifying characteristics of the respective strain, and/or at least one metabolite produced by the respective strain that exhibits activity against insects, mites, nematodes and/or phytopathogens and optionally at least one fungicide and/or optionally at least one insecticide of the disclosure. The method of the disclosure for protecting seed and germinating plants from attack by pests encompasses a method in which the seed is treated simultaneously in one operation with the recombinant endospore-producing *Paenibacillus* cells and the at least one further particular biological control agent described herein, and optionally the at least one fungicide and/or the at least one insecticide. It also encompasses a method in which the seed is treated at different times with the recombinant endospore-producing *Paenibacillus* cells and the at least one further particular biological control agent disclosed herein, and optionally the at least one fungicide and/or the at least one insecticide.

The disclosure further provides methods of treating seeds for the purpose of protecting the seed and the resultant plant against insects, mites, nematodes and/or phytopathogens. The disclosure also relates to seed which at the same time has been treated with a the recombinant endospore-producing *Paenibacillus* cells and at least one further particular biological control agent described herein, and optionally at least one fungicide and/or the at least one insecticide. The disclosure further relates to seed which has been treated at different times with the recombinant endospore-producing *Paenibacillus* cells and the at least one further particular biological control agent disclosed herein and optionally the at least one fungicide and/or the at least one insecticide. In the case of seed which has been treated at different times with the recombinant endospore-producing *Paenibacillus* cells and the at least one further particular biological control agent disclosed herein, and optionally the at least one fungicide and/or the at least one insecticide, the individual active ingredients in the composition of the disclosure may be present in different layers on the seed.

Furthermore, the disclosure relates to seed which, following treatment with the composition of the disclosure, is subjected to a film-coating process in order to prevent dust abrasion of the seed.

One of the advantages of the present disclosure is that, owing to the particular systemic properties of the compositions of the disclosure, the treatment of the seed with these compositions provides protection from insects, mites, nematodes and/or phytopathogens not only to the seed itself but also to the plants originating from the seed, after they have emerged. In this way, it may not be necessary to treat the crop directly at the time of sowing or shortly thereafter. A further advantage is to be seen in the fact that, through the treatment of the seed with composition of the disclosure, germination and emergence of the treated seed may be promoted.

The compositions of the disclosure are suitable for protecting seed of any variety of plant which is used in agriculture, in greenhouses, in forestry or in horticulture. More particularly, the seed in question is that of cereals (e.g., wheat, barley, rye, oats and millet), maize, cotton, soybeans, rice, potatoes, sunflower, coffee, tobacco, canola, oilseed rape, beets (e.g., sugar beet and fodder beet), peanuts, vegetables (e.g., tomato, cucumber, bean, brassicas, onions and lettuce), fruit plants, lawns and ornamentals. Particularly important is the treatment of the seed of cereals (such as wheat, barley, rye and oats) maize, soybeans, cotton, canola, oilseed rape and rice.

For the purposes of the present disclosure, the composition of the disclosure is applied alone or in a suitable formulation to the seed. The seed is preferably treated in a condition in which its stability is such that no damage occurs in the course of the treatment. Generally speaking, the seed may be treated at any point in time between harvesting and sowing. Typically, seed is used which has been separated from the plant and has had cobs, hulls, stems, husks, hair or pulp removed. Thus, for example, seed may be used that has been harvested, cleaned and dried to a moisture content of less than 15% by weight. Alternatively, seed can also be used that after drying has been treated with water, for example, and then dried again.

When treating seed it is necessary, generally speaking, to ensure that the amount of the composition of the disclosure, and/or of other additives, that is applied to the seed is selected such that the germination of the seed is not adversely affected, and/or that the plant which emerges from the seed is not damaged. This is the case in particular with active ingredients which may exhibit phytotoxic effects at certain application rates.

The compositions of the disclosure can be applied directly, in other words without comprising further components and without having been diluted. As a general rule, it is preferable to apply the compositions in the form of a suitable formulation to the seed. Suitable formulations and methods for seed treatment are known to the skilled person and are described in, for example, the following documents: U.S. Pat. Nos. 4,272,417 A; 4,245,432 A; 4,808,430 A; 5,876,739 A; U.S. Patent Publication No. 2003/0176428 A1; WO 2002/080675 A1; WO 2002/028186 A2, the contents of each of which being incorporated herein by reference.

The combinations which can be used in accordance with the disclosure may be converted into the customary seed-dressing formulations, such as solutions, emulsions, suspensions, powders, foams, slurries or other coating compositions for seed, and also ULV formulations. These formulations are prepared in a known manner, by mixing composition with customary adjuvants, such as, for example, customary extenders and also solvents or diluents, colorants, wetters, dispersants, emulsifiers, antifoams, preservatives, secondary thickeners, stickers, gibberellins, and also water. Colorants which may be present in the seed-dressing formulations which can be used in accordance with the invention include all colorants which are customary for such purposes. In this context it is possible to use not only pigments, which are of low solubility in water, but also water-soluble dyes. Examples include the colorants known under designations Rhodamine B, C. I. Pigment Red 112, and C. I. Solvent Red 1.

Depending on the plant species or plant cultivars, their location and growth conditions (soils, climate, vegetation period, diet), using or employing the composition according to the present disclosure the treatment according to the disclosure may also result in super-additive ("synergistic") effects. Thus, for example, by using or employing inventive composition in the treatment according to the disclosure, reduced application rates and/or a widening of the activity spectrum and/or an increase in the activity better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates of the inventive composition in the treatment according to the disclosure may also have a strengthening effect in plants. The defense system of the plant against attack by unwanted phytopathogenic fungi and/or microorganisms and/or viruses is mobilized. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these phytopathogenic fungi and/or microorganisms and/or viruses. Thus, by using or employing composition according to the present disclosure in the treatment according to the disclosure, plants can be protected against attack by the abovementioned pathogens within a certain period of time after the treatment. The period of time within which protection is effected generally extends from 1 to 10 days, preferably 1 to 7 days, after the treatment of the plants with the active compounds.

Any of the compositions disclosed herein may include one or more agrochemicals. Similarly, the methods of applying compositions according to the disclosure may further comprise introducing at least one agrochemical into the plant growth medium or applying at least one agrochemical to plants or seeds.

The agrochemical can comprise a fertilizer (e.g., a liquid fertilizer), a micronutrient fertilizer material (e.g., boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination thereof), an insecticide (e.g., an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof), an herbicide (e.g., a chlorophenoxy compound, a nitrophenolic compound, a nitrocresolic compound, a dipyridyl compound, an acetamide, an aliphatic acid, an anilide, a benzamide, a benzoic acid, a benzoic acid derivative, anisic acid, an anisic acid derivative, a benzonitrile, benzothiadiazinone dioxide, a thiocarbamate, a carbamate, a carbanilate, chloropyridinyl, a cyclohexenone derivative, a dinitroaminobenzene derivative, a fluorodinitrotoluidine compound, isoxazolidinone, nicotinic acid, isopropylamine, an isopropylamine derivatives, oxadiazolinone, a phosphate, a phthalate, a picolinic acid compound, a triazine, a triazole, a uracil, a urea derivative, endothall, sodium chlorate, or a combination thereof), a fungicide (e.g., a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof), a molluscicide, an algicide, a plant growth amendment, a bacterial inoculant (e.g., a bacterial inoculant of the genus *Rhizobium*, a bacterial inoculant of the genus *Bradyrhizobium*, a bacterial inoculant of the genus *Mesorhizobium*, a bacterial inoculant of the genus *Azorhizobium*, a bacterial inoculant of the genus *Allorhizobium*, a bacterial inoculant of the genus *Sinorhizobium*, a bacterial inoculant of the genus *Kluyvera*, a bacterial inoculant of the genus *Azotobacter*, a bacterial inoculant of the genus *Pseudomonas*, a bacterial inoculant of the genus *Azospirillium*, a bacterial inoculant of the genus *Bacillus*, a bacterial inoculant of the genus *Streptomyces*, a bacterial inoculant of the genus *Paenibacillus*, a bacterial inoculant of the genus *Paracoccus*, a bacterial inoculant of the genus *Enterobacter*, a bacterial inoculant of the genus *Alcaligenes*, a bacterial inoculant of the genus *Mycobacterium*, a bacterial inoculant of the genus *Trichoderma*, a bacterial inoculant of the genus *Gliocladium*, a bacterial inoculant of the genus *Glomus*, a bacterial inoculant of the genus *Klebsiella*, or a combination thereof), a fungal inoculant (e.g., a fungal inoculant of the family Glomeraceae, a fungal inoculant of the family Claroidoglomeraceae, a fungal inoculant of the family Gigasporaceae, a fungal inoculant of the family Acaulosporaceae, a fungal inoculant of the family Sacculosporaceae, a fungal inoculant of the family Entrophosporaceae, a fungal inoculant of the family Pacidsporaceae, a fungal inoculant of the family Diversisporaceae, a fungal inoculant of the family Paraglomeraceae, a fungal inoculant of the family Archaeosporaceae, a fungal inoculant of the family Geosiphonaceae, a fungal inoculant of the family Ambisporaceae, a fungal inoculant of the family Scutellosporaceae, a fungal inoculant of the family Dentiscultataceae, a fungal inoculant of the family Racocetraceae, a fungal inoculant of the phylum Basidiomycota, a fungal inoculant of the phylum Ascomycota, a fungal inoculant of the phylum Zygomycota, or a combination thereof), or a combination thereof.

The fertilizer can comprise ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesian limestone, magnesia, urea, urea-formaldehydes, urea ammonium nitrate, sulfur-coated urea, polymer-coated urea, isobutylidene diurea, $K_2SO_4$—$(MgSO_4)_2$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, humic acid, or a combination thereof. The agrochemical can comprise any fungicide, bacterial inoculant, or herbicide, as described herein. The spore-forming bacterium, alone or in combination with the insecticide, can further comprise an effective amount of at least one fungicide.

In general, a "fungicide" is a substance to increase mortality or inhibit the growth rate of fungi. The term "fungus" or "fungi" includes a wide variety of nucleated sporebearing organisms that are devoid of chlorophyll. Examples of fungi include yeasts, molds, mildews, rusts, and mushrooms. Typical fungicidal ingredients also include captan, fludioxonil, iprodione, tebuconazole, thiabendazole, azoxystrobin, prochloraz, and oxadixyl. Select compositions, plant seeds, or inoculums according to the disclosure may comprise any natural or synthetic fungicide, such as: aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, boscalid, bromuconazole, bupirimate, buthiobate, calcium polysulphide, capsimycin, captafol, captan, carbendazim, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, dimethirimol, dimethomorph, dimoxystrobin, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluopyram, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxinecopper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, prothiocinazole, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanatemethyl, tioxymid, tolclofos-methyl, tolylfluanid, triadimefon, triadimenol, triazbutil, triazoxide, trichlamide, tricyclazole, tridemorph, trifloxystrobin, triflumizole, triforine, uniconazole, validamycin A, vinclozolin, viniconazole, zarilamide, zineb, ziramor, or a combination thereof. The fungicide can also comprise a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof. One of ordinary skill in the art will readily appreciate that other known synthetic or naturally-occurring fungicides used for agricultural purposes may also be selected for inclusion in a composition, plant seed or inoculum according to the disclosure.

If a composition, plant seed, or inoculum comprises a fungicide, the fungicide can be a foliar fungicide. Foliar fungicides include copper, mancozeb, penthiopyrad, triazoles, cyproconazole, metconazole, propiconazole, prothioconazole, tebuconazole, azoxystrobin, pyraclastobin, fluoxastrobin, picoxystrobin, trifloxystrobin, sulfur, boscalid, thiophanate methyl, chlorothanonil, penthiopyrad, difenconazole, flutriafol, cyprodinil, fluzinam, iprodione, penflufen, cyazofamid, flutolanil, cymoxanil, dimethomorph, pyrimethanil, zoxamide, mandipropamid, metrinam, propamocarb, fenamidone, tetraconazole, chloronab, hymexazol, tolclofos, and fenbuconazole. One of ordinary skill in the art will readily appreciate that other known synthetic or naturally-occurring foliar fungicides used for agricultural purposes may also be selected for inclusion in a composition, plant seed or inoculum according to the disclosure.

Compositions, seeds, and inoculants according to the disclosure comprising an insecticide, possess the ability to increase mortality or inhibit growth rate of insects. As used herein, the term "insects" includes all organisms in the class "Insecta". The term "pre-adult" insects refers to any form of an organism prior to the adult stage, including, for example, eggs, larvae, and nymphs. As used herein, the terms "insecticide" and "insecticidal" also encompass "nematicide" and "nematicidal" and "acaricide" and "acaricidal." "Nematicides" and "nematicidal" refers to the ability of a substance to increase mortality or inhibit the growth rate of nematodes. In general, the term "nematode" comprises eggs, larvae, juvenile and mature forms of said organism. "Acaricide" and "acaricidal" refers to the ability of a substance to increase mortality or inhibit growth rate of ectoparasites belonging to the class Arachnida, sub-class Acari.

According to one aspect of the present disclosure, the at least one insecticide comprises:

(1) Acetylcholinesterase (AChE) inhibitors, such as, for example, carbamates, for example alanycarb, bendiocarb, benfuracarb, butocarboxim, butoxycarboxim, carbofuran, carbosulfan, ethiofencarb, furathiocarb, isoprocarb, metolcarb, oxamyl, pirimicarb, propoxur, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, famphur, fenitrothion, fosthiazate, heptenophos, imicyafos, isofenphos, isopropyl O-(methoxyaminothiophosphoryl) salicylate, isoxathion, malathion, mecarbam, methidathion, mevinphos, monocrotophos, naled, omethoate, parathion-methyl, phenthoate, phorate, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, and triclorfon. (2) GABA-gated chloride channel antagonists, such as, for example, cyclodiene-organochlorines, for example chlordane and/or phenylpyrazoles. (3) Sodium channel modulators/voltage-gated sodium channel blockers such as, for example, pyrethroids, e.g., acrinathrin, allethrin, d-cis-trans allethrin, d-trans allethrin, bifenthrin, bioallethrin, bioallethrin s-cyclopentenyl isomer, bioresmethrin, cycloprothrin, cyhalothrin, lambda-cyhalothrin, gamma-cyhalothrin, empenthrin [(EZ)-(IR)-isomer], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, tefluthrin, tetramethrin, tetramethrin [(1R)-isomer)], and transfluthrin or DDT or methoxychlor. (4) Nicotinergic acetylcholine receptor (nAChR) agonists, such as, for example, neonicotinoids, e.g., dinotefuran, nitenpyram, and thiamethoxam or nicotine or sulfoxaflor. (5) Allosteric activators of the nicotinergic acetylcholine receptor (nAChR) such as, for example, spinosyns, e.g., spinetoram and spinosad. (6) Chloride channel activators, such as, for example, avermectins/milbemycins, for example abamectin, emamectin benzoate, lepimectin and milbemectin. (7) Juvenile hormone imitators such as, for example, juvenile hormone analogues, e.g., hydroprene, kinoprene and methoprene or fenoxycarb or pyriproxyfen. (8) Active compounds with unknown or nonspecific mechanisms of action such as, for example, alkyl halides, e.g., methyl bromide and other alkyl halides; or chloropicrine or sulphuryl fluoride or borax or tartar emetic. (9) Selective antifeedants, for example pymetrozine or flonicamid. (10) Mite growth inhibitors, for example clofentezine, hexythiazox and diflovidazin or etoxazole. (11) Microbial disrupters of the insect gut membrane, for example *Bacillus thuringiensis* subspecies *israelensis*, *Lysinibacillus sphaericus*, *Bacillus thuringiensis* subspecies *aizawai*, *Bacillus thuringiensis* subspecies *kurstaki*, *Bacillus thuringiensis* subspecies *tenebrionis*, and Bt plant proteins: Cry1Ab, Cry1Ac, Cry1Fa, Cry2Ab, mCry3A, Cry3Ab, Cry3Bb, Cry34/35Ab1. (12) Oxidative phosphorylation inhibitors, ATP disrupters such as, for example, diafenthiuron or organotin compounds, for example azocyclotin, cyhexatin and fenbutatin oxide or propargite or tetradifon. (13) Oxidative phosphorylation decouplers acting by interrupting the H proton gradient such as, for example, chlorfenapyr, DNOC and sulfluramid. (14) Nicotinergic acetylcholine receptor antagonists such as, for example, bensultap, cartap hydrochloride, thiocylam, and thiosultap-sodium. (15) Chitin biosynthesis inhibitors, type 0, such as, for example, bistrifluron, chlorfluazuron, diflubenzuron, flucycloxuron, flufenoxuron, hexaflumuron, lufenuron, novaluron, noviflumuron, and teflubenzuron. (16) Chitin biosynthesis inhibitors, type 1, for example buprofezin. (17) Moulting inhibitors (in particular for Diptera, i.e., dipterans) such as, for example, cyromazine. (18) Ecdysone receptor agonists such as, for example, chromafenozide, halofenozide, methoxyfenozide and tebufenozide. (19) Octopaminergic agonists. (20) Complex-III electron transport inhibitors such as, for example, hydramethylnone or acequinocyl or fluacrypyrim. (21) Complex-I electron transport inhibitors, for example from the group of the METI acaricides, e.g., fenazaquin, fenpyroximate, pyrimidifen, pyridaben, tebufenpyrad and tolfenpyrad or rotenone (Derris). (22) Voltage-gated sodium channel blockers, for example indoxacarb or metaflumizone. (23) Inhibitors of acetyl-CoA carboxylase. (24) Complex-IV electron transport inhibitors such as, for example, phosphines, e.g., aluminium phosphide, calcium phosphide, phosphine and zinc phosphide or cyanide. (25) Complex II electron transport inhibitors, such as, for example, cyenopyrafen and cyflumetofen. (26) Ryanodine receptor effectors, such as, for example, diamides, e.g., chlorantraniliprole, which is also known by the trade name RYNAXYPYR™, and cyantraniliprole, or any combination of one or more of the compounds or classes of compounds identified above.

One of ordinary skill in the art will readily appreciate that other known synthetic or naturally-occurring insecticides used for agricultural purposes may also be selected for inclusion in a composition, plant seed or inoculum according to the disclosure.

Screening Methods Using the Endospore Display Platforms Described Herein

The fusion protein constructs and recombinant *Paenibacillus* cells disclosed herein may be used as a platform for high-throughput screening of heterologous proteins that generate new and/or modified plant attributes, as discussed throughout the disclosure. Such attributes may include commercially significant improvements in plant yields and other plant characteristics, such as: altered plant protein or oil content/composition, altered plant carbohydrate content/composition; altered seed carbohydrate content/composition, altered seed oil or protein composition; increased tolerance to environmental or chemical stresses (e.g., resistance to cold or heat, drought, insecticides or herbicides); delayed senescence or disease resistance; growth improvement, health enhancement; herbivore resistance; improved nitrogen fixation or nitrogen utilization; improved root architecture or length; improved water use efficiency; increased biomass; increased seed weight; increased shoot length; increased yield; modified kernel mass or moisture content; metal tolerance; pathogen or pest resistance; photosynthetic capability improvement; salinity tolerance; vigor improvement; increased dry and/or fresh weight of mature seeds, increased number of mature seeds per plant; increased chlorophyll content; a detectable modulation in the level of a metabolite or in the metabolome relative to a reference plant/seed; a detectable modulation in the level of a transcript or in the transcriptome relative to a reference plant/seed; a detectable modulation in the level of a protein or in the proteome relative to a reference plant; and combinations of any of the traits or attributes above. Moreover, the preceding list is intended as a non-limiting set of examples. One of ordinary skill will appreciate that the high-throughput delivery platform disclosed herein is suitable for screening for various other plant traits and attributes discussed elsewhere in the disclosure or otherwise known in the art.

Endospores produced by recombinant *Paenibacillus* cells modified to express a fusion protein according to the disclosure may be applied to plant cells grown in vitro, a host plant seed, seedling, or to a vegetative or otherwise mature plant. The heterologous protein may in turn modify or confer a trait or attribute to the plant cells grown in vitro, host plant seed, seedling or mature plant. In select embodiments, the *Paenibacillus* endospores may be used to inoculate a seed and the resulting new or modified trait or attribute may be immediately apparent, whereas on other embodiments it may not become apparent until a later stage of development of the host plant.

In some embodiments, the *Paenibacillus* bacterium used to deliver the fusion protein is exogenous to the host plant species. In others, the selected *Paenibacillus* bacterium is an endogenous endophyte known to colonize the host plant species. The host plant may be any suitable plant disclosed here (a monocot, dicot, conifer, etc.)

The recombinant *Paenibacillus* bacterium used to deliver the fusion protein may be used to inoculate a host plant seed, seedling, vegetative or otherwise mature plant specimen by way of a coating or spray, or any other method of applying endospores to a host plant known in the art. When applied as a liquid, for example, as a solution or suspension, the *Paenibacillus* endospores may be mixed or suspended in aqueous solutions. Suitable liquid diluents or carriers include aqueous solutions, petroleum distillates, or other liquid carriers. Solid compositions can be prepared by dispersing the *Paenibacillus* endospores in and on an appropriately divided solid carrier, such as peat, wheat, bran, vermiculite, clay, talc, bentonite, diatomaceous earth, fuller's earth, pasteurized soil, and the like. When such formulations comprise wettable powders, dispersing agents such as non-ionic, anionic, amphoteric, or cationic dispersing and emulsifying agents can be used.

*Paenibacillus* endospores may be applied directly to the surface of host plant seeds or to the leaves and stem of a vegetative plant directly, or as part of a composition comprising additional components. The additional components may include one or more compounds that enhance the rate of colonization, compounds that enhance plant growth or health, pesticides or herbicides, or any other compounds disclosed herein as suitable for promoting cultivation and growth of plants. Moreover, the composition may include additional *Paenibacillus* endospores that have been modified to express fusion proteins comprising different amino acid sequences. For example, a composition may comprise a first Paenibacillus endospore that expresses a fusion protein comprising a plant growth promoting factor as well as a second *Paenibacillus* endospore that expresses a fusion protein that comprises a protein that enhances pesticide-resistance.

In select embodiments, the recombinant *Paenibacillus* endospore which is coated onto the seed of a host plant is capable, upon germination of the seed into a vegetative state, of localizing to a different tissue of the plant. For example, the recombinant *Paenibacillus* cells can be capable of localizing to any one of the tissues in the plant, including: the root, adventitious root, seminal root, root hair, shoot, leaf, flower, bud, tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In other embodiments, the recombinant *Paenibacillus* cells may be capable of localizing to the root and/or the root hair of the plant. In alternative embodiments, the recombinant *Paenibacillus* cells may be capable of localizing to the photosynthetic tissues, for example, leaves and shoots of the plant; or to the vascular tissues of the plant, for example, in the xylem and phloem.

In other embodiments, the recombinant *Paenibacillus* cells are capable of localizing to the reproductive tissues (flower, pollen, pistil, ovaries, stamen, fruit) of the plant. In still another embodiment, the recombinant *Paenibacillus* cells colonize a fruit or seed tissue of the plant. In still another embodiment, the recombinant *Paenibacillus* cells are able to colonize the plant such that it is present on the surface of the plant (e.g., the plant exterior or the phyllosphere of the plant). In still other embodiments, the recombinant *Paenibacillus* cells are capable of localizing to substantially all, or all, tissues of the plant.

Compositions comprising the recombinant *Paenibacillus* endospores designed for application to a host plant may comprise a seed coating composition, a root treatment, or a foliar application composition. The seed coating composition, or the root treatment, or the foliar application composition may comprise a fungicide, an antibacterial agent, an herbicide, a nematicide, an insecticide, a plant growth regulator, a nutrient, or combinations thereof. The seed coating composition, or the root treatment, or the foliar application composition can further comprise an agriculturally acceptable carrier, a tackifier, a microbial stabilizer, or a combination thereof. In select embodiments, the seed coating composition, or the root treatment, or the foliar application composition can contain a second bacteria, including but not limited to a rhizobial bacterial preparation. The compositions may also contain a surfactant. In one embodiment, the surfactant is present at a concentration of between 0.01% v/v to 10% v/v. In another embodiment, the surfactant is present at a concentration of between 0.1% v/v to 1% v/v. In some embodiments, the composition may include a microbial stabilizer (e.g., a stabilizer).

Upon inoculation, a treated host plant (e.g., a treated seed, seedling, vegetative or otherwise mature plant) may be screened for the existence of new or modified attributes or traits. Screening can occur at any time point following treatment. In select embodiments, a seed may be treated and screening may not occur until the seed has sprouted or reached a more advanced stage of development. In other embodiments, a seed, seedling or vegetative plant may be treated and screening may not occur until the treated plant has produced a harvested end product which may comprise the sample to be screened for a new or modified trait or attribute.

During screening, various tests may be performed both in vitro and in vivo to determine what benefits, if any, are conferred upon the treated host plant. In vivo screening assays include tests that measure phenotypic traits or attributes of a plant or seed (e.g., assays measuring plant growth rate or height; crop yield; resistance to an environmental stress such as heat, cold, or salinity; resistance to biological pathogens or insect pests; resistance to chemical treatments such as insecticides or herbicides). In vitro screening assays include, but are not limited to, tests that measure the composition or properties of plant extracts, tissue samples, cell samples, and the like. In some embodiments, in vitro screening may comprise purifying and measuring the amount or activity of a given protein, enzyme, gene transcript, metabolite or other compound found in the cells or tissue of the treated host plant. In other embodiments, screening may comprise visual inspection of the structure of cells or tissue of the treated host plant, whether by the naked eye or via microscopy.

In alternative embodiments, screening may comprise assays of recombinant *Paenibacillus* endospores or vegetative cells modified to express a fusion protein according to the present disclosure, as opposed to assays directed to treated host plants. In these embodiments, the *Paenibacillus* family member cells or endospores may be subject to in vitro assays of one or more activities, such as but not limited to the ability to liberate complexed phosphates or complexed iron (e.g., through secretion of siderophores); production of phytohormones; production of antibacterial, antifungal, or insecticidal, or nematicidal compounds; production and/or secretion of ACC deaminase, acetoin, pectinase, cellulase, or RNase. Screening methods directed to the *Paenibacillus* family member cells or endospores, rather than vegetative plants, are particularly advantageous in that such methods may allow detection of useful heterologous proteins sooner than methods directed to treated host plants.

Methods of Identifying Spore Surface Targeting Sequences

The present disclosure discloses several N-terminal spore surface targeting sequences identified in *Paenibacillus*, which are useful as part of a spore surface display platform for heterologous proteins as described herein. However, the disclosure is not limited to these particular sequences, fragments and variants thereof. Screening methods according to the disclosure may be broadly used in *Paenibacillus* and other endospore-forming bacterial genera to identify additional N-terminal spore surface targeting sequences which may be similarly useful as part of an endospore display platform or for other purposes. In one embodiment, the endospore-forming bacterium that are useful for this invention have a hair-like structure that is proteolytically resistant, as shown in FIG. 1. For example, the screening methods disclosed herein may be used to identify N-terminal spore surface targeting sequences in endospore-forming members of *Lysinibacillus, Viridibacillus*, and *Brevibacillus*.

In some exemplary aspects, such sequences may be identified by screening a genome of a *Paenibacillus* or another endospore-forming bacteria of interest for open reading frames ("ORFs") which encode proteins having multiple collagen-like triplet amino acid repeats of "glycine—any residue—any residue" ("GXX repeats") and determining that the protein localizes to the spore surface by microscopy or experimentally. These GXX repeats may be adjacent or separate regions of the polypeptide sequence. In some aspects, polypeptide sequences may be screened for a particular number of adjacent or total GXX repeats (e.g., at least 5, 10, 15, 20, 25 or 30 GXX repeats). In some aspects, the protein localization is determined visually (e.g., using transmission electron microscopy) or experimentally (e.g., using mass spectrometry). In some aspects, methods of identifying an N-terminal targeting sequence may further comprise a step of testing the putative N-terminal targeting sequence by expressing a fusion protein comprising the putative N-terminal targeting sequence and a reporter (e.g., GFP) in a *Paenibacillus* or other bacterial cell.

In some aspects, the disclosure provides spore surface-targeting sequences from *Paenibacillus* and other bacterial genera (e.g., *Lysinibacillus, Viridibacillus*, and *Brevibacillus*) comprising the N-terminal portion of a protein identified via the aforementioned screening process. This N-terminal targeting sequence of such targeting sequences may comprise the first 5, 10, 15, 20, 25, 30, 35, 40, or 50 amino acids of the endogenous sequence, or a fragment or variant thereof. In some aspects, the N-terminal targeting sequence is a variant that is at least 50%, 60%, 70%, 80%, 90% or 95% identical to the endogenous sequence, or a fragment thereof. Spore surface targeting sequences in *Paenibacillus* and other bacterial genera identified according to these methods may be used to generate heterologous fusion proteins according to any of the various embodiments described herein.

The following non-limiting examples are provided to further illustrate the present disclosure.

EXAMPLES

Example 1: General Protocol for Identifying Collagen-Like Spore Surface Proteins Suitable for Endospore Display The complete genome of *Paenibacillus* sp. NRRL B-50972 was searched for ORFs containing collagen-like GXX repeats. Collagen-like spore surface proteins were then visualized by transmission electron microscopy (FIG. 1). The presence of collagen-like spore surface proteins was also experimentally confirmed by mass spectrometry. Briefly, *Paenibacillus* sp. NRRL B-50972 spores were digested with trypsin to remove surface proteins. The spores were removed by centrifugation and the supernatant was analyzed by mass spectrometry to validate the presence of collagen-like spore surface proteins. This general protocol was used to identify endogenous *Paenibacillus* sp. NRRL B-50972 proteins having the N-terminal targeting sequences identified by SEQ ID NOs: 1-10). The same method may be used to identify spore surface proteins from *Viridibacillus, Lysinibacillus* or *Brevibacillus* and corresponding N-terminal targeting sequences.

Example 2: General Protocol for Preparing Recombinant *Paenibacillus* Endospores Displaying Green Fluorescent Protein (GFP)

To create fusion constructs, the gene coding for GFP was fused to a DNA segment encoding the amino acids of the disclosed N-terminal targeting sequence (SEQ ID NO: 1) of *Paenibacillus* sp. NRRL B-50972 under control of the native promoter of the disclosed N-terminal targeting sequences by gene synthesis and cloned into an *E. coli/Paenibacillus* shuttle vector, pAP13. The resulting vector construct was introduced into *Paenibacillus* sp. NRRL B-50972. Correct transformants were then grown in Schaeffer's Sporulation Medium broth at 30° C. until sporulation. *Paenibacillus* sp. NRRL B-50972 spores expressing the fusion construct were then examined by epifluorescent microscopy. GFP is visible on spores expressing the fusion construct (FIG. 2A). *Paenibacillus* sp. NRRL B-50972 spores were also examined by flow cytometry. Spores expressing the fusion construct are significantly more fluorescent then wild-type spores (FIG. 2B).

Example 3. General Protocol for Preparing Recombinant *Paenibacillus* Endospores Displaying an Arbitrary Protein of Interest

*Paenibacillus* cells (e.g., *Paenibacillus* sp. NRRL B-50972) may be cultured, transformed and screened as described above in Example 2 to produce a fusion construct having an N-terminal spore surface targeting sequence according to the disclosure. Screening may proceed by mass spectrometry or any other biochemical or visual means known in the art (e.g., the protein of interest may be tagged with GFP or another selection/screening tag). The N-terminal targeting sequence used to generate the fusion construct may comprise the polypeptide of any of SEQ ID NOs: 2, 4, 6, 8, or 10, 18, 20, 21, 22, 24, 26, 28, 30, or a fragment or variant thereof. In some aspects, the N-terminal targeting sequence may comprise a sequence having one or more residues which correspond to the identical residues in the pairwise alignment of SEQ ID NOs: 2 and 8 (FIG. 3), which is capable of targeting a polypeptide to the spore surface. Similarly, an N-terminal targeting sequence may be used which comprises a sequence having one or more residues which correspond to the identical/conserved residues in the pairwise alignment of SEQ ID NOs: 2 and 8 provided as FIG. 3.

For example, the N-terminal targeting sequence may comprise M-X-V-X-S-T-G-P-I-X-N-X-X-V-X-G-X-R-P-T-X-X-V-T-V-K-I-D-N-R-D-X-V-N-S-S-X-V-L-I-X-G-F-X-L-N-G-X-R-T-L-Y-V-X-X-X-X-X-V-X (SEQ ID NO: 31) (where "X" represents any amino acid), or which comprises any contiguous 5, 10, 15, 20, 25, 30, 35, 40, 45, 50, 55 or 60 residue segment thereof. In another example, the N-terminal targeting sequence may comprise M-X-V-X-S-T-G-P-I-X-N-X-X-V-X-G-X-R-P-T-X-X-V-T-V-K-I-D-N-R-D-X-V-N-S-S-X-V-L-I-X-G-F-X-L-N-G-X-R-T-L-Y-V-X-X-X-X-X-V-X-X-N-X-V-I-T-X-X-X-X-A-X- X-X-X-F-E-F-V-F-T-T-X-X-X-X-E-N-E-X-Q-X-S-V-W-G-K-X-X-X--L-V-X-A-H-R-X-V-S-X-E-L-L-V-X-X-X-X (SEQ ID NO: 32) (where "X" represents any amino acid), or which comprises any contiguous 5, 10, 15, 20, 25, 30, 35, 40, 45, 50, 55, 60, 65, 70, 75, 80, 85, 90, 95, 100, 105, 110, 115, or 120 residue segment thereof.

In some aspects, the selected N-terminal targeting sequence may share at least 60%, 65%, 70%, 75%, 80%, 85%, 90% or 95% sequence identity with these sequences and remain capable of targeting the fusion construct to the spore surface.

Example 4: Methods for Delivering a Fusion Protein Involved in the Production of a Plant Growth Promoting Compound to a Seed, Seedling, Plant, or Plant Part Using Recombinant *Paenibacillus* Endospores Enzymes responsible for the production of plant growth promoting compounds can be delivered to plants using the *Paenibacillus* endospore delivery system disclosed herein. For example, butanediol dehydrogenase converts acetoin to 2,3-butanediol. 2,3-butanediol is a plant growth promoting compound. *Paenibacillus* endospores expressing this enzyme can be applied as a seed treatment or seed coating or delivered to the area surrounding a seed, seedling, plant, or plant part by drip or spray.

Example 5: Methods for Delivering Multiple Fusion Proteins on a Single *Paenibacillus* Endospore to a Seed, Seedling, Plant, or Plant Part Using Recombinant *Paenibacillus* Endospores A single recombinant *Paenibacillus* endospore can be used to display more than one heterologous fusion protein. This is accomplished by constructing two (or more) separate fusion proteins. The coding sequence for each heterologous protein to be displayed on the *Paenibacillus* endospore surface is fused separately to an N-terminal targeting sequence under control of its native promoters. The fusion protein constructs can be cloned either into the same plasmid vector or different plasmid vectors and introduced into a *Paenibacillus* member by electroporation. The resulting *Paenibacillus* endospores will then express a mixture of both heterologous proteins on the spore surface. This is particularly useful for stacking multiple proteinaceous invertebrate toxins to mitigate pest resistance.

Example 6: Methods for Providing One or More Different Fusion Proteins to a Seed, Seedling, Plant, or Plant Part Using a Combination of Multiple Recombinant *Paenibacillus* Endospores, Each Displaying One or More Different Fusion Proteins In certain cases, delivery of more than one *Paenibacillus* endospore in combination each expressing one or more different heterologous proteins (as described above) are provided. For example, the delivery of nitrogen fixation enzymes to the area surrounding the roots of a plant reduces the need for chemical nitrogen fertilizers. Nitrogen fixation in bacteria may require, at minimum, eight or nine different enzymes and potentially upwards of twenty different enzymes depending on the species. Here, delivery of a combination of *Paenibacillus* endospores each expressing different enzyme components of the nitrogen fixation pathway may useful. For example, *Paenibacillus* endospores heterologously displaying NifH, NifD, and NifK may be combined in a mixture with *Paenibacillus* endospores heterologously displaying NifE, NifN, and NifD and delivered to the area surrounding the roots.

Example 7: Methods for Delivering an Invertebrate Toxin that Kills Invertebrate Plant Pests to the Area Surrounding a Seed, Seedling, Plant, or Plant Part or as a Seed Treatment Using Recombinant *Paenibacillus* Endospores Proteinaceous toxins antagonistic towards invertebrates including but not limited to insects or nematodes can be delivered using the *Paenibacillus* endospore system. For example, Cry toxins including but not limited to Cry5B and Cry21A which are both insecticidal and nematicidal may be fused to the N-terminal targeting sequence for expression in *Paenibacillus* endospores. *Paenibacillus* endospores expressing Cry toxins or other proteinaceous invertebrate toxins can be applied as a seed treatment or seed coating or delivered to the area surrounding a seed, seedling, plant, or plant part by drip or spray for protection against invertebrate plant pathogens.

Example 8: Methods for Delivering a Peptide, Protein, or Enzyme that is Antagonistic Towards Bacterial Plant Pests to the Area Surrounding a Seed, Seedling, Plant, or Plant Part or as a Seed Treatment Using *Paenibacillus* Endospores Bacteriocins are small peptides produced by bacteria with antagonistic activity towards other bacteria. Due to the fact that bacteriocins are ribosomally synthesized as opposed to other antimicrobial molecules (e.g., bacitracin), which are synthesized by large non-ribosomal peptide synthetases, bacteriocins are especially well suited for delivery using the *Paenibacillus* endospore system. The coding sequence for one or more bacteriocins may be fused to the N-terminal targeting sequence for expression in *Paenibacillus* endospores. *Paenibacillus* endospores expressing bacteriocins can be applied as a seed treatment or seed coating or delivered to the area surrounding a seed, seedling, plant, or plant part by drip or spray for protection against bacterial plant pathogens.

Example 9: Methods for Delivering a Peptide, Protein, or Enzyme that is Antagonistic Towards Fungal Plant Pests to the Area Surrounding a Seed, Seedling, Plant, or Plant Part or as a Seed Treatment Using *Paenibacillus* Endospores The primary cell wall component of fungi is chitin. Chitinase is an enzyme that degrades chitin and can be expressed on the surface of *Paenibacillus* endospores to protect against fungal plant pathogens by destroying their cell walls. *Paenibacillus* endospores expressing chitinase can be applied as a seed treatment or seed coating or delivered to the area surrounding a seed, seedling, plant, or plant part by drip or spray.

Example 10: Methods for Delivering an Enzyme that Degrades or Modifies a Bacterial, Fungal, or Plant Nutrient Source to the Area Surrounding a Seed, Seedling, Plant, or Plant Part or as a Seed Treatment Using *Paenibacillus* Endospores Enzymes responsible for the degradation or modification of a bacterial, fungal, or plant nutrient source can be delivered to plants using recombinant *Paenibacillus* endospores. For example, a glycoside hydrolase which breaks down complex polysaccharides can be used to make available simple sugars for beneficial rhizobacteria by treating a plant or seed with recombinant *Paenibacillus* endospores expressing this (or another) enzyme of interest.

Example 11: Methods for Assessing Responses to Plant Growth Promoting Biocontrol Agents by Screening of Genomic DNA Libraries Derived from Plant Growth Promoting Biocontrol Agents Using *Paenibacillus* Endospores Many of the biocontrol strains used today are recalcitrant to exogenous DNA uptake rendering researchers unable to generate targeted genetic modifications of said strains. Due to this challenge, elucidating the mechanism of action of the plant growth promoting effects of these biocontrol strains is incredibly difficult. *Paenibacillus* endospores present a novel approach for identifying specific genes responsible for the underlying plant growth promoting effects of biocontrol strains. First, the N-terminal targeting sequence and native promoter are cloned into a suitable *E. coli/Bacillus* shuttle vector (e.g., pHP13), resulting in a vector suitable for heterologous protein expression on *Paenibacillus* endospores. All cloning steps and plasmid propagation are performed in *E. coli*. Next, total gDNA is extracted from a target plant growth promoting biocontrol strain. The gDNA is sheared into fragments (enzymatically or sonically) and ligated into the above described vector for expression of heterologous proteins on *Paenibacillus* endospores to generate a gDNA library comprised of all the genetic material originating from the biocontrol strain of interest. The resulting vector library is introduced into a *Paenibacillus* member by electroporation and the bacteria are plated onto agar plates containing an appropriate antibiotic selection agent to select for *Paenibacillus* endospore transformants. Individual *Paenibacillus* endospore transformants each expressing a different fragment of the target biocontrol strain's gDNA are assessed for plant growth promoting effects. These effects can include but are not limited to enhanced greening, improved germination, increased plant vigor, increased root length, increased root mass, increased plant height, increased leaf area, or resistance to pests. The vector in *Paenibacillus* endospore transformants found to modulate the above mentioned plant health parameters can be sequenced to identify the genetic determinants originating from the biocontrol strain responsible for the observed plant growth promoting effects.

Example 12: Methods for Identifying Novel or Uncharacterized Toxins Antagonistic Against Plant Invertebrate, Bacterial, and Fungal Plant Pathogens Using *Paenibacillus* Endospores Many of the biocontrol strains in use today are recalcitrant to exogenous DNA uptake rendering researchers unable to generate targeted genetic modifications of said strains. Due to this challenge, elucidating the mechanism of action by which biocontrol strains are toxic towards invertebrate, bacterial, and fungal plant pathogens is incredibly difficult. *Paenibacillus* endospores present a novel approach for identifying specific genes responsible for the underlying plant protective effects of biocontrol strains. First, the N-terminal targeting sequence and native promoter are cloned into a suitable *E. coli/Bacillus* shuttle vector (e.g., pHP13) resulting in a vector suitable for heterologous protein expression on *Paenibacillus* endospores. All cloning steps and plasmid propagation are performed in *E. coli*. Next, total gDNA is extracted from a target plant growth promoting biocontrol strain. The gDNA is sheared into fragments (enzymatically or sonically) and ligated into the above described vector for expression of heterologous proteins on *Paenibacillus* endospores to generate a gDNA library comprised of all the genetic material originating from the biocontrol strain of interest. The resulting vector library is introduced into a *Paenibacillus* member by electroporation and the bacteria are plated onto agar plates containing an appropriate antibiotic selection agent to select for *Paenibacillus* endospore transformants Individual *Paenibacillus* endospore transformants each expressing a different fragment of the target biocontrol strain's gDNA are assessed for antagonist activity towards invertebrate, bacterial, and fungal plant pathogens. The vector in *Paenibacillus* endospore transformants that are found to be antagonistic towards the above plant pathogens can be sequenced to identify the genetic determinants originating from the biocontrol strain responsible for the observed plant protective effects.

Example 13: Methods for Treating a Seed, Seedling, Plant, or Plant Part for the Purposes of Protecting Plants from Pathogens or Improving Plant Health Using Non-Viable *Paenibacillus* Endospores There may be a need to deliver plant health promoting proteins/enzymes or plant protection proteins/enzymes using the *Paenibacillus* endospore delivery system with non-viable (dead) *Paenibacillus* endospores. *Paenibacillus* endospores can be inactivated and rendered non-viable via sufficient heat treatment, UV light, gamma irradiation, or high-pressure processing. The resulting non-viable *Paenibacillus* endospores can be applied as a seed treatment or seed coating or delivered to the area surrounding a seed, seedling, plant, or plant part by drip or spray.

Example 14. General Protocol for Preparing Recombinant *Paenibacillus* Endospores Displaying Beta-Galactosidase (B-Gal) from *Escherichia coli*

To create fusion constructs, the gene coding for β-gal was fused to a DNA segment encoding the amino acids of the disclosed N-terminal targeting sequence (SEQ ID NO: 1) of *Paenibacillus* sp. NRRL B-50972 under control of the native promoter of the disclosed N-terminal targeting sequences by gene synthesis and cloned into an *E. coli/Paenibacillus* shuttle vector derived from the pMiniMad vector described in Patrick, J E and Kearns, D B. 2008. MinJ (YvjD) is a Topological Determinant of Cell Division in *Bacillus subtilis*. Molecular Microbiology. 70: 1166-1179. The resulting vector construct was introduced into a *Paenibacillus polymyxa* strain (Strain 1) by electroporation similar to that described by Kim and Timmusk (2013), "A Simplified Method for Gene Knockout and Direct Screening of Recombinant Clones for Application in *Paenibacillus polymyxa*," PLoSONE, 8(6): e68092, doi: doi:10.1371/journal-.pone.0068092. A control was also prepared that contained the shuttle vector without the targeting sequence. Correct transformants were then grown in Schaeffer's Sporulation Medium broth at 30° C. until sporulation. The resulting culture was centrifuged to separate supernatant from spores. *Paenibacillus polymyxa* spores expressing the fusion construct or containing the empty shuttle vector only and corresponding supernatant were then examined by in vitro assay. β-gal is functional on spores expressing the fusion construct based on hydrolysis of 5-bromo-4-chloro-3-indolyl-β-D-galacto-pyranoside (X-Gal). Results are shown below in Table 3.

TABLE 3

Beta-galactosidase activity of supernatants and spores.

| Sample | X-Gal Hydrolysis[a] |
| --- | --- |
| *P. polymyxa* empy shuttle vector supernatant | − |
| *P. polymyxa* N-terminal targeting sequence-β-galactosidase supernatant | − |
| *P. polymyxa* empy shuttle vector spores | − |
| *P. polymyxa* N-terminal targeting sequence-β-galactosidase-pAP13 spores | + |

[a]X-gal hydrolysis was scored as (−) for no color or (+) for blue color denoting hydrolysis of X-gal by β-galactosidase.

Example 15. General Protocol for Preparing Recombinant *Paenibacillus* Endospores Displaying Vegetative Insecticidal Protein 3 (Vip3) from *Bacillus thuringiensis* (SEQ ID NO: 17)

To create fusion constructs, the gene coding for vip3 (SEQ ID NO: 16) was fused to a DNA segment encoding the amino acids of the disclosed N-terminal targeting sequence (SEQ ID NO: 1) of *Paenibacillus* sp. NRRL B-50972 by Gibson Assembly into the *E. coli/Paenibacillus* shuttle vector described in Example 14. Expression of the fusion is under control of the native promoter of the disclosed N-terminal targeting sequence. The resulting vector construct was introduced into a *Paenibacillus polymyxa* strain (Strain 1) by electroporation, as described above. Correct transformants were then grown in Schaeffer's Sporulation Medium broth at 30° C. until sporulation.

Example 16. Activity of the *Paenibacillus polymyxa* Strain Expressing Vip3 Against *Spodoptera exigua*

The insecticidal activity of the *Paenibacillus polymyxa* strain expressing Vip3, from Example 15, was evaluated against *Spodotera exigua* (beet armyworm). A 96-well plate assay was performed to test the insecticidal activity of each *Paenibacillus polymyxa* strain including an empty vector control and an active cargo (SEQ ID NO: 2-Vip3). Spores of the strains were produced by growing the strains in Schaeffer's Sporulation Medium broth until sporulation and centrifuging the resulting whole broth culture to separate spores from supernatant. The spore samples from the strains were then applied to 96-well microplates containing an agar substrate similar to that described in Marrone et al., (1985), "Improvements in Laboratory Rearing of the Southern Corn Rootworm, *Diabrotica undecimpuncta howardi* Barber (Coleoptera: Chrysomelidae), on an Artificial Diet and Corn," J. Econ. Entomol., 78: 290-293. The spore samples were then diluted in water and applied at concentrations of 100%, 33%, 11%, 3.7%, and 1.2% to the plates.

After the treatments had been allowed to dry, about 20 eggs from *Spodotera exigua* (beet armyworm) were added to each well. Several days later, the insecticidal activity was determined by evaluating the stunting scores and mortality scores of the treated larvae. Insect stunting scores were rated according to the following scale: 1=severely stunted; 2=highly stunted, minimal growth; 3=slightly smaller than untreated control; 4=same size as untreated control. The insect mortality score is based on the following scale: 4=0-25% mortality, 3=26-50% mortality, 2=51-79% mortality, 1=80-100% mortality.

*Spodotera exigua* larvae treated with 11% *Paenibacillus* spores expressing targeted Vip3 (i.e., SEQ ID NO: 2-Vip3) experienced 2-fold greater stunting thant those treated with the same concentration of *Paenibacillus* spores expressing the empty vector (see Table 4). Similarly, larvae treated with 11% *Paenibacillus* spores expressing the targeted Vip3 experienced 1.5-fold greater mortality than those treated with the same concentration of *Paenibacillus* spores expressing the empty vector (see Table 5).

TABLE 4

Stunting ratings of treated *Spodotera exigua* (beet armyworm).

| | Stunting Score | | | |
| --- | --- | --- | --- | --- |
| | SEQ ID NO: 2-Vip3 | | Empty Vector | |
| Application Rate | Mean | Std Err | Mean | Std Err |
| 1 | 1 | 0 | 1 | 0 |
| 0.33 | 1 | 0 | 1.7 | 0.7 |
| 0.11 | 1.5 | 0.5 | 3 | 1 |
| 0.037 | 3.3 | 0.7 | 4 | 0 |
| 0.012 | 4 | 0 | 4 | 0 |

TABLE 5

Mortality ratings of treated *Spodotera exigua* (beet armyworm).

| | Mortality Score | | | |
|---|---|---|---|---|
| | SEQ ID NO: 2-Vip3 | | Empty Vector | |
| Application Rate | Mean | Std Err | Mean | Std Err |
| 1 | 1 | 0 | 1 | 0 |
| 0.33 | 1 | 0 | 1.3 | 0.3 |
| 0.11 | 1.5 | 0.5 | 2.3 | 0.9 |
| 0.037 | 3.7 | 0.3 | 4 | 0 |
| 0.012 | 4 | 0 | 4 | 0 |

Unless defined otherwise, all technical and scientific terms herein have the same meaning as commonly understood by one of ordinary skill in the art to which this invention belongs. All publications, patents, and patent publications cited are incorporated by reference herein in their entirety for all purposes.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

We claim:

1. A method for identifying an N-terminal signal sequence that is capable of targeting a protein to a spore surface of an endospore-forming bacterium, comprising:
   screening a genome of the endospore-forming bacterium for at least one open reading frame which encodes a protein having multiple collagen-like triplet repeats having the sequence "GXX" wherein "X" represents "any amino acid";
   determining that at least one of the proteins identified in the screening step localizes to the spore surface of the endospore-forming bacterium by microscopy or experimentally; and
   identifying a putative N-terminal signal sequence from at least one protein identified in the determining step as localizing to the spore surface and expressing in the endospore-forming bacterium a fusion protein comprising the putative N-terminal signal sequence and a reporter gene.

2. The method of claim 1, wherein the endospore-forming bacterium includes a hair-like structure that is proteolytically resistant.

3. The method of claim 1, further comprising selecting the fusion protein based on expression of the fusion protein on the spore surface.

4. The method of claim 1, further comprising replacing the reporter gene in the fusion protein that is selected with a nucleotide sequence of interest to create a second fusion protein and expressing the second fusion protein in the endospore-forming bacterium.

5. The method of claim 1, wherein the bacterium is a member of the genus *Paenibacillus, Viridibacillus, Brevibacillus* or Lysinibacillus.

6. The method of claim 5, wherein the bacterium is a member of the genus *Paenibacillus*.

7. The method of claim 1, wherein localization is determined using transmission electron microscopy and/or mass spectrometry.

* * * * *

SEQUENCE LISTING

```
<160> NUMBER OF SEQ ID NOS: 32

<210> SEQ ID NO 1
<211> LENGTH: 357
<212> TYPE: DNA
<213> ORGANISM: Paenibacillus sp. NRRL B-50972

<400> SEQUENCE: 1
atggtagtat tatctactgg acctattgca aacgatcctg ttctaggagt cagacccacc     60
caactggtca cagtaaaaat agataaccga gattctgtaa attcttctat cgttttgatc    120
gagggtttta ttttaaacgg tagcagaaca ttatatgtac aacaattagt ggtagtggga    180
ccaaatgcgg ttataacgag gaatttcttt gcaaatgtag acgcatttga attcgttttt    240
accactagcg gaccagcaga gaatgaaact caaatttctg tttggggtaa agatgcattg    300
gggcaattag tacctgccca tcggttagta tctgacgaac ttttaggaac cgatcga       357

<210> SEQ ID NO 2
<211> LENGTH: 119
<212> TYPE: PRT
<213> ORGANISM: Paenibacillus sp. NRRL B-50972

<400> SEQUENCE: 2

Met Val Val Leu Ser Thr Gly Pro Ile Ala Asn Asp Pro Val Leu Gly
1               5                   10                  15

Val Arg Pro Thr Gln Leu Val Thr Val Lys Ile Asp Asn Arg Asp Ser
            20                  25                  30

Val Asn Ser Ser Ile Val Leu Ile Glu Gly Phe Ile Leu Asn Gly Ser
        35                  40                  45

Arg Thr Leu Tyr Val Gln Gln Leu Val Val Val Gly Pro Asn Ala Val
    50                  55                  60

Ile Thr Arg Asn Phe Phe Ala Asn Val Asp Ala Phe Glu Phe Val Phe
65                  70                  75                  80

Thr Thr Ser Gly Pro Ala Glu Asn Glu Thr Gln Ile Ser Val Trp Gly
                85                  90                  95

Lys Asp Ala Leu Gly Gln Leu Val Pro Ala His Arg Leu Val Ser Asp
            100                 105                 110

Glu Leu Leu Gly Thr Asp Arg
        115

<210> SEQ ID NO 3
<211> LENGTH: 231
<212> TYPE: DNA
```

<213> ORGANISM: Paenibacillus sp. NRRL B-50972

<400> SEQUENCE: 3

```
atgcctgcct tggatgaatg gagtagtata caacaaatcg atatggaggt gtttgtattg    60
ggtcgtcccg aattgaaacg aaagaaaggc cgtaaaaaag acgtttttat ccgctcttgg   120
tttagtaaaa acgtccgaa gagaaaatgc cattcgaaac gaaagtgctt ttgcaaggaa   180
atcgtcgtca gaaagcaaat cgtccgtgta aatatacctc aaaatgtttt a           231
```

<210> SEQ ID NO 4
<211> LENGTH: 77
<212> TYPE: PRT
<213> ORGANISM: Paenibacillus sp. NRRL B-50972

<400> SEQUENCE: 4

```
Met Pro Ala Leu Asp Glu Trp Ser Ser Ile Gln Gln Ile Asp Met Glu
1               5                   10                  15

Val Phe Val Leu Gly Arg Pro Glu Leu Lys Arg Lys Lys Gly Arg Lys
            20                  25                  30

Lys Asp Val Phe Ile Arg Ser Trp Phe Ser Lys Lys Arg Pro Lys Arg
        35                  40                  45

Lys Cys His Ser Lys Arg Lys Cys Phe Cys Lys Glu Ile Val Val Arg
    50                  55                  60

Lys Gln Ile Val Arg Val Asn Ile Pro Gln Asn Val Leu
65                  70                  75
```

<210> SEQ ID NO 5
<211> LENGTH: 438
<212> TYPE: DNA
<213> ORGANISM: Paenibacillus sp. NRRL B-50972

<400> SEQUENCE: 5

```
atgaaacaca gaaaaccgtt caggttcagt ggtgcttcaa aaaagacga ggactgcaaa     60
ccacctaaaa ttagcagaga acggaagaa cttctcaaac tgattaagga attagtcgcc   120
atcatcccgc tcgttttcgc aaacccgtct gtggctaatg taacttcatt gcaacagatt   180
ttacagcgat tattagctct cgcaaataaa ttgagactta gaggctcggc taagacagat   240
ttattagcgg cgttggaact ggctatcgtg gcgtcggaag ccactctttt ctccccgatc   300
ggtgttggaa cgacactgca caactgctg gaagtcttat tgtctattat tttgcaggaa   360
ccccttgatc ctgctcttaa agacagtttg atcagtgcaa tcagaaatgc cgaaacggct   420
atcagtattg cgttgggt                                                  438
```

<210> SEQ ID NO 6
<211> LENGTH: 146
<212> TYPE: PRT
<213> ORGANISM: Paenibacillus sp. NRRL B-50972

<400> SEQUENCE: 6

```
Met Lys His Arg Lys Pro Phe Arg Phe Ser Gly Ala Ser Lys Lys Asp
1               5                   10                  15

Glu Asp Cys Lys Pro Pro Lys Ile Ser Arg Glu Thr Glu Glu Leu Leu
            20                  25                  30

Lys Leu Ile Lys Glu Leu Val Ala Ile Ile Pro Leu Val Phe Ala Asn
        35                  40                  45

Pro Ser Val Ala Asn Val Thr Ser Leu Gln Gln Ile Leu Gln Arg Leu
    50                  55                  60
```

```
Leu Ala Leu Ala Asn Lys Leu Arg Leu Arg Gly Ser Ala Lys Thr Asp
 65                  70                  75                  80

Leu Leu Ala Ala Leu Glu Leu Ala Ile Val Ala Ser Glu Ala Thr Leu
                 85                  90                  95

Phe Ser Pro Ile Gly Val Gly Thr Thr Leu Gln Gln Leu Leu Glu Val
            100                 105                 110

Leu Leu Ser Ile Ile Leu Gln Glu Pro Leu Asp Pro Ala Leu Lys Asp
        115                 120                 125

Ser Leu Ile Ser Ala Ile Arg Asn Ala Glu Thr Ala Ile Ser Ile Ala
    130                 135                 140

Leu Gly
145

<210> SEQ ID NO 7
<211> LENGTH: 360
<212> TYPE: DNA
<213> ORGANISM: Paenibacillus sp. NRRL B-50972

<400> SEQUENCE: 7
atggcggtta tatcaactgg acccatagaa ataattatg tcagtggtat tcggcctact    60
catcgagtta ccgtgaaaat tgataatcgt gatactgtga attcttctac ggtattgatt   120
cagggttttt atctaaatgg tacaagaacg ttatatgtgc ttgattttat aactgtaaat   180
tcaaatgaag tgattacaaa agattattat gctgatttta attcatttga gtttgttttt   240
accactgaaa gtgttacaga aaatgagatt caagtttcag tctggggtaa aaattcaatg   300
gggcagttag tgacagctca ccgtgttgta tcttccgaat gcttgtagc aaaaggcgcg    360

<210> SEQ ID NO 8
<211> LENGTH: 120
<212> TYPE: PRT
<213> ORGANISM: Paenibacillus sp. NRRL B-50972

<400> SEQUENCE: 8

Met Ala Val Ile Ser Thr Gly Pro Ile Glu Asn Asn Tyr Val Ser Gly
 1               5                  10                  15

Ile Arg Pro Thr His Arg Val Thr Val Lys Ile Asp Asn Arg Asp Thr
            20                  25                  30

Val Asn Ser Ser Thr Val Leu Ile Gln Gly Phe Tyr Leu Asn Gly Thr
        35                  40                  45

Arg Thr Leu Tyr Val Leu Asp Phe Ile Thr Val Asn Ser Asn Glu Val
    50                  55                  60

Ile Thr Lys Asp Tyr Tyr Ala Asp Phe Asn Ser Phe Glu Phe Val Phe
 65                  70                  75                  80

Thr Thr Glu Ser Val Thr Glu Asn Glu Ile Gln Val Ser Val Trp Gly
                 85                  90                  95

Lys Asn Ser Met Gly Gln Leu Val Thr Ala His Arg Val Val Ser Ser
            100                 105                 110

Glu Leu Leu Val Ala Lys Gly Ala
        115                 120

<210> SEQ ID NO 9
<211> LENGTH: 330
<212> TYPE: DNA
<213> ORGANISM: Paenibacillus sp. NRRL B-50972

<400> SEQUENCE: 9
ttgggaaatt tattgttgcg taaaagatat cgcttgaccc aggtggcaag gaaaaaaaag    60
```

```
aaggaaagag atcaaaagat gggagcgttc cgttttatgc ccatttatcg tacaggaacg    120
agctgcattc gtaacaaaaa gggaaataaa cgtatttata acagggtag aagaagagag    180 agaatatgcg cttatagaca tcatttgcac gctgagcggg tgccctcagg tttatcaaat   240
aaaaaaatct gttttatgaa attcaaaggt caacgaagac tgcgaggcgg cgaacaggag    300
cctcaaggca attcaggagg agcagttcaa                                    330
```

<210> SEQ ID NO 10
<211> LENGTH: 110
<212> TYPE: PRT
<213> ORGANISM: Paenibacillus sp. NRRL B-50972

<400> SEQUENCE: 10

```
Leu Gly Asn Leu Leu Arg Lys Arg Tyr Arg Leu Thr Gln Val Ala
1               5                   10                  15

Arg Lys Lys Lys Glu Arg Asp Gln Lys Met Gly Ala Phe Arg Phe
            20                  25                  30

Met Pro Ile Tyr Arg Thr Gly Thr Ser Cys Ile Arg Asn Lys Lys Gly
        35                  40                  45

Asn Lys Arg Ile Tyr Arg Gln Gly Arg Arg Glu Arg Ile Cys Ala
50                  55                  60

Tyr Arg His His Leu His Ala Glu Arg Val Pro Ser Gly Leu Ser Asn
65                  70                  75                  80

Lys Lys Ile Cys Phe Met Lys Phe Lys Gly Gln Arg Arg Leu Arg Gly
                85                  90                  95

Gly Glu Gln Glu Pro Gln Gly Asn Ser Gly Gly Ala Val Gln
            100                 105                 110
```

<210> SEQ ID NO 11
<211> LENGTH: 200
<212> TYPE: DNA
<213> ORGANISM: Paenibacillus sp. NRRL B-50972

<400> SEQUENCE: 11

```
gaaacgggag tggtgaaatc attgatgctc agcgcattgt tgcggatgag caactagatt    60
cttgaaacac aacatatgta cagagataga accacaatcg taacaaatgg ttgagacata   120
aaatagaggg aacaggatct tgagaaagat ctcattgttc acaaaaaagc ttgattttac    180
tagaaaggag ggagtatcca                                               200
```

<210> SEQ ID NO 12
<211> LENGTH: 200
<212> TYPE: DNA
<213> ORGANISM: Paenibacillus sp. NRRL B-50972

<400> SEQUENCE: 12

```
ctatatacat gcgcaaaaaa cggcttcaaa ctgcttcata attacggcac gtttcttctg    60
gcgccttcgg ctgttccttg gtgtgaacca aggtaacagc cggggcgct attttatat    120 aactagatga atgtacctgt acaaagaccc attttatcc aaaattagat cattgcctat   180
caaccacagg acagatgtcc                                               200
```

<210> SEQ ID NO 13
<211> LENGTH: 200
<212> TYPE: DNA
<213> ORGANISM: Paenibacillus sp. NRRL B-50972

<400> SEQUENCE: 13

```
agcgttacaa gttggaagcc cggtttggaa atacagaaaa tcgatattaa agcttatgta     60
caagcatcca ataataattc ttgtgtggtg attcaccctt ttcgcttcag taaatatatt    120
gttaatatct gcgaaacggg gcgatgatcc acctgtcacc tctacagtag ggagaaatgt    180
gaaggaggag atatttgaac                                                200
```

```
<210> SEQ ID NO 14
<211> LENGTH: 200
<212> TYPE: DNA
<213> ORGANISM: Paenibacillus sp. NRRL B-50972

<400> SEQUENCE: 14
agcggtattt tttgtgcccc acaaaaaagg ctcccttatc aaaaggggtt tttatcacat     60
aggaaatgtc cacacgtata tatagatgtt acatattata taaatcgtga acattcgaat    120
ctcaatacta gttatagaag aggtggcatt agtgatagga ttatagcttc gttactttag    180
acaaaaggag aatccaatat                                                200
```

```
<210> SEQ ID NO 15
<211> LENGTH: 200
<212> TYPE: DNA
<213> ORGANISM: Paenibacillus sp. NRRL B-50972

<400> SEQUENCE: 15
atttattttt ttgaaaaatt acaggggatt cagtcccact ttcagtaaat tcagaaagaa     60
aaataatgta acggcgaaat ggaagtgagc attaaaaatt tatttttttg gaaaaaaatt    120
taaggaggtc atctgtccaa tcaggttcgt ttagattcca taagataatg aaactgtact    180
taattatgga ggtgtcagta                                                200
```

```
<210> SEQ ID NO 16
<211> LENGTH: 2370
<212> TYPE: DNA
<213> ORGANISM: Bacillus thuringiensis

<400> SEQUENCE: 16
atgaacaaaa acaacactaa attatctact cgtgctcttc catctttcat tgactacttc     60
aacggtattt acggtttcgc tacaggtatc aaagacatta tgaacatgat cttcaaaact    120
gatactggtg gtgacttaac tcttgatgaa attcttaaga accaacaatt acttaacgac    180
atctctggta aacttgatgg tgttaacggt tctcttaacg acttaatcgc acaaggtaac    240
cttaacactg aactaagcaa agaaatccta aaaattgcta atgaacaaaa ccaagttctt    300
aatgatgtta acaacaaact agacgctatt aacactatgt tacgtgtata ccttccaaaa    360
atcacttcaa tgctttctga tgttatgaaa caaaactacg ctttatcttt acaaatcgaa    420
tacttatcta agcaattaca ggaaatctct gataaattag acatcatcaa cgttaacgta    480
ttaattaaca gcactcttac agaaattacg ccagcttacc aacgtatcaa atacgttaat    540
gaaaaattcg aagaacttac attcgctact gaaacttctt ctaaagttaa aaaagacggt    600
tctcctgctg atattttaga tgaattaact gaattaactg aacttgctaa atctgtaact    660
aaaaacgatg ttgacggttt cgaattctac cttaacactt tccacgatgt aatggtaggc    720
aacaaccttt tcggtcgctc tgctcttaaa actgctagtg aattaatcac taaagaaaac    780
gttaaaactt ctggtagcga agtaggtaac gtttacaatt tcttaatcgt actaacagct    840
cttcaagcac aagcattcct tactcttact acttgccgta aattacttgg tttagctgat    900
```

-continued

```
attgattaca cttctatcat gaacgaacat cttaacaaag aaaaagaaga attccgtgtt      960
aatatccttc cgacattatc taacactttt tctaacccaa attacgctaa ggttaaaggt     1020
agcgatgaag atgcaaaaat gatcgtagaa gctaaaccag gtcacgcatt aatcggtttc     1080
gagatctcaa acgacagcat cacagtttta aaagtttatg aagctaaact taaacaaaac     1140
taccaagtag ataaagacag cctgtctgaa gttatctacg gtgacatgga taaattatta     1200
tgtccagatc aaagtgaaca aatctactac actaataaca tcgtattccc aaacgaatat     1260
gtaatcacta aaatcgattt cacaaagaaa atgaaaactc ttcgttacga ggtaactgct     1320
aacttttacg attcatctac tggtgaaatt gatcttaaca agaaaaaagt tgaatcttct     1380
gaagctgaat accgtacatt atctgctaac gatgatggtg tttatatgcc tttaggtgta     1440
atttctgaaa cattcttaac tcctatcaac ggtttcggtc ttcaagctga tgaaaactct     1500
cgcttaatca ctttaacatg caaatcttac cttcgcgaac ttttattagc tacagattta     1560
tctaacaaag aaactaaact tattgttcct ccatctggat tcattagcaa tatcgttgag     1620
aacggtagca ttgaagaaga taaccttgaa ccttggaaag ctaacaacaa aaacgcatac     1680
gttgatcata caggtggtgt taacggtaca aaagctcttt acgtacacaa agatggtggt     1740
attagccaat catcggcga caaattaaag ccaaaaactg aatacgttat ccaatacact     1800
gtaaaaggta accatcaat tcatttaaaa gatgaaaata ctggttacat tcattacgaa     1860
gacactaaca caaccttga agattaccaa acaatcaaca aacgttttac aacaggaact     1920
gacttaaaag gtgttactt aattttaaaa tctcaaaacg gtgacgaggc atggggcgac     1980
aacttcatca ttctagaaat ttctccttct gaaaaattac tttctcctga attaatcaat     2040
actaacaact ggacttctac aggttctact aacatttctg gaaacacttt aacactttac     2100
caaggtggtc gtggtatctt aaaacaaaac ttacaattag attcattctc tacataccgt     2160
gtttatttct ctgtatctgg tgacgctaac gtacgtatcc gtaactctcg tgaagtatta     2220
tttgaaaaac gttacatgtc aggagctaaa gatgtatctg aaatgttcac tactaaattc     2280
gaaaagata atttctacat tgaattatct caaggtaaca accttacgg tggtccaatc     2340
gttcacttct acgatgtttc tatcaaataa                                      2370
```

<210> SEQ ID NO 17
<211> LENGTH: 789
<212> TYPE: PRT
<213> ORGANISM: Bacillus thuringiensis

<400> SEQUENCE: 17

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110
```

-continued

Met Leu Arg Val Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Lys
130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
            165                 170                 175

Lys Tyr Val Asn Glu Lys Phe Glu Glu Leu Thr Phe Ala Thr Glu Thr
                180                 185                 190

Ser Ser Lys Val Lys Lys Asp Gly Ser Pro Ala Asp Ile Leu Asp Glu
            195                 200                 205

Leu Thr Glu Leu Thr Glu Leu Ala Lys Ser Val Thr Lys Asn Asp Val
            210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Gln Ala Phe Leu Thr
            275                 280                 285

Leu Thr Thr Cys Arg Lys Leu Leu Gly Leu Ala Asp Ile Asp Tyr Thr
            290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
            355                 360                 365

Val Leu Lys Val Tyr Glu Ala Lys Leu Lys Gln Asn Tyr Gln Val Asp
            370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
            435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
            485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Gly Ser Ile

```
              530                 535                 540
Glu Glu Asp Asn Leu Glu Pro Trp Lys Ala Asn Asn Lys Asn Ala Tyr
545                 550                 555                 560

Val Asp His Thr Gly Val Asn Gly Thr Lys Ala Leu Tyr Val His
                565                 570                 575

Lys Asp Gly Gly Ile Ser Gln Phe Ile Gly Asp Lys Leu Lys Pro Lys
                580                 585                 590

Thr Glu Tyr Val Ile Gln Tyr Thr Val Lys Gly Lys Pro Ser Ile His
                595                 600                 605

Leu Lys Asp Glu Asn Thr Gly Tyr Ile His Tyr Glu Asp Thr Asn Asn
                610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
                660                 665                 670

Leu Leu Ser Pro Glu Leu Ile Asn Thr Asn Asn Trp Thr Ser Thr Gly
                675                 680                 685

Ser Thr Asn Ile Ser Gly Asn Thr Leu Thr Leu Tyr Gln Gly Gly Arg
                690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
                740                 745                 750

Ser Glu Met Phe Thr Thr Lys Phe Glu Lys Asp Asn Phe Tyr Ile Glu
                755                 760                 765

Leu Ser Gln Gly Asn Asn Leu Tyr Gly Gly Pro Ile Val His Phe Tyr
                770                 775                 780

Asp Val Ser Ile Lys
785

<210> SEQ ID NO 18
<211> LENGTH: 110
<212> TYPE: PRT
<213> ORGANISM: Paenibacillus sp. NRRL B-50972

<400> SEQUENCE: 18

Met Gly Asn Leu Leu Arg Lys Arg Tyr Arg Leu Thr Gln Val Ala
1               5                   10                  15

Arg Lys Lys Lys Glu Arg Asp Gln Lys Met Gly Ala Phe Arg Phe
                20                  25                  30

Met Pro Ile Tyr Arg Thr Gly Thr Ser Cys Ile Arg Asn Lys Lys Gly
                35                  40                  45

Asn Lys Arg Ile Tyr Arg Gln Gly Arg Arg Glu Arg Ile Cys Ala
50                  55                  60

Tyr Arg His His Leu His Ala Glu Arg Val Pro Ser Gly Leu Ser Asn
65                  70                  75                  80

Lys Lys Ile Cys Phe Met Lys Phe Lys Gly Gln Arg Arg Leu Arg Gly
                85                  90                  95

Gly Glu Gln Glu Pro Gln Gly Asn Ser Gly Gly Ala Val Gln
                100                 105                 110
```

<210> SEQ ID NO 19
<211> LENGTH: 3582
<212> TYPE: DNA
<213> ORGANISM: Paenibacillus sp. NRRL B-50972

<400> SEQUENCE: 19

| | | | | | |
|---|---|---|---|---|---|
| atggtagtat | tatctactgg | acctattgca | aacgatcctg | ttctaggagt | cagacccacc | 60 |
| caactggtca | cagtaaaaat | agataaccga | gattctgtaa | attcttctat | cgttttgatc | 120 |
| gagggtttta | ttttaaacgg | tagcagaaca | ttatatgtac | aacaattagt | ggtagtggga | 180 |
| ccaaatgcgg | ttataacgag | gaatttcttt | gcaaatgtag | acgcatttga | attcgttttt | 240 |
| accactagcg | gaccagcaga | gaatgaaact | caaatttctg | tttggggtaa | agatgcattg | 300 |
| gggcaattag | tacctgccca | tcggttagta | tctgacgaac | ttttaggaac | cgatcgagga | 360 |
| atccaaggac | ctcaaggagt | tcaggagcc | caaggcgacc | aaggtgacca | aggacctcag | 420 |
| ggtgttcaag | gacctcaagg | agttcaggga | gcccaaggag | accaaggagt | tcaaggcgta | 480 |
| caaggagacc | aaggacctca | aggagtccaa | ggcgaccaag | gtgaccaagg | acctcaagga | 540 |
| gttcaaggag | cgcaaggtga | ccaaggccct | caaggagttc | agggagccca | aggtgaccaa | 600 |
| ggacctcaag | gcgttcaggg | agcgcaaggt | gaccaaggac | ctcaaggtga | tcaaggacct | 660 |
| cagggagttc | aaggagacca | aggcgatcaa | ggaccacagg | gagttcaagg | cgtacaaggt | 720 |
| gatcaaggac | ctcagggtgt | tcaaggagac | caaggcgacc | aaggacctca | gggtgttcaa | 780 |
| ggcgtacaag | gtgaccaagg | acctcagggt | gttcaaggcg | tacaaggtga | ccaaggacct | 840 |
| cagggagttc | aaggagacca | aggcgatcaa | ggaccacagg | gagttcaagg | cgtacaaggt | 900 |
| gatcaaggac | ctcagggtgt | tcaaggagac | caaggcgacc | aaggacctca | gggtgttcaa | 960 |
| ggcgtacaag | gtgaccaagg | acctcagggt | gttcaaggcg | tacaaggtga | ccaaggacct | 1020 |
| cagggtgttc | aaggcgtaca | aggtgaccaa | ggacctcaag | gagttcaggg | agcccaaggt | 1080 |
| gaccaaggac | cacagggagt | tcaaggcgac | caaggacctc | aaggacctca | aggagttcaa | 1140 |
| ggtgaccaag | gacctcaggg | cgttcaagga | tcccaaggtg | atcaaggacc | tcaaggagtt | 1200 |
| caaggcgtac | aaggacctca | aggagttcaa | ggcgtacaag | gcgaccaagg | acctcaaggt | 1260 |
| gttcagggag | cccaaggcga | ccaaggccct | caaggagttc | aaggagtcca | aggtgaccaa | 1320 |
| ggaccacagg | gagttcaagg | accgcaaggt | gaccaaggac | cacagggagt | tcagggagtc | 1380 |
| caaggcgacc | aaggacctca | aggagtccaa | ggcgaccaag | gtgaccaagg | acctcaagga | 1440 |
| gttcaaggag | cgcaaggtga | ccaaggccct | caaggagttc | agggagccca | aggtgaccaa | 1500 |
| ggacctcaag | gcgttcaggg | agcgcaaggt | gaccaaggac | ctcaaggtga | tcaaggacct | 1560 |
| cagggagttc | aaggagacca | aggcgatcaa | ggaccacagg | gagttcaagg | cgtacaaggt | 1620 |
| gatcaaggac | ctcagggtgt | tcaaggagac | caaggcgacc | aaggacctca | gggtgttcaa | 1680 |
| ggcgtacaag | gtgaccaagg | acctcagggt | gttcaaggcg | tacaaggtga | ccaaggacct | 1740 |
| cagggtgttc | aaggcgtaca | aggtgaccaa | ggacctcaag | gagttcaggg | agcccaaggt | 1800 |
| gaccaaggac | cacagggagt | tcaaggcgac | caaggacctc | aaggacctca | aggagttcaa | 1860 |
| ggtgaccaag | gacctcaggg | cgttcaagga | tcccaaggtg | atcaaggacc | tcaaggagtt | 1920 |
| caaggcgtac | aaggacctca | aggagttcaa | ggcgtacaag | gcgaccaagg | acctcaaggt | 1980 |
| gttcagggag | cccaaggcga | ccaaggccct | caaggagttc | aaggagtcca | aggtgaccaa | 2040 |
| ggaccacagg | gagttcaagg | accgcaaggt | gaccaaggac | cacagggagt | tcagggagtc | 2100 |
| caaggcgacc | aaggacctca | aggtgaccaa | ggacctcaag | gtgaccaagg | acctcaaggt | 2160 |

```
gttcaaggtg accaaggacc tcaaggagtt cagggagccc aaggcgacca aggacctcaa    2220
ggagttcaag gaccgcaagg tgaccaagga cctcaaggag ttcaaggcgt acaaggtgat    2280
caaggacctc aaggagttca aggcgtacaa ggtgaccaag gaccacaggg tgttcaaggc    2340
gtacaaggtg accaaggacc tcaaggtgtt caaggagtcc aaggtgatca aggacctcaa    2400
ggagttcagg gagcccaagg cgaccaagga cctcagggag ttcagggagc caaggcgac     2460
caaggacctc agggagttca gggagcccaa ggtgaccaag gacctcaggg cgttcaagga    2520
gtacaaggtg accaaggatc tcaaggagtt caaggaccgc aaggtgacca aggacctcaa    2580
ggagttcaag gcgtacaagg tgaccaagga cctcaaggag ttcaaggagt ccaaggtgac    2640
caaggacctc aaggtgttca gggagcccaa ggtggccaag gacctcaggg cgttcaaggc    2700
gaccaaggtg accaaggacc acagggtgtt caaggatctc aaggtgacca aggaccacaa    2760
ggcgttcaag gagcccaagg cgaccaagga ccacagggtg ttcaaggcgt acaaggtgac    2820
caaggccctc aaggagttca aggagttcaa ggtgaccaag gaccacaggg agttcaaggt    2880
gttcaaggac cgcaaggtga ccaaggacca cagggtgttc aaggagccca aggcgaccaa    2940
ggaccacagg tgttcaagg agtgcaaggt gaccaaggac cgcaaggcga ccaaggtgac    3000
caaggacctc aaggtgttca gggagtccaa ggcgaccaag gacctcaagg tgttcaggga    3060
gtccaaggcg accaaggacc tcaaggtgtt caaggtgacc aaggaccaca gggagttcag    3120
ggagcccaag gtgaccaagg acctcaggga gttcaaggtg accaaggtga ccaaggacct    3180
caaggagttc aaggtgtaca aggtgaccaa ggacctcaag gtgttcaggg agcccaaggt    3240
gaccaaggac ctcagggcgt acaaggcgac caaggtgacc aaggaccaca gggtgttcaa    3300
ggcgtacaag gtgatcaagg acctcaagga gttcaaggcg tacaaggtga ccaaggacca    3360
cagggtgttc aaggcgtaca agtgaccaa ggaccacagg tgttcaagg cgaccaaggt     3420
gaccaaggac ctcaaggcgt acaaggcgat caaggacctc agggtgttca aggacctcag    3480
ggtgttcaag gacctcaggg tgttcaagga cctcaaggcg accaaggagc tcaaggtgtt    3540
caaggaccac aaggtgacca aggaccgcaa ggcattctgt aa                       3582
```

<210> SEQ ID NO 20
<211> LENGTH: 1193
<212> TYPE: PRT
<213> ORGANISM: Paenibacillus sp. NRRL B-50972

<400> SEQUENCE: 20

```
Met Val Val Leu Ser Thr Gly Pro Ile Ala Asn Asp Pro Val Leu Gly
1               5                   10                  15

Val Arg Pro Thr Gln Leu Val Thr Val Lys Ile Asp Asn Arg Asp Ser
            20                  25                  30

Val Asn Ser Ser Ile Val Leu Ile Glu Gly Phe Ile Leu Asn Gly Ser
        35                  40                  45

Arg Thr Leu Tyr Val Gln Gln Leu Val Val Gly Pro Asn Ala Val
    50                  55                  60

Ile Thr Arg Asn Phe Phe Ala Asn Val Asp Ala Phe Glu Phe Val Phe
65                  70                  75                  80

Thr Thr Ser Gly Pro Ala Glu Asn Glu Thr Gln Ile Ser Val Trp Gly
                85                  90                  95

Lys Asp Ala Leu Gly Gln Leu Val Pro Ala His Arg Leu Val Ser Asp
            100                 105                 110

Glu Leu Leu Gly Thr Asp Arg Gly Ile Gln Gly Pro Gln Gly Val Gln
```

```
            115                 120                 125
Gly Ala Gln Gly Asp Gln Gly Asp Gln Gly Pro Gln Gly Val Gln Gly
    130                 135                 140

Pro Gln Gly Val Gln Gly Ala Gln Gly Asp Gln Gly Val Gln Gly Val
145                 150                 155                 160

Gln Gly Asp Gln Gly Pro Gln Gly Val Gln Gly Asp Gln Gly Asp Gln
            165                 170                 175

Gly Pro Gln Gly Val Gln Gly Ala Gln Gly Asp Gln Gly Pro Gln Gly
        180                 185                 190

Val Gln Gly Ala Gln Gly Asp Gln Gly Pro Gln Gly Val Gln Gly Ala
            195                 200                 205

Gln Gly Asp Gln Gly Pro Gln Gly Asp Gln Gly Pro Gln Gly Val Gln
        210                 215                 220

Gly Asp Gln Gly Asp Gln Gly Pro Gln Gly Val Gln Gly Val Gln Gly
225                 230                 235                 240

Asp Gln Gly Pro Gln Gly Val Gln Gly Asp Gln Gly Asp Gln Gly Pro
            245                 250                 255

Gln Gly Val Gln Gly Val Gln Gly Asp Gln Gly Pro Gln Gly Val Gln
        260                 265                 270

Gly Val Gln Gly Asp Gln Gly Pro Gln Gly Val Gln Gly Asp Gln Gly
            275                 280                 285

Asp Gln Gly Pro Gln Gly Val Gln Gly Val Gln Gly Asp Gln Gly Pro
290                 295                 300

Gln Gly Val Gln Gly Asp Gln Gly Asp Gln Gly Pro Gln Gly Val Gln
305                 310                 315                 320

Gly Val Gln Gly Asp Gln Gly Pro Gln Gly Val Gln Gly Val Gln Gly
            325                 330                 335

Asp Gln Gly Pro Gln Gly Val Gln Gly Val Gln Gly Asp Gln Gly Pro
        340                 345                 350

Gln Gly Val Gln Gly Ala Gln Gly Asp Gln Gly Pro Gln Gly Val Gln
            355                 360                 365

Gly Asp Gln Gly Pro Gln Gly Pro Gln Gly Val Gln Gly Asp Gln Gly
        370                 375                 380

Pro Gln Gly Val Gln Gly Ser Gln Gly Asp Gln Gly Pro Gln Gly Val
385                 390                 395                 400

Gln Gly Val Gln Gly Pro Gln Gly Val Gln Gly Val Gln Gly Asp Gln
            405                 410                 415

Gly Pro Gln Gly Val Gln Gly Ala Gln Gly Asp Gln Gly Pro Gln Gly
        420                 425                 430

Val Gln Gly Val Gln Gly Asp Gln Gly Pro Gln Gly Val Gln Gly Pro
            435                 440                 445

Gln Gly Asp Gln Gly Pro Gln Gly Val Gln Gly Val Gln Gly Asp Gln
        450                 455                 460

Gly Pro Gln Gly Val Gln Gly Asp Gln Gly Asp Gln Gly Pro Gln Gly
465                 470                 475                 480

Val Gln Gly Ala Gln Gly Asp Gln Gly Pro Gln Gly Val Gln Gly Ala
            485                 490                 495

Gln Gly Asp Gln Gly Pro Gln Gly Val Gln Gly Ala Gln Gly Asp Gln
        500                 505                 510

Gly Pro Gln Gly Asp Gln Gly Pro Gln Gly Val Gln Gly Asp Gln Gly
        515                 520                 525

Asp Gln Gly Pro Gln Gly Val Gln Gly Val Gln Gly Asp Gln Gly Pro
    530                 535                 540
```

-continued

```
Gln Gly Val Gln Gly Asp Gln Gly Asp Gln Gly Pro Gln Gly Val Gln
545                 550                 555                 560
Gly Val Gln Gly Asp Gln Gly Pro Gln Gly Val Gln Gly Val Gln Gly
                565                 570                 575
Asp Gln Gly Pro Gln Gly Val Gln Gly Val Gly Asp Gln Gly Pro
            580                 585                 590
Gln Gly Val Gln Gly Ala Gln Gly Asp Gln Gly Pro Gln Gly Val Gln
            595                 600                 605
Gly Asp Gln Gly Pro Gln Gly Pro Gln Gly Val Gln Gly Asp Gln Gly
        610                 615                 620
Pro Gln Gly Val Gln Gly Ser Gln Gly Asp Gln Gly Pro Gln Gly Val
625                 630                 635                 640
Gln Gly Val Gln Gly Pro Gln Gly Val Gln Gly Val Gln Gly Asp Gln
            645                 650                 655
Gly Pro Gln Gly Val Gln Gly Ala Gln Gly Asp Gln Gly Pro Gln Gly
                660                 665                 670
Val Gln Gly Val Gln Gly Asp Gln Gly Pro Gln Gly Val Gln Gly Pro
            675                 680                 685
Gln Gly Asp Gln Gly Pro Gln Gly Val Gln Gly Val Gln Gly Asp Gln
        690                 695                 700
Gly Pro Gln Gly Asp Gln Gly Pro Gln Gly Asp Gln Gly Pro Gln Gly
705                 710                 715                 720
Val Gln Gly Asp Gln Gly Pro Gln Gly Val Gln Gly Ala Gly Asp
            725                 730                 735
Gln Gly Pro Gln Gly Val Gln Gly Pro Gln Gly Asp Gln Gly Pro Gln
                740                 745                 750
Gly Val Gln Gly Val Gly Asp Gln Gly Pro Gln Gly Val Gln Gly
            755                 760                 765
Val Gln Gly Asp Gln Gly Pro Gln Gly Val Gln Gly Val Gln Gly Asp
        770                 775                 780
Gln Gly Pro Gln Gly Val Gln Gly Val Gln Gly Asp Gln Gly Pro Gln
785                 790                 795                 800
Gly Val Gln Gly Ala Gln Gly Asp Gln Gly Pro Gln Gly Val Gln Gly
                805                 810                 815
Ala Gln Gly Asp Gln Gly Pro Gln Gly Val Gln Gly Ala Gly Asp
            820                 825                 830
Gln Gly Pro Gln Gly Val Gln Gly Val Gln Gly Asp Gln Gly Ser Gln
        835                 840                 845
Gly Val Gln Gly Pro Gln Gly Asp Gln Gly Pro Gln Gly Val Gln Gly
        850                 855                 860
Val Gln Gly Asp Gln Gly Pro Gln Gly Val Gln Gly Val Gln Gly Asp
865                 870                 875                 880
Gln Gly Pro Gln Gly Val Gln Gly Ala Gln Gly Gly Gln Gly Pro Gln
                885                 890                 895
Gly Val Gln Gly Asp Gln Gly Asp Gln Gly Pro Gln Gly Val Gln Gly
            900                 905                 910
Ser Gln Gly Asp Gln Gly Pro Gln Gly Val Gln Gly Ala Gly Asp
            915                 920                 925
Gln Gly Pro Gln Gly Val Gln Gly Val Gln Gly Asp Gln Gly Pro Gln
        930                 935                 940
Gly Val Gln Gly Val Gln Gly Asp Gln Gly Pro Gln Gly Val Gln Gly
945                 950                 955                 960
```

-continued

Val Gln Gly Pro Gln Gly Asp Gln Gly Pro Gln Gly Val Gln Gly Ala
                965                 970                 975

Gln Gly Asp Gln Gly Pro Gln Gly Val Gln Gly Val Gln Gly Asp Gln
            980                 985                 990

Gly Pro Gln Gly Asp Gln Gly Asp Gln Gly Pro Gln Gly Val Gln Gly
        995                 1000                1005

Val Gln Gly Asp Gln Gly Pro Gln Gly Val Gln Gly Val Gln Gly
    1010                1015                1020

Asp Gln Gly Pro Gln Gly Val Gln Gly Asp Gln Gly Pro Gln Gly
    1025                1030                1035

Val Gln Gly Ala Gln Gly Asp Gln Gly Pro Gln Gly Val Gln Gly
    1040                1045                1050

Asp Gln Gly Asp Gln Gly Pro Gln Gly Val Gln Gly Val Gln Gly
    1055                1060                1065

Asp Gln Gly Pro Gln Gly Val Gln Gly Ala Gln Gly Asp Gln Gly
    1070                1075                1080

Pro Gln Gly Val Gln Gly Asp Gln Gly Asp Gln Gly Pro Gln Gly
    1085                1090                1095

Val Gln Gly Val Gln Gly Asp Gln Gly Pro Gln Gly Val Gln Gly
    1100                1105                1110

Val Gln Gly Asp Gln Gly Pro Gln Gly Val Gln Gly Val Gln Gly
    1115                1120                1125

Asp Gln Gly Pro Gln Gly Val Gln Gly Asp Gln Gly Asp Gln Gly
    1130                1135                1140

Pro Gln Gly Val Gln Gly Asp Gln Gly Pro Gln Gly Val Gln Gly
    1145                1150                1155

Pro Gln Gly Val Gln Gly Pro Gln Gly Val Gln Gly Pro Gln Gly
    1160                1165                1170

Asp Gln Gly Ala Gln Gly Val Gln Gly Pro Gln Gly Asp Gln Gly
    1175                1180                1185

Pro Gln Gly Ile Leu
    1190

<210> SEQ ID NO 21
<211> LENGTH: 572
<212> TYPE: PRT
<213> ORGANISM: Paenibacillus sp. NRRL B-50972

<400> SEQUENCE: 21

Met Val Val Leu Ser Thr Gly Pro Ile Ala Asn Asp Pro Val Leu Gly
1               5                   10                  15

Val Arg Pro Thr Gln Leu Val Thr Val Lys Ile Asp Asn Arg Asp Ser
            20                  25                  30

Val Asn Ser Ser Ile Val Leu Ile Glu Gly Phe Ile Leu Asn Gly Ser
        35                  40                  45

Arg Thr Leu Tyr Val Gln Gln Leu Val Val Gly Pro Asn Ala Val
    50                  55                  60

Ile Thr Arg Asn Phe Phe Ala Asn Val Asp Ala Phe Glu Phe Val Phe
65                  70                  75                  80

Thr Thr Ser Gly Pro Ala Glu Asn Glu Thr Gln Ile Ser Val Trp Gly
                85                  90                  95

Lys Asp Ala Leu Gly Gln Leu Val Pro Ala His Arg Leu Val Ser Asp
            100                 105                 110

Glu Leu Leu Gly Thr Asp Arg Gly Ile Gln Gly Pro Gln Gly Val Gln
        115                 120                 125

```
Gly Ala Gln Gly Asp Gln Gly Asp Gln Gly Pro Gln Gly Val Gln Gly
        130                 135                 140

Pro Gln Gly Val Gln Gly Ala Gln Gly Asp Gln Gly Val Gln Gly Val
145                 150                 155                 160

Gln Gly Asp Gln Gly Pro Gln Gly Val Gln Gly Asp Gln Gly Asp Gln
            165                 170                 175

Gly Pro Gln Gly Val Gln Gly Ala Gln Gly Asp Gln Gly Pro Gln Gly
                180                 185                 190

Val Gln Gly Ala Gln Gly Asp Gln Gly Pro Gln Gly Val Gln Gly Ala
        195                 200                 205

Gln Gly Asp Gln Gly Pro Gln Gly Asp Gln Gly Pro Gln Gly Val Gln
210                 215                 220

Gly Asp Gln Gly Asp Gln Gly Pro Gln Gly Val Gln Gly Val Gln Gly
225                 230                 235                 240

Asp Gln Gly Pro Gln Gly Val Gln Gly Asp Gln Gly Asp Gln Gly Pro
            245                 250                 255

Gln Gly Val Gln Gly Val Gln Gly Asp Gln Gly Pro Gln Gly Val Gln
        260                 265                 270

Gly Val Gln Gly Asp Gln Gly Pro Gln Gly Val Gln Gly Val Gln Gly
            275                 280                 285

Asp Gln Gly Pro Gln Gly Val Gln Gly Ala Gln Gly Asp Gln Gly Pro
290                 295                 300

Gln Gly Val Gln Gly Asp Gln Gly Pro Gln Gly Leu Gln Gly Val Gln
305                 310                 315                 320

Gly Asp Gln Gly Pro Gln Gly Val Gln Gly Ser Gln Gly Asp Gln Gly
            325                 330                 335

Pro Gln Gly Val Gln Gly Val Gln Gly Pro Gln Gly Gly Gln Gly Val
                340                 345                 350

Gln Gly Asp Gln Gly Pro Gln Gly Val Gln Gly Ala Gln Gly Asp Gln
        355                 360                 365

Gly Pro Gln Gly Val Gln Gly Asp Gln Gly Asp Gln Gly Pro Gln Gly
            370                 375                 380

Val Gln Gly Ala Gln Gly Asp Gln Gly Pro Gln Gly Val Gln Gly Asp
385                 390                 395                 400

Gln Gly Asp Gln Gly Pro Gln Gly Val Gln Gly Asp Gln Gly Thr Lys
            405                 410                 415

Glu Leu Lys Glu Tyr Lys Val Thr Lys Glu Leu Lys Glu Phe Lys Glu
                420                 425                 430

Pro Lys Val Thr Lys Asp Leu Arg Ala Phe Lys Ala Thr Lys Val Thr
        435                 440                 445

Lys Asp His Arg Val Phe Lys Glu Phe Lys Val Thr Lys Asp Leu Lys
450                 455                 460

Glu Phe Lys Glu Tyr Lys Val Thr Lys Asp His Arg Val Phe Lys Ala
465                 470                 475                 480

Tyr Lys Val Thr Lys Asp Leu Lys Val Phe Lys Ala Thr Lys Val Thr
            485                 490                 495

Lys Asp Leu Lys Ala Tyr Lys Ala Ile Lys Asp Leu Arg Val Phe Lys
                500                 505                 510

Asp Leu Arg Val Phe Lys Asp Leu Arg Val Phe Lys Asp Leu Lys Ala
        515                 520                 525

Thr Lys Glu Leu Lys Val Phe Lys Asp His Lys Val Thr Lys Asp Arg
530                 535                 540
```

```
Lys Ala Phe Cys Lys Leu Lys Val Lys Val Tyr Leu Asp Asp Ser Lys
545                 550                 555                 560

Val Ile Ile Thr Phe Gly Ser Phe Phe Val Leu Ser
                565                 570

<210> SEQ ID NO 22
<211> LENGTH: 450
<212> TYPE: PRT
<213> ORGANISM: Paenibacillus sp. NRRL B-50972

<400> SEQUENCE: 22

Met Val Val Leu Ser Thr Gly Pro Ile Ala Asn Asp Pro Val Leu Gly
1               5                   10                  15

Val Arg Pro Thr Gln Leu Val Thr Val Lys Ile Asp Asn Arg Asp Ser
                20                  25                  30

Val Asn Ser Ser Ile Val Leu Ile Glu Gly Phe Ile Leu Asn Gly Ser
            35                  40                  45

Arg Thr Leu Tyr Val Gln Gln Leu Val Val Gly Pro Asn Ala Val
        50                  55                  60

Ile Thr Arg Asn Phe Phe Ala Asn Val Asp Ala Phe Glu Phe Val Phe
65              70                  75                  80

Thr Thr Ser Gly Pro Ala Glu Asn Glu Thr Gln Ile Ser Val Trp Gly
                85                  90                  95

Lys Asp Ala Leu Gly Gln Leu Val Pro Ala His Arg Leu Val Ser Asp
                100                 105                 110

Glu Leu Leu Gly Thr Asp Arg Gly Ile Gln Gly Pro Gln Gly Val Gln
            115                 120                 125

Gly Ala Gln Gly Asp Gln Gly Asp Gln Gly Pro Gln Gly Val Gln Gly
        130                 135                 140

Pro Gln Gly Val Gln Gly Ala Gln Gly Asp Gln Gly Val Gln Gly Val
145                 150                 155                 160

Gln Gly Asp Gln Gly Pro Gln Gly Val Gln Gly Asp Gln Gly Asp Gln
                165                 170                 175

Gly Pro Gln Gly Val Gln Gly Ala Gln Gly Asp Gln Gly Pro Gln Gly
            180                 185                 190

Val Gln Gly Ala Gln Gly Asp Gln Gly Pro Gln Gly Val Gln Gly Ala
        195                 200                 205

Gln Gly Asp Gln Gly Pro Gln Gly Asp Gln Gly Pro Gln Gly Val Gln
    210                 215                 220

Gly Asp Gln Gly Asp Gln Gly Pro Gln Gly Val Gln Gly Val Gln Gly
225                 230                 235                 240

Asp Gln Gly Pro Gln Gly Val Gln Gly Asp Gln Gly Asp Gln Gly Pro
                245                 250                 255

Gln Gly Val Gln Gly Val Gln Gly Asp Gln Gly Pro Gln Gly Val Gln
            260                 265                 270

Gly Val Gln Gly Asp Gln Gly Pro Gln Gly Val Gln Gly Val Gln Gly
        275                 280                 285

Asp Gln Gly Pro Gln Gly Val Gln Gly Ala Gln Gly Asp Gln Gly Pro
    290                 295                 300

Gln Gly Val Gln Gly Asp Gln Gly Pro Gln Gly Pro Gln Gly Val Gln
305                 310                 315                 320

Gly Asp Gln Gly Pro Gln Gly Val Gln Gly Ala Gln Gly Asp Gln Gly
                325                 330                 335

Pro Gln Gly Val Gln Gly Val Gln Gly Pro Gln Gly Val Gln Gly Val
            340                 345                 350
```

```
Gln Gly Asp Gln Gly Pro Gln Gly Val Gln Gly Ala Gln Gly Asp Gln
        355                 360                 365
Gly Pro Gln Gly Val Gln Gly Val Gln Gly Asp Gln Gly Pro Gln Gly
    370                 375                 380
Val Gln Gly Ala Gln Gly Asp Gln Gly Pro Gln Gly Val Gln Gly Val
385                 390                 395                 400
Gln Gly Asp Gln Gly Pro Gln Gly Val Gln Gly Asp Gln Gly Asp Gln
        405                 410                 415
Gly Pro Gln Gly Val Gln Gly Ala Gln Gly Asp Gln Gly Pro Gln Gly
    420                 425                 430
Val Gln Gly Ala Gln Gly Asp Gln Gly Pro Gln Gly Val Gln Gly Ala
        435                 440                 445
Gln Gly
    450

<210> SEQ ID NO 23
<211> LENGTH: 1032
<212> TYPE: DNA
<213> ORGANISM: Paenibacillus sp. NRRL B-50972

<400> SEQUENCE: 23
atgcctgcct tggatgaatg gagtagtata caacaaatcg atatggaggt gtttgtattg      60
ggtcgtcccg aattgaaacg aaagaaaggc cgtaaaaaag acgtttttat ccgctcttgg     120
tttagtaaaa acgtccgaa gagaaatgc cattcgaaac gaaagtgctt tgcaaggaa       180
atcgtcgtca gaaagcaaat cgtccgtgta aatataccctc aaaatgtttt aggtataaca    240
ggcgcaactg gagctatagg tgtagcaggt aacgtaggtg cagcgggcac tgtgggtgct    300
gctggagccg tcggaactgc ggggaaatgtc ggggctgccg gtaatgtggg tactgcgggc    360
accgttggga ctgccggaaa tgtaggcgca gcggggggctg tgggcactgc gggcgctgtt    420
ggagctgcgg gtgcggtagg accagtaggt cccgtaggtc ctgcgggcat tccaggggca    480
gtcggtccag caggtcctgc gggcgttgca ggggcggtcg gtcctgtagg tcctgcgggt    540
gcggtaggtg ccactgggc tacgggtacc gcaggagcga cggggtccac cgggggctacg    600
ggagctacag gaaccgcagg tggaatagct cagtttggtt atatctacaa cttaggatcc    660
cgagtcgttc aatagaaagc ggatgtcatt ttcgatacga acggtatact tacacctgga    720
attacccacg ctcccggcac tacgcagatt gcagttaccg atgcgggaa ctatgaagtt    780
aactttttcag tatcgggtgt agagccaggc caatttgcca tatttatcaa tggcactctg    840
gcagcaggaa ccatatacgg ctcaggagct ggtacgcagc aaaacacagg gcaggccatc    900
ctcgctctag catccggtga tgttcttacc ctgcgaaatc atagctctgc cgctgcggtt    960
accctgcaaa ccttggctgg aggtacccaa gccaacgtaa acgcttctgt cgttatcaaa   1020
aaattaagtt ag                                                       1032

<210> SEQ ID NO 24
<211> LENGTH: 343
<212> TYPE: PRT
<213> ORGANISM: Paenibacillus sp. NRRL B-50972

<400> SEQUENCE: 24

Met Pro Ala Leu Asp Glu Trp Ser Ser Ile Gln Gln Ile Asp Met Glu
1               5                   10                  15
Val Phe Val Leu Gly Arg Pro Glu Leu Lys Arg Lys Lys Gly Arg Lys
            20                  25                  30
```

Lys Asp Val Phe Ile Arg Ser Trp Phe Ser Lys Lys Arg Pro Lys Arg
       35                  40                  45

Lys Cys His Ser Lys Arg Lys Cys Phe Cys Lys Glu Ile Val Val Arg
 50                  55                  60

Lys Gln Ile Val Arg Val Asn Ile Pro Gln Asn Val Leu Gly Ile Thr
65                  70                  75                  80

Gly Ala Thr Gly Ala Ile Gly Val Ala Gly Asn Val Gly Ala Ala Gly
                85                  90                  95

Thr Val Gly Ala Ala Gly Ala Val Gly Thr Ala Gly Asn Val Gly Ala
                100                 105                 110

Ala Gly Asn Val Gly Thr Ala Gly Thr Val Gly Thr Ala Gly Asn Val
            115                 120                 125

Gly Ala Ala Gly Ala Val Gly Thr Ala Gly Ala Val Gly Ala Ala Gly
        130                 135                 140

Ala Val Gly Pro Val Gly Pro Val Gly Pro Ala Gly Ile Pro Gly Ala
145                 150                 155                 160

Val Gly Pro Ala Gly Pro Ala Gly Val Ala Gly Ala Val Gly Pro Val
                165                 170                 175

Gly Pro Ala Gly Ala Val Gly Ala Thr Gly Ala Thr Gly Thr Ala Gly
        180                 185                 190

Ala Thr Gly Ser Thr Gly Ala Thr Gly Ala Thr Gly Thr Ala Gly Gly
            195                 200                 205

Ile Ala Gln Phe Gly Tyr Ile Tyr Asn Leu Gly Ser Arg Val Val Pro
        210                 215                 220

Ile Glu Ala Asp Val Ile Phe Asp Thr Asn Gly Ile Leu Thr Pro Gly
225                 230                 235                 240

Ile Thr His Ala Pro Gly Thr Thr Gln Ile Ala Val Thr Asp Ala Gly
                245                 250                 255

Asn Tyr Glu Val Asn Phe Ser Val Ser Gly Val Glu Pro Gly Gln Phe
            260                 265                 270

Ala Ile Phe Ile Asn Gly Thr Leu Ala Ala Gly Thr Ile Tyr Gly Ser
        275                 280                 285

Gly Ala Gly Thr Gln Gln Asn Thr Gly Gln Ala Ile Leu Ala Leu Ala
        290                 295                 300

Ser Gly Asp Val Leu Thr Leu Arg Asn His Ser Ser Ala Ala Ala Val
305                 310                 315                 320

Thr Leu Gln Thr Leu Ala Gly Gly Thr Gln Ala Asn Val Asn Ala Ser
                325                 330                 335

Val Val Ile Lys Lys Leu Ser
            340

<210> SEQ ID NO 25
<211> LENGTH: 1497
<212> TYPE: DNA
<213> ORGANISM: Paenibacillus sp. NRRL B-50972

<400> SEQUENCE: 25
atgaaacaca gaaaaccgtt caggttcagt ggtgcttcaa aaaagacga ggactgcaaa      60 ccacctaaaa ttagcagaga acggaagaa cttctcaaac tgattaagga attagtcgcc    120
atcatcccgc tcgttttcgc aaacccgtct gtggctaatg taacttcatt gcaacagatt    180
ttacagcgat tattagctct cgcaaataaa ttgagactta gaggctcggc taagacagat    240
ttattagcgg cgttggaact ggctatcgtg gcgtcggaag ccactctttt ctccccgatc    300

```
ggtgttggaa cgacactgca acaactgctg gaagtcttat tgtctattat tttgcaggaa    360
ccccttgatc ctgctcttaa agacagtttg atcagtgcaa tcagaaatgc cgaaacggct    420
atcagtattg cgttgggtgg cacggcagga accccggtc acaagggcc cgctgggcct     480 gctggtccgg cggtgctcc aggacctgtc ggtggaccag ggccggtggg tgcggcagga    540
ccagcaggtc cagttggacc tgctggtcct gtcggacctg tcggggctgc cggacctgtt    600
ggagccgccg gacctgttgg agccgccgga cctatcggcg ccgctgggcc agtaggcgcc    660 gccgggctg ctggagccac cggggctaca ggagctacag gcgcggcagg acctgccggg     720
ggggctaccg gggccacggg cgccgttgga gccacaggcg ctacgggcgc agcgggggtc    780 gctgggggcta caggaactac gggcacggcg ggcgctgtcg gagctaccgg gccacgggc   840 acggcggggg ccattggagc taccggggcc acaggcacgg cggggggccgt cggagctacc   900 ggggccacag gcacggcggg cgctgtcgga gctaccgggg ccacgggtac agcagggggtt  960 actggagcca ccggttcggg ggcaatcatt ccatttgctt cgggtggacc agcaattttg   1020
acaaccattg tcgcgggct ggttggaacc acaagtttga tcggctttgg aagctcagca    1080
acaggcatta gccttgtggg tggaaccatt gacctgacag gcacacttgc agggccactg   1140
attaactttg cttttctgt accacgggat ggcgtaatta catccatcgc tggatatttt    1200
agtacaacag ctgcgctaac tctcgttgga tcaaccgcga cgattactgc ccagttgttt   1260
agttcgacta cacctgataa caccttaca gcggtccctg gggctaccgt tacattagct    1320
ccaccactga ctggcatcat tgccttgggt accatttcca atggcatcac taccggattg   1380
gctataccga taaccgcgca gactcgtctg ctccttgtct ctctgcaac agctacggga    1440 ctctcccctcg taaacaccat cgtgggttat gcgagcgcag gcattaccat caccctga    1497
```

<210> SEQ ID NO 26
<211> LENGTH: 498
<212> TYPE: PRT
<213> ORGANISM: Paenibacillus sp. NRRL B-50972

<400> SEQUENCE: 26

Met Lys His Arg Lys Pro Phe Arg Phe Ser Gly Ala Ser Lys Lys Asp
1               5                   10                  15

Glu Asp Cys Lys Pro Pro Lys Ile Ser Arg Glu Thr Glu Glu Leu Leu
                20                  25                  30

Lys Leu Ile Lys Glu Leu Val Ala Ile Ile Pro Leu Val Phe Ala Asn
            35                  40                  45

Pro Ser Val Ala Asn Val Thr Ser Leu Gln Gln Ile Leu Gln Arg Leu
        50                  55                  60

Leu Ala Leu Ala Asn Lys Leu Arg Leu Arg Gly Ser Ala Lys Thr Asp
65                  70                  75                  80

Leu Leu Ala Ala Leu Glu Leu Ala Ile Val Ala Ser Glu Ala Thr Leu
                85                  90                  95

Phe Ser Pro Ile Gly Val Gly Thr Thr Leu Gln Gln Leu Leu Glu Val
                100                 105                 110

Leu Leu Ser Ile Ile Leu Gln Glu Pro Leu Asp Pro Ala Leu Lys Asp
            115                 120                 125

Ser Leu Ile Ser Ala Ile Arg Asn Ala Glu Thr Ala Ile Ser Ile Ala
        130                 135                 140

Leu Gly Gly Thr Ala Gly Thr Pro Gly Pro Gln Gly Pro Ala Gly Pro
145                 150                 155                 160

Ala Gly Pro Gly Gly Ala Pro Gly Pro Val Gly Gly Pro Gly Pro Val

```
                165                 170                 175
Gly Ala Ala Gly Pro Ala Gly Pro Val Gly Pro Ala Gly Pro Val Gly
            180                 185                 190
Pro Val Gly Ala Ala Gly Pro Val Gly Ala Ala Gly Pro Val Gly Ala
            195                 200                 205
Ala Gly Pro Ile Gly Ala Ala Gly Pro Val Gly Ala Ala Gly Ala Ala
        210                 215                 220
Gly Ala Thr Gly Ala Thr Gly Ala Thr Gly Ala Ala Gly Pro Ala Gly
225                 230                 235                 240
Gly Ala Thr Gly Ala Thr Gly Ala Val Gly Ala Thr Gly Ala Thr Gly
            245                 250                 255
Ala Ala Gly Val Ala Gly Ala Thr Gly Thr Thr Gly Thr Ala Gly Ala
        260                 265                 270
Val Gly Ala Thr Gly Ala Thr Gly Thr Ala Gly Ala Ile Gly Ala Thr
        275                 280                 285
Gly Ala Thr Gly Thr Ala Gly Ala Val Gly Ala Thr Gly Ala Thr Gly
        290                 295                 300
Thr Ala Gly Ala Val Gly Ala Thr Gly Ala Thr Gly Thr Ala Gly Val
305                 310                 315                 320
Thr Gly Ala Thr Gly Ser Gly Ala Ile Ile Pro Phe Ala Ser Gly Gly
            325                 330                 335
Pro Ala Ile Leu Thr Thr Ile Val Gly Gly Leu Val Gly Thr Thr Ser
        340                 345                 350
Leu Ile Gly Phe Gly Ser Ser Ala Thr Gly Ile Ser Leu Val Gly Gly
            355                 360                 365
Thr Ile Asp Leu Thr Gly Thr Leu Ala Gly Pro Leu Ile Asn Phe Ala
        370                 375                 380
Phe Ser Val Pro Arg Asp Gly Val Ile Thr Ser Ile Ala Gly Tyr Phe
385                 390                 395                 400
Ser Thr Thr Ala Ala Leu Thr Leu Val Gly Ser Thr Ala Thr Ile Thr
            405                 410                 415
Ala Gln Leu Phe Ser Ser Thr Pro Asp Asn Thr Phe Thr Ala Val
        420                 425                 430
Pro Gly Ala Thr Val Thr Leu Ala Pro Pro Leu Thr Gly Ile Ile Ala
        435                 440                 445
Leu Gly Thr Ile Ser Asn Gly Ile Thr Thr Gly Leu Ala Ile Pro Val
        450                 455                 460
Thr Ala Gln Thr Arg Leu Leu Leu Val Phe Ser Ala Thr Ala Thr Gly
465                 470                 475                 480
Leu Ser Leu Val Asn Thr Ile Val Gly Tyr Ala Ser Ala Gly Ile Thr
            485                 490                 495
Ile Thr

<210> SEQ ID NO 27
<211> LENGTH: 3744
<212> TYPE: DNA
<213> ORGANISM: Paenibacillus sp. NRRL B-50972

<400> SEQUENCE: 27
atggcggtta tatcaactgg acccatagaa ataattatg tcagtggtat tcggcctact      60
catcgagtta ccgtgaaaat tgataatcgt gatactgtga attcttctac ggtattgatt     120
cagggttttt atctaaatgg tacaagaacg ttatatgtgc ttgattttat aactgtaaat     180
tcaaatgaag tgattacaaa agattattat gctgatttta attcatttga gtttgttttt     240
```

```
accactgaaa gtgttacaga aaatgagatt caagtttcag tctggggtaa aaattcaatg    300
gggcagttag tgacagctca ccgtgttgta tcttccgaat tgcttgtagc aaaaggcgcg    360
ggaccgacag ggctaacggg agccactggc gctaccggag ctactggcgt cacgggtgtt    420
accggagtca ctggcgctac cggaactacg ggcgttatgg gtgataccgg agtcactgga    480
gttaccggag ttactggcgt taccggggct atcggagtca ctggcgctat cggagtcacg    540
ggggctaccg gagccacagg agttacgggg ccactggact taccggggc tattggagtt     600
actggcgcta tcggagtcac tggcgctacc ggagctactg gcgttactgg ggctactggc    660
gctactggag tcacaggagt taccggggct actggcgtta ccggagttac cggagttact    720
ggcatcaccg gggctatcgg agctactggc gttaccggag ctactggcgt cacgggtatt    780
accggagtca ctggcgttac cggggctact ggcgttactg gagttactgg catcacaggc    840
gttaccggag ttactggtgt tactggtgtt actggagcta ctggcgttac cggggctact    900
ggcgctaccg gagccactgg cgttactgga gttactggcg ttactggcgc tactggagct    960
actggtgtta ccggggctac cggggctacc ggtgtcacgg gtgataccgg tgtcactggc   1020
gctaccgggg ctaccggagt ttctggcgct actggggcta ctggtgtcac gggtgatacc   1080
ggagttaccg gagctactgg cgctacaggt gctaccggag ttactggcgg aacaggtgca   1140
accggagtta ctggagttac tggcgttacc ggggctatcg gagtcactgg cgctactgga   1200
gctactggag ctgctggaat cacgggtgtt accggagtta ctggcatcac cggtgctacc   1260
ggggctacgg gcgctaccgg agttactggc atcacaggag tcactggcgc taccggagtt   1320
actggcgtaa caggtgcaac cggagttact ggagttaccg gggctatcgg agttactggt   1380
gtcaccggag ctactggcgt cacgggtgtt accggagtca ctggcgctac cggagctact   1440
ggcgttacgg gtgttaccgg agttaccgga gttactggcg ttaccggagc tactggcgtt   1500
accggagtta ctggagttac tggagttatt ggagttactg gagttactgg agttactgga   1560
gttactggag ttaccggagt taccggagtt actggagtta ccggggctat cggagtcact   1620
ggcgctatcg gagtcacggg ggctaccggg gtcactggcg ctaccggagc tactggcgta   1680
acaggggcta ctggagttac cggggctatc ggagtcactg gcgctactgg agctgctgga   1740
atcacgggtg ttaccggagt cactggtgtt actggagtta ccggagctac tggcatcacg   1800
ggtgataccg gagtcactgg cgctaccgga gctactggcg ttacgggtgt taccggagtc   1860
actggggcta ccggagctac tggcgtcacg ggtgataccg gagttactgg agtcactggc   1920
gctaccggag ttactggcgt aacaggtgca gccggagtta ctggcatcac gggggctacc   1980
ggagttactg gagttaccgg ggctattgga gtcactggcg ctatcggagt cacggggggct  2040
accggagcca caggagttac gggtattacc ggagctactg gcgctactgg agccacaggt   2100
gctaccggag ttactggagt tactggcgct accggagcta ctggcgctac tggcgtcacg   2160
ggttctactg gggtcactgg cgctactggc gttaccggag ctactggcgt cacgggttct   2220
actggggtca ctggcgctac tggcgttacc ggagctactg gcgtcacggg tattaccgga   2280
gtcactggcg ttaccggagt tactggtgct actggagcta ctggcgttac cggggctacc   2340
ggagtcactg ggctaccgg agctactggc gtcacgggta ttaccggagt cactgggggct   2400
accggagcta ctggcgtcac gggtgttacc ggagtcaccg gagtcactgg agttactgga   2460
gttactggcg ctaccggagc tactggcgtt accggagcta ctggcgctac tggcgtcacg   2520
ggtgataccg gagtcactgg ggctaccgga gttaccggag tcactggcgc tactggggct   2580
```

-continued

| | |
|---|---|
| actggtgtca cgggtgttac cggagtcact ggcgctaccg gggctactgg tgtcacgggt | 2640 |
| gttaccgggg ctaccggagc tactggcgac acgggtgtta ccggagtcac tggagtcact | 2700 |
| ggagttaccg gagtttctgg cgctaccgga gttaccggag tttctggcgc taccggagtt | 2760 |
| accggagcta ctggcgttac cggggctggg gctaccggag ctactggcgc tactggagtc | 2820 |
| acaggtgtta ccggagtcac tggcgctacc ggagctactg gcgctactgg agtcacgggt | 2880 |
| gttaccggag tcactggcgc taccggggct actggtgtca cgggtgttac cggggctacc | 2940 |
| ggagctactg gcgacacggg tgttaccgga gtcactggag tcactggagt taccggagtt | 3000 |
| tctggcgcta ccggagttac cggagctact ggcgttaccg ggctggggc taccggagct | 3060 |
| actggcgcta ctggagtcac aggtgttacc ggagtcactg gcgctaccgg agctactggc | 3120 |
| gctactggag tcacgggtgt taccggagtc actggcgcta ccggggctac tggcgctact | 3180 |
| ggagtcacgg gtgttactgg cgttacgggt gttaccggag tttctggcat caccggtgct | 3240 |
| accggggcta ttggacctac tggtgccaca ggtgttggta taacaggttc aacaggttca | 3300 |
| accggcccca ctggcccacc tcctacgttt atagacgcat actttaacgg taatattcaa | 3360 |
| cctcagacaa ttgcttcggg atcaaacatt ttaaatatta ctccaaacca atctactgca | 3420 |
| cttacttata acgcagtaac aagtgttttc acaatacaaa atgcggggtt gtataacatt | 3480 |
| agtgttgtaa taaatcttgc aactgccaca ctaccagaag caacaattgg gttatcacta | 3540 |
| aataattcta cagcatatct cgctcctgct gtaaccacgg caacaagtgg tcaattggtt | 3600 |
| ttagttcaaa ttgaggctct tgctgtcgga gatacaattc aatttagaaa tatatctggg | 3660 |
| tttcctatta ccattgctaa ttcaccagta atagctaaca gctcaggtca tgtagctatt | 3720 |
| tcgagattct cagctttttc ataa | 3744 |

<210> SEQ ID NO 28
<211> LENGTH: 1247
<212> TYPE: PRT
<213> ORGANISM: Paenibacillus sp. NRRL B-50972

<400> SEQUENCE: 28

```
Met Ala Val Ile Ser Thr Gly Pro Ile Glu Asn Asn Tyr Val Ser Gly
1               5                   10                  15

Ile Arg Pro Thr His Arg Val Thr Val Lys Ile Asp Asn Arg Asp Thr
            20                  25                  30

Val Asn Ser Ser Thr Val Leu Ile Gln Gly Phe Tyr Leu Asn Gly Thr
        35                  40                  45

Arg Thr Leu Tyr Val Leu Asp Phe Ile Thr Val Asn Ser Asn Glu Val
    50                  55                  60

Ile Thr Lys Asp Tyr Tyr Ala Asp Phe Asn Ser Phe Glu Phe Val Phe
65                  70                  75                  80

Thr Thr Glu Ser Val Thr Glu Asn Glu Ile Gln Val Ser Val Trp Gly
                85                  90                  95

Lys Asn Ser Met Gly Gln Leu Val Thr Ala His Arg Val Val Ser Ser
            100                 105                 110

Glu Leu Leu Val Ala Lys Gly Ala Gly Pro Thr Gly Leu Thr Gly Ala
        115                 120                 125

Thr Gly Ala Thr Gly Ala Thr Gly Val Thr Gly Thr Gly Val Thr
    130                 135                 140

Gly Ala Thr Gly Thr Thr Gly Val Met Gly Asp Thr Gly Val Thr Gly
145                 150                 155                 160

Val Thr Gly Val Thr Gly Val Thr Gly Ala Ile Gly Val Thr Gly Ala
```

```
                    165                 170                 175
Ile Gly Val Thr Gly Ala Thr Gly Ala Thr Gly Val Thr Gly Ala Thr
                180                 185                 190
Gly Val Thr Gly Ala Ile Gly Val Thr Gly Ala Ile Gly Val Thr Gly
                195                 200                 205
Ala Thr Gly Ala Thr Gly Val Thr Gly Ala Thr Gly Ala Thr Gly Val
            210                 215                 220
Thr Gly Val Thr Gly Ala Thr Gly Val Thr Gly Val Thr Gly Val Thr
225                 230                 235                 240
Gly Ile Thr Gly Ala Ile Gly Ala Thr Gly Val Thr Gly Ala Thr Gly
                245                 250                 255
Val Thr Gly Ile Thr Gly Val Thr Gly Val Thr Gly Ala Thr Gly Val
                260                 265                 270
Thr Gly Val Thr Gly Ile Thr Gly Val Thr Gly Val Thr Gly Val Thr
                275                 280                 285
Gly Val Thr Gly Ala Thr Gly Val Thr Gly Ala Thr Gly Ala Thr Gly
                290                 295                 300
Ala Thr Gly Val Thr Gly Val Thr Gly Val Thr Gly Ala Thr Gly Ala
305                 310                 315                 320
Thr Gly Val Thr Gly Ala Thr Gly Ala Thr Gly Val Thr Gly Asp Thr
                325                 330                 335
Gly Val Thr Gly Ala Thr Gly Ala Thr Gly Val Ser Gly Ala Thr Gly
                340                 345                 350
Ala Thr Gly Val Thr Gly Asp Thr Gly Val Thr Gly Ala Thr Gly Ala
                355                 360                 365
Thr Gly Ala Thr Gly Val Thr Gly Gly Thr Gly Ala Thr Gly Val Thr
            370                 375                 380
Gly Val Thr Gly Val Thr Gly Ala Ile Gly Val Thr Gly Ala Thr Gly
385                 390                 395                 400
Ala Thr Gly Ala Ala Gly Ile Thr Gly Val Thr Gly Val Thr Gly Ile
                405                 410                 415
Thr Gly Ala Thr Gly Ala Thr Gly Ala Thr Gly Val Thr Gly Ile Thr
                420                 425                 430
Gly Val Thr Gly Ala Thr Gly Val Thr Gly Val Thr Gly Ala Thr Gly
            435                 440                 445
Val Thr Gly Val Thr Gly Ala Ile Gly Val Thr Gly Val Thr Gly Ala
            450                 455                 460
Thr Gly Val Thr Gly Val Thr Gly Val Thr Gly Ala Thr Gly Ala Thr
465                 470                 475                 480
Gly Val Thr Gly Val Thr Gly Val Thr Gly Val Thr Gly Val Thr Gly
                485                 490                 495
Ala Thr Gly Val Thr Gly Val Thr Gly Val Thr Gly Val Ile Gly Val
                500                 505                 510
Thr Gly Val Thr Gly Val Thr Gly Val Thr Gly Val Thr Gly Val Thr
                515                 520                 525
Gly Val Thr Gly Val Thr Gly Ala Ile Gly Val Thr Gly Ala Ile Gly
                530                 535                 540
Val Thr Gly Ala Thr Gly Val Thr Gly Ala Thr Gly Ala Thr Gly Val
545                 550                 555                 560
Thr Gly Ala Thr Gly Val Thr Gly Ala Ile Gly Val Thr Gly Ala Thr
                565                 570                 575
Gly Ala Ala Gly Ile Thr Gly Val Thr Gly Val Thr Gly Val Thr Gly
                580                 585                 590
```

```
Val Thr Gly Ala Thr Gly Ile Thr Gly Asp Thr Gly Val Thr Gly Ala
            595                 600                 605

Thr Gly Ala Thr Gly Val Thr Gly Val Thr Gly Val Thr Gly Ala Thr
            610                 615                 620

Gly Ala Thr Gly Val Thr Gly Asp Thr Gly Val Thr Gly Val Thr Gly
625                 630                 635                 640

Ala Thr Gly Val Thr Gly Val Thr Gly Ala Gly Val Thr Gly Ile
            645                 650                 655

Thr Gly Ala Thr Gly Val Thr Gly Val Thr Gly Ala Ile Gly Val Thr
            660                 665                 670

Gly Ala Ile Gly Val Thr Gly Ala Thr Gly Ala Thr Gly Val Thr Gly
            675                 680                 685

Ile Thr Gly Ala Thr Gly Ala Thr Gly Ala Thr Gly Ala Thr Gly Val
            690                 695                 700

Thr Gly Val Thr Gly Ala Thr Gly Ala Thr Gly Ala Thr Gly Val Thr
705                 710                 715                 720

Gly Ser Thr Gly Val Thr Gly Ala Thr Gly Val Thr Gly Ala Thr Gly
                    725                 730                 735

Val Thr Gly Ser Thr Gly Val Thr Gly Ala Thr Gly Val Thr Gly Ala
                740                 745                 750

Thr Gly Val Thr Gly Ile Thr Gly Val Thr Gly Val Thr Gly Val Thr
            755                 760                 765

Gly Ala Thr Gly Ala Thr Gly Val Thr Gly Ala Thr Gly Val Thr Gly
            770                 775                 780

Ala Thr Gly Ala Thr Gly Val Thr Gly Ile Thr Gly Val Thr Gly Ala
785                 790                 795                 800

Thr Gly Ala Thr Gly Val Thr Gly Val Thr Gly Val Thr Gly Val Thr
            805                 810                 815

Gly Val Thr Gly Val Thr Gly Ala Thr Gly Ala Thr Gly Val Thr Gly
            820                 825                 830

Ala Thr Gly Ala Thr Gly Val Thr Gly Asp Thr Gly Val Thr Gly Ala
            835                 840                 845

Thr Gly Val Thr Gly Val Thr Gly Ala Thr Gly Ala Thr Gly Val Thr
            850                 855                 860

Gly Val Thr Gly Val Thr Gly Ala Thr Gly Ala Thr Gly Val Thr Gly
865                 870                 875                 880

Val Thr Gly Ala Thr Gly Ala Thr Gly Asp Thr Gly Val Thr Gly Val
                885                 890                 895

Thr Gly Val Thr Gly Val Thr Gly Val Ser Gly Ala Thr Gly Val Thr
                900                 905                 910

Gly Val Ser Gly Ala Thr Gly Val Thr Gly Ala Thr Gly Val Thr Gly
            915                 920                 925

Ala Gly Ala Thr Gly Ala Thr Gly Ala Thr Gly Val Thr Gly Val Thr
            930                 935                 940

Gly Val Thr Gly Ala Thr Gly Ala Thr Gly Ala Thr Gly Val Thr Gly
945                 950                 955                 960

Val Thr Gly Val Thr Gly Ala Thr Gly Ala Thr Gly Val Thr Gly Val
                965                 970                 975

Thr Gly Ala Thr Gly Ala Thr Gly Asp Thr Gly Val Thr Gly Val Thr
            980                 985                 990

Gly Val Thr Gly Val Thr Gly Val Ser Gly Ala Thr Gly Val Thr Gly
            995                 1000                1005
```

```
Ala Thr Gly Val Thr Gly Ala Gly Ala Thr Gly Ala
    1010                1015                1020

Thr Gly Val Thr Gly Val Thr Gly Val Thr Gly Ala Thr Gly Ala
    1025                1030                1035

Thr Gly Ala Thr Gly Val Thr Gly Val Thr Gly Val Thr Gly Ala
    1040                1045                1050

Thr Gly Ala Thr Gly Ala Thr Gly Val Thr Gly Val Thr Gly Val
    1055                1060                1065

Thr Gly Val Thr Gly Val Ser Gly Ile Thr Gly Ala Thr Gly Ala
    1070                1075                1080

Ile Gly Pro Thr Gly Ala Thr Gly Val Gly Ile Thr Gly Ser Thr
    1085                1090                1095

Gly Ser Thr Gly Pro Thr Gly Pro Pro Thr Phe Ile Asp Ala
    1100                1105                1110

Tyr Phe Asn Gly Asn Ile Gln Pro Gln Thr Ile Ala Ser Gly Ser
    1115                1120                1125

Asn Ile Leu Asn Ile Thr Pro Asn Gln Ser Thr Ala Leu Thr Tyr
    1130                1135                1140

Asn Ala Val Thr Ser Val Phe Thr Ile Gln Asn Ala Gly Leu Tyr
    1145                1150                1155

Asn Ile Ser Val Val Ile Asn Leu Ala Thr Ala Thr Leu Pro Glu
    1160                1165                1170

Ala Thr Ile Gly Leu Ser Leu Asn Asn Ser Thr Ala Tyr Leu Ala
    1175                1180                1185

Pro Ala Val Thr Thr Ala Thr Ser Gly Gln Leu Val Leu Val Gln
    1190                1195                1200

Ile Glu Ala Leu Ala Val Gly Asp Thr Ile Gln Phe Arg Asn Ile
    1205                1210                1215

Ser Gly Phe Pro Ile Thr Ile Ala Asn Ser Pro Val Ile Ala Asn
    1220                1225                1230

Ser Ser Gly His Val Ala Ile Ser Arg Phe Ser Ala Phe Ser
    1235                1240                1245

<210> SEQ ID NO 29
<211> LENGTH: 849
<212> TYPE: DNA
<213> ORGANISM: Paenibacillus sp. NRRL B-50972

<400> SEQUENCE: 29
ttgggaaatt tattgttgcg taaaagatat cgcttgaccc aggtggcaag gaaaaaaaag    60
aaggaaagag atcaaaagat gggagcgttc cgttttatgc ccatttatcg tacaggaacg   120
agctgcattc gtaacaaaaa gggaaataaa cgtatttata gacagggtag aagaagagag   180
agaatatgcg cttatagaca tcatttgcac gctgagcggg tgccctcagg tttatcaaat   240
aaaaaaatct gttttatgaa attcaaaggt caacgaagac tgcgaggcgg cgaacaggag   300
cctcaaggca attcaggagg agcagttcaa ggggtgcatg gattaagggg gaccgatggt   360
aatgctgggc atcaaggcat acaaggtccg gctgggccac agggcattcc gggtagtgcc   420
ggaccccagg gccaggcggg cgccataggc ccccaaggtg aacagggtct tcagggggtt   480
ccagggattc aaggcttgca aggagaggct gggccacagg gagagcaggg accaccgctt   540
aatttggatg ggatcacggt tgtgcctgag gtacagcgat atttctattt tgccgattca   600
gatctgacgg gtacggttga atccctatt tcccagttta cgaatgatga tggacagttg   660
gcaagtcagc ttccagaatt gggtgcgaac agctacacgg atttgtatat taatggggta   720
```

```
ctgcaggaaa gcaggttgta ccagataagt agtaccacat tgactgttga attggaagaa    780
gctcttgtaa ttgcgggtac gccgtttatt ttcgaggttt ttcaatttac attaagaatg    840
gcgaactga                                                             849
```

<210> SEQ ID NO 30
<211> LENGTH: 282
<212> TYPE: PRT
<213> ORGANISM: Paenibacillus sp. NRRL B-50972

<400> SEQUENCE: 30

```
Met Gly Asn Leu Leu Arg Lys Arg Tyr Arg Leu Thr Gln Val Ala
1               5                   10                  15

Arg Lys Lys Lys Glu Arg Asp Gln Lys Met Gly Ala Phe Arg Phe
            20                  25                  30

Met Pro Ile Tyr Arg Thr Gly Thr Ser Cys Ile Arg Asn Lys Lys Gly
        35                  40                  45

Asn Lys Arg Ile Tyr Arg Gln Gly Arg Arg Glu Arg Ile Cys Ala
    50                  55                  60

Tyr Arg His His Leu His Ala Glu Arg Val Pro Ser Gly Leu Ser Asn
65                  70                  75                  80

Lys Lys Ile Cys Phe Met Lys Phe Lys Gly Gln Arg Arg Leu Arg Gly
                85                  90                  95

Gly Glu Gln Glu Pro Gln Gly Asn Ser Gly Gly Ala Val Gln Gly Val
            100                 105                 110

His Gly Leu Arg Gly Thr Asp Gly Asn Ala Gly His Gln Gly Ile Gln
        115                 120                 125

Gly Pro Ala Gly Pro Gln Gly Ile Pro Gly Ser Ala Gly Pro Gln Gly
    130                 135                 140

Gln Ala Gly Ala Ile Gly Pro Gln Gly Glu Gln Gly Leu Gln Gly Val
145                 150                 155                 160

Pro Gly Ile Gln Gly Leu Gln Gly Glu Ala Gly Pro Gln Gly Glu Gln
                165                 170                 175

Gly Pro Pro Leu Asn Leu Asp Gly Ile Thr Val Val Pro Glu Val Gln
            180                 185                 190

Arg Tyr Phe Tyr Phe Ala Asp Ser Asp Leu Thr Gly Thr Val Glu Ile
        195                 200                 205

Pro Ile Ser Gln Phe Thr Asn Asp Gly Gln Leu Ala Ser Gln Leu
    210                 215                 220

Pro Glu Leu Gly Ala Asn Ser Tyr Thr Asp Leu Tyr Ile Asn Gly Val
225                 230                 235                 240

Leu Gln Glu Ser Arg Leu Tyr Gln Ile Ser Ser Thr Thr Leu Thr Val
                245                 250                 255

Glu Leu Glu Glu Ala Leu Val Ile Ala Gly Thr Pro Phe Ile Phe Glu
            260                 265                 270

Val Phe Gln Phe Thr Leu Arg Met Ala Asn
        275                 280
```

<210> SEQ ID NO 31
<211> LENGTH: 60
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (2)..(2)

<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (54)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid

<400> SEQUENCE: 31

Met Xaa Val Xaa Ser Thr Gly Pro Ile Xaa Asn Xaa Xaa Val Xaa Gly
1               5                   10                  15

Xaa Arg Pro Thr Xaa Xaa Val Thr Val Lys Ile Asp Asn Arg Asp Xaa
                20                  25                  30

Val Asn Ser Ser Xaa Val Leu Ile Xaa Gly Phe Xaa Leu Asn Gly Xaa
            35                  40                  45

Arg Thr Leu Tyr Val Xaa Xaa Xaa Xaa Xaa Val Xaa
        50                  55                  60

<210> SEQ ID NO 32
<211> LENGTH: 120
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (2)..(2)
<223> OTHER INFORMATION: Xaa can be any naturally occurring amino acid

```
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (54)..(58)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (67)..(70)
<223> OTHER INFORMATION: Xaa can be any naturally occurring amino acid
<220> FEATURE:
<221> NAME/KEY: misc_feature
<222> LOCATION: (72)..(75)
<223> OTHER INFORMATION: Xaa can be any naturally occurring amino acid
<220> FEATURE:
<221> NAME/KEY: misc_feature
<222> LOCATION: (83)..(86)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (98)..(100)
```

```
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (117)..(120)
<223> OTHER INFORMATION: Xaa can be any naturally occurring amino acid

<400> SEQUENCE: 32

Met Xaa Val Xaa Ser Thr Gly Pro Ile Xaa Asn Xaa Xaa Val Xaa Gly
1               5                   10                  15

Xaa Arg Pro Thr Xaa Xaa Val Thr Val Lys Ile Asp Asn Arg Asp Xaa
            20                  25                  30

Val Asn Ser Ser Xaa Val Leu Ile Xaa Gly Phe Xaa Leu Asn Gly Xaa
            35                  40                  45

Arg Thr Leu Tyr Val Xaa Xaa Xaa Xaa Val Xaa Xaa Asn Xaa Val
        50                  55                  60

Ile Thr Xaa Xaa Xaa Xaa Ala Xaa Xaa Xaa Phe Glu Phe Val Phe
65                  70                  75                  80

Thr Thr Xaa Xaa Xaa Xaa Glu Asn Glu Xaa Gln Xaa Ser Val Trp Gly
            85                  90                  95

Lys Xaa Xaa Xaa Gly Gln Leu Val Xaa Ala His Arg Xaa Val Ser Xaa
            100                 105                 110

Glu Leu Leu Val Xaa Xaa Xaa Xaa
            115                 120
```